(12) United States Patent
Boddapati et al.

(10) Patent No.: US 11,278,612 B2
(45) Date of Patent: Mar. 22, 2022

(54) MULTIVALENT INFLUENZA NANOPARTICLE VACCINES

(71) Applicant: Novavax, Inc., Gaithersburg, MD (US)

(72) Inventors: Sarathi Boddapati, Germantown, MD (US); Anushree Herwadkar, Clarksburg, MD (US); Jason Wong, Rockville, MD (US); Yen-Huei Lin, Rockville, MD (US); Gale Smith, Germantown, MD (US); Jing-Hui Tian, Germantown, MD (US)

(73) Assignee: Novavax, Inc., Gaithersburg, MD (US)

( * ) Notice: Subject to any disclaimer, the term of this patent is extended or adjusted under 35 U.S.C. 154(b) by 0 days.

(21) Appl. No.: 16/357,876

(22) Filed: Mar. 19, 2019

(65) Prior Publication Data

US 2019/0314487 A1    Oct. 17, 2019

Related U.S. Application Data

(60) Provisional application No. 62/787,980, filed on Jan. 3, 2019, provisional application No. 62/644,623, filed on Mar. 19, 2018.

(51) Int. Cl.
| | |
|---|---|
| *A61K 39/145* | (2006.01) |
| *A61P 31/16* | (2006.01) |
| *A61K 9/51* | (2006.01) |
| *A61K 9/00* | (2006.01) |
| *A61K 39/00* | (2006.01) |

(52) U.S. Cl.
CPC .......... *A61K 39/145* (2013.01); *A61K 9/0051* (2013.01); *A61K 9/51* (2013.01); *A61P 31/16* (2018.01); *A61K 2039/70* (2013.01)

(58) Field of Classification Search
None
See application file for complete search history.

(56) References Cited

U.S. PATENT DOCUMENTS

| | | | |
|---|---|---|---|
| 4,900,549 A | 2/1990 | De Vries et al. | |
| 5,057,540 A | 10/1991 | Kensil et al. | |
| 5,149,650 A | 9/1992 | Wertz et al. | |
| 5,620,690 A | 4/1997 | Kersten et al. | |
| 6,231,859 B1 | 5/2001 | Kensil | |
| 6,245,532 B1 | 6/2001 | Smith et al. | |
| 6,352,697 B1 * | 3/2002 | Cox | A61K 36/73 424/278.1 |
| 6,428,807 B1 | 8/2002 | MacFarlan et al. | |
| 6,558,670 B1 | 5/2003 | Friede et al. | |
| 8,563,002 B2 | 10/2013 | Baudoux et al. | |
| 8,715,692 B2 | 5/2014 | Pushko et al. | |
| 8,821,881 B2 | 9/2014 | Morein et al. | |
| 9,675,685 B2 | 6/2017 | Pushko et al. | |
| 9,708,373 B2 | 7/2017 | Garcia-Sastre et al. | |
| 9,717,786 B2 | 8/2017 | Pushko et al. | |
| 9,731,000 B2 | 8/2017 | Pushko et al. | |
| 10,022,437 B2 | 7/2018 | Pushko et al. | |
| 10,426,829 B2 | 10/2019 | Smith et al. | |
| 10,729,764 B2 | 8/2020 | Morein et al. | |
| 2004/0028698 A1 | 2/2004 | Colau et al. | |
| 2005/0142148 A1 | 6/2005 | Fouchier et al. | |
| 2006/0121065 A1 | 6/2006 | Morein et al. | |
| 2006/0171917 A1 | 8/2006 | Campbell et al. | |
| 2006/0239963 A1 | 10/2006 | Morein et al. | |
| 2008/0233150 A1 | 9/2008 | Smith et al. | |
| 2010/0239617 A1 | 9/2010 | Pushko et al. | |
| 2010/0239671 A1 | 9/2010 | Edelman et al. | |
| 2010/0285135 A1 | 11/2010 | Wendorf et al. | |
| 2010/0291147 A1 | 11/2010 | Baudoux et al. | |
| 2013/0122032 A1 | 5/2013 | Smith et al. | |
| 2013/0123333 A1 | 5/2013 | Mirkin et al. | |
| 2013/0337005 A1 | 12/2013 | Rademacher et al. | |
| 2014/0227309 A1 | 8/2014 | Smith et al. | |
| 2014/0294879 A1 | 10/2014 | Pushko et al. | |
| 2014/0335049 A1 | 11/2014 | Morein et al. | |
| 2015/0202283 A1 | 7/2015 | Steff et al. | |
| 2015/0209425 A1 | 7/2015 | Morein et al. | |
| 2015/0265698 A1 | 9/2015 | Pushko et al. | |
| 2015/0266930 A1 | 9/2015 | Pushko et al. | |
| 2015/0306207 A1 | 10/2015 | Smith et al. | |
| 2015/0335730 A1 | 11/2015 | Smith et al. | |
| 2015/0359872 A1 | 12/2015 | Pushko et al. | |
| 2016/0184427 A1 | 6/2016 | Morein et al. | |

(Continued)

FOREIGN PATENT DOCUMENTS

| | | |
|---|---|---|
| AU | 200324520 B2 | 4/2009 |
| AU | 2014100888 A4 | 9/2014 |

(Continued)

OTHER PUBLICATIONS

Smith et al. (Vaccine, Aug. 22, 2017).*
Vaarala et al. (PLOS ONE, 2014, p. 1-23).*
Kanekiyo et al. (Nature, 2013, vol. 499, p. 102-108 in IDS on Mar. 10, 2020).*
Bengtsson et al, (Expert Review Vaccines, 2011 in IDS on Mar. 10, 2020).*
Nussbaum et al., "Fusion of influenza Virus particles with liposomes: requirement for cholesterol and virus receptors to allow fusion with and lysis of neutral but not of negatively charged liposomes",. Journal of General Virology, 2831-2837 (1992).
Vaarala et al., "Antigenic Differences between AS03 Adjuvanted Influenza a (H1N1) Pandemic Vaccines: Implications for Pandemrix Associated Narcolepsy Risk ," PLOS One, 1-23 (2014).
Lee et al., "Recent Advances of Vaccine Adjuvants for Infectious Diseases ," Immune Network, 51-57 (2015).

(Continued)

*Primary Examiner* — Agnieszka Boesen
(74) *Attorney, Agent, or Firm* — Cooley LLP

(57) ABSTRACT

Disclosed herein are multivalent nanoparticle vaccine compositions suitable for use in influenza vaccines. The nanoparticles include effective amounts of influenza glycoproteins that provide increased immune responses compared to a commercially available influenza vaccine composition. The present disclosure also provides vaccine formulation strategies that are cost effective and are convenient for clinical use. Methods of administering the nanoparticle vaccine compositions to a subject are also disclosed.

20 Claims, 37 Drawing Sheets

(56) References Cited

U.S. PATENT DOCUMENTS

| | | | |
|---|---|---|---|
| 2017/0202948 | A1 | 7/2017 | Smith et al. |
| 2017/0319682 | A1 | 11/2017 | Smith et al. |
| 2018/0133308 | A1 | 5/2018 | Smith et al. |
| 2018/0369368 | A1 | 12/2018 | Morein et al. |
| 2019/0134187 | A1 | 5/2019 | Pushko et al. |
| 2020/0101151 | A1 | 4/2020 | Smith et al. |
| 2020/0215189 | A1 | 7/2020 | Morein et al. |

FOREIGN PATENT DOCUMENTS

| | | |
|---|---|---|
| CA | 2491457 C | 9/2012 |
| CN | 101090711 A | 12/2007 |
| CN | 102107003 A | 6/2011 |
| EP | 0109942 A2 | 5/1984 |
| EP | 0362279 B1 | 1/1995 |
| EP | 1539231 B1 | 6/2009 |
| WO | WO 88/09336 A1 | 12/1988 |
| WO | WO 90/03184 A1 | 4/1990 |
| WO | WO 96/11711 A1 | 4/1996 |
| WO | WO 97/30728 A1 | 8/1997 |
| WO | WO 2001/066137 A1 | 9/2001 |
| WO | WO 2004/004762 A1 | 1/2004 |
| WO | WO 2005/002620 A1 | 1/2005 |
| WO | WO 2005/080417 A2 | 9/2005 |
| WO | WO 2007/149490 A1 | 12/2007 |
| WO | WO 2008/114149 A2 | 9/2008 |
| WO | WO 2008/133663 A2 | 11/2008 |
| WO | WO 2009/012487 A2 | 1/2009 |
| WO | WO 2009/108689 A1 | 9/2009 |
| WO | WO 2010/077717 A1 | 7/2010 |
| WO | WO 2010/138193 A2 | 12/2010 |
| WO | WO 2010/138193 A3 | 12/2010 |
| WO | WO 2011/008974 A2 | 1/2011 |
| WO | WO 2011/008974 A3 | 1/2011 |
| WO | WO 2012/061815 A2 | 5/2012 |
| WO | WO 2012/061815 A3 | 5/2012 |
| WO | WO 2013/006842 A2 | 1/2013 |
| WO | WO 2013/006842 A3 | 1/2013 |
| WO | WO 2013/049342 A1 | 4/2013 |
| WO | WO 2014/024024 A1 | 2/2014 |
| WO | WO 2014/124423 A1 | 8/2014 |
| WO | WO 2014/174018 A1 | 10/2014 |
| WO | WO 2015/042373 A1 | 3/2015 |

OTHER PUBLICATIONS

Demirjian and Levy, "Safety and Efficacy of Neonatal Vaccination," Eur. J. Immunol. 39(1):36-46 (2009).
European Search Report, EP Appl. No. 16166033.7, 10 pages (dated Aug. 10, 2016).
Glenn, "Recombinant, Insect Cell-Derived RSV Nanoparticle Vaccine," Novavax.com, 34 pages (Jul. 4, 2012) https://www.novavax.com/download/file/RSV nanoparticle Vaccine-MVADsJuly4(2).pdf.
Glenn et al., "Safety and immunogenicity of a Sf9 insect cell-derived respiratory syncytial virus fusion protein nanoparticle vaccine," Vaccine. Jan. 7, 2013;31(3):524-532.
International Search Report, 4 pages, PCT appl. No. PCT/US09/67269 (dated Mar. 4, 2010).
International Search Report, 5 pages, PCT appl. No. PCT/US2012/057546 (dated Jan. 22, 2013).
International Search Report, 6 pages, PCT appl. No. PCT/US2016/050413 (dated Feb. 21, 2017).
Parrington et al., "Baculovirus expression of the respiratory syncytial virus fusion protein using Trichoplusia ni insect cells," Virus Genes 14:63-72 (1997).
Smith et al., "Respiratory Syncytial Virus Fusion Glycoprotein Expressed in Insect Cells Form Protein Nanoparticles That Induce Protective Immunity in Cotton Rats," PLOS ONE 7(11):e50852, 12 pages (2012).
Smith et al., "Novel hemagglutinin nanoparticle influenza vaccine with Matrix-M™ adjuvant induces hemagglutination inhibition, neutralizing, and protective responses in ferrets against homologous and drifted A(H3N2) subtypes," Vaccine 35:5366-5372 (2017).
Supplementary European Search Report, EP Appl. No. 09836751.9, 9 pages (dated Apr. 29, 2013).
Supplementary European Search Report, EP Appl. No. 12835033.7, 7 pages (dated Feb. 17, 2015).
Written Opinion of the International Searching Authority, 4 pages, PCT appl. No. PCT/US09/67269 (dated Mar. 4, 2010).
Written Opinion of the International Searching Authority, 5 pages, PCT appl. No. PCT/US2012/057546 (dated Jan. 22, 2013).
Written Opinion of the International Searching Authority, 11 pages, PCT appl. No. PCT/US2016/050413 (dated Feb. 21, 2017).
Lovgren et al., The Requirement of Lipids for the Formation of Immunostimulating Complexes (Iscoms), Biotechnol. Appl. Biochem. 10:161-172 (1988).
Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).
Shi et al., "Stabilization of Human Papillomavirus Virus-Like Particles by Non-Ionic Surfactants," Journal of Pharmaceutical Sciences, 2005, p. 1538-1551.
Kanekiyo et al., "Self-assembling influenza nanoparticle vaccines elicit broadly neutralizing HINI antibodies," Nature 2013, vol. 499 p. 102-108.
Wu et al., "Active 1918 pandemic flu viral neuraminidase has distinct N-glycan profile and is resistant to trypsin digestion," Biochemical and Biophysical Research, 2009, vol. 379. p. 749-753.
Karin Lovgren Bengtsson, Bror Morein & Albert DME Osterhaus (2011) ISCOM technology-based Matrix M™ adjuvant: success in future vaccines relies on formulation, Expert Review of Vaccines, 10:4, 401-403, DOI: 10.1586/erv.11.25.
Tekewe et al., A rapid and simple screening method to identify conditions for enhanced stability of modular vaccine candidates, Biochemical Engineering Journal 100:50-58 (2015).
Iyer et al., Purified, Proteolytically Mature HIV Type 1 SOSIP gp140 Envelope Trimers, AIDS Research and Human Retroviruses 23(6):817-828 (2007).
European Search Report, EP Appl. No. 16843191.4, 13 pages, dated Mar. 14, 2019.
International Search Report and Written Opinion issued by the International Searching Authority for Application No. PCT/US2019/022930, dated Aug. 8, 2019, 14 pages.
Giannos et al., Formulation Stabilization and Disaggregatoin of Bevacizumab, Ranibizumab and Aflibercept in Dilute Solutions, Pharm Res 35:78 (2018), 15 pages.
Makwana et al., "Prefilled Syringes: An Innovation in Parenteral Packaging," International Journal of Pharmaceutical Investigation 1(4):200-206.
Shinde et al., "Improved Titers Against Influenza Drift Variants with a Nanoparticle Vaccine," N Engl Med 378:24 (2018), 3 pages.
Shinde et al, Induction of Broadly Cross-Reactive Immune Responses Against A(H3N2) Viruses: Results of a Phase 2 Trial of a Novel Recombinant Hemagglutinin Saponin-Adjjvanted nanoparticle Influenza Vaccine ("NanoFlu"), 30 pages (2018).
Lichtenberg et al., "The Mechanism of Detergent Solubilization of Lipid Bilayers," Biophysical Journal, vol. 105:289-299 (2013).
"Novavax' NanoFlu Achieves All Primary Endpoints in Phase 3 Clinical Trial," Press Release dated Mar. 24, 2020, 3 pages.
Citovsky et al., "Fusion of Sendai Virions or Reconstituted Sendai Virus Envelopes with Liposomes or Erythrocyte Membranes Lacking Virus Receptors," The Journal of Biological Chemistry 260(22)12072-12077 (1985).
"Safety Evaluation of Certain Food Additives and Contaminants Quillaja Extracts," WHO Food Additives, WHO (first draft, Eastwood et al., Series:48, pp. 1-14 (2001).
Adjuvanting Viral Vectored Malaria Vaccines with Matrix M, Identifier NCT01669512, ClinicaiTrials.gov, U.S. National Institutes of Health; available at http://clinicaltrials.gov/ct2/show/NCT01669512?term=MatrixM+or+Matrix+M&rank=1, Mar. 9, 2014, pp. 1-4.
Ahlberg et al., Global transcriptional response to ISCOM-Matrix adjuvant at the site of administration and in the draining lymph node

(56) References Cited

OTHER PUBLICATIONS early after intramuscular injection in pigs, Developmental and Comparative Immunology, vol. 38, pp. 17-26 (2012), Elsevier Ltd.
Barr et al., "ISCOMs and other saponin based adjuvants," Advanced Drug Delivery Reviews, (1998), 32: 247-271.
Behboudi et al., "Quillaja Saponin Formulations that Stimulate Proinflammatory Cytokines Elicit a Potent Acquired Cell-Mediated Immunity," Scand. J. Immunol. 50:371-377 (1999).
Bengtsson et al., Matrix-M adjuvant increases immunogenicity of seasonal influenza vaccine for the elderly, manuscript in preparation, pp. 1-27 (2014).
Boulter, et al., Evaluation of recombinant sporozoite antigen SPAG-1 as a vaccine candidate against Theileria annulata by the use of different delivery systems, Tropical Medicine and International Health, vol. 4, pp. A71-A77 (1999), Blackwell Science, Ltd.
Copland et al., "Hydration of lipid films with an aqueous solution of Quil A: a simple method for the preparation of immune-stimulating complexes," International Journal of Pharmaceutics 196:135-139 (2000).
Coulter, et al., Studies on experimental adjuvanted influenza vaccines: comparison of immune stimulating complexes(Iscoms) and oil-in-water vaccines; Vaccine, vol. 16, No. 11/12, pp. 1243-1253 (1998), Elsevier Science Ltd., Great Britain.
Cox, et al., Development of an Influenza-ISCOM Vaccine, in Vaccine Design (eds. G. Gregoriadis et al.), Springer Science+Business Media, New York (1997), pp. 33-49.
Cox, et al., Evaluation of a virosomal H5N1 vaccine formulated with Maxtrix M adjuvant in phase I clinical trial, Elsevier Ltd, Vaccine, 29, pp. 8049-8059, Aug. 22, 2011.
Cox, et al., Prospects for the Development of New Vaccine Adjuvants, BioDrugs, vol. 12(6), pp. 439-453 (1999), Ad is International Limited.
Demana et al., "Pseudo-ternary phase diagrams of aqueous mixtures of Quil A, cholesterol and phospholipid prepared by the lipid-film hydration method," International Journal of Pharmaceutics 270:229-239 (2004).
Drane et al., "Iscomatrix™ adjuvant for prophylactic and therapeutic vaccines," Expert Rev. Vaccines 6:761-772 (2007).
Ekstrom et al., "Iscom and iscom-matrix enhance by intranasal route the IgA responses to OVA and rCTB in local and remote mucosal secretions," Vaccine 17:2690-2701 (1999).
EMEA (European Agency for the Evaluation of Medicinal Products), "Committee for Veterinary Medicinal Products. Quillaia Saponins. Summary Report ," EMEA/MRL/055/95-FINAL, pp. 1-2 (1996).
Ennis et al., "Augmentation of Human Influenza A Virus-Specific Cytotoxic T Lymphocyte Memory by Influenza Vaccine and Adjuvanted Carriers (ISCOMS)," Virology 25:256-261 (1999).
Eyles et al., "Immunodominant Francisella tularensis antigens identified using proteome microarray," Proteomics 7:2172-2183 (2007).
Fossum et al., Early inflammatory response to the saponin adjuvant Matrix-M in the pig, Veterinary Immunology and Immunopathology, http://dx.doi.org/10.1016/j.vetimm.2013.07.007 (2013), pp. 1-9, Elsevier B.V.
Genocea Biosciences, Genocea Reports Positive Initial Phase 1/2A Results for GEN-003, It's Pioneering Therapeutic Vaccine Candidate for the Treatment of Herpes Simplex Virus-2 (HSV-2), at ICAAC 2013, press release, Cambridge MA, Sep. 12, 2013, pp. 1-3.
Johansson et al., "Iscoms with different quillaja saponin components differ in their immunomodulating activities," Vaccine 17:2894-2900 (1999).
Kensil, Saponins as Vaccine Adjuvants, Critical Reviews in Therapeutic Drug Carrier Systems, vol. 13(1&2), pp. 1-55 (1996), Begell House, Inc.
Kersten et al., On the structure of immune-stimulating saponin-lipid complexes (iscoms) Biochimica et Biophysica Acta, 1062:165-171 (1991).
Lavelle et al., "Cholera Toxin Promotes the Induction of Regulatory T Cells Specific for Bystander Antigens by Modulating Dendritic Cell Activation," Journal of Immunology 171:2384-2392 (2003).
Lovgren-Bengtsson et al., "4.5 Preparation and Use of Adjuvants," Methods in Microbiology 32:551-588 (2002).
Lovgren-Bengtsson, 6 Preparation and Use of Adjuvants; Methods in Microbiology, vol. 25, pp. 471-502 (1998), Academic Press Ltd.
Lucy et al., "Structure and Assembly of Macromolecular Lipid Complexes Composed of Globular Micelles," Journal of Molecular Biology, (1964), 8: 727-748.
Magnusson et al., Immune enhancing properties of the novel Matrix-M adjuvant leads to potentiated immune responses to an influenza vaccine in mice, Vaccine, http://dx.doi.org/10.1016/j.vaccine.2013.01.039 (2013), pp. 1-9, Elsevier Ltd.
Magnusson et al., Matrix-M adjuvanted envelope protein vaccine protects against lethal lineage 1 and 2 West Nile virus infection in mice, Vaccine vol. 32, pp. 800-808 (2014), Elsevier Ltd.
McKenzie et al., ISCOMATRIX vaccines: Safety in human clinical studies, Human Vaccines, vol. 6, No. 3, pp. 237-246 (2010), Landes BioScience.
Morein et al., "Current status and potential application of ISCOMs in veterinary medicine," Advanced Drug Delivery Reviews 56:1367-1382 (2004).
Nord et al., "Novel acetylated triterpenoid saponins in a chromatographic fraction from Quillaja saponaria Molina," Carbohydrate Research 329:817-829 (2000).
Ozel et al., "Quaternary Structure of the Immunostimulating Complex (Iscom)," Journal of Ultrastructure and Molecular Structure Research 102:240-248 (1989).
Pedersen et al., Matrix-M adjuvanted virosomal H5N1 vaccine confers protection against lethal viral challenge in a murine model, Influenza and Other Respiratory Viruses. DOI: 1 0.1111/j.1750-2659.2011.00256.x (2011 ), pp. 1-12, Blackwell Publishing Ltd.
Pedersen, et al.; T-Helper 1 Cells Elicited by H5N1 Vaccination Predict Seroprotection, Journal of Infectious Disease, 206, pp. 158-166, Jul. 15, 2016.
Rimmelzwaan et al., "A randomized, double blind study in young healthy adults comparing cell mediated and humoral immune responses induced by influenza ISCOM™ vaccines and conventional vaccines," Vaccine 19:1180-1187 (2001).
Ronnberg et al., "Adjuvant activity of non-toxic Quillaja saponaria Molina components for use in ISCOM matrix," Vaccine, vol. 13, No. 14, pp. 1375-1382 (1995).
Safety and Immunogenicity Study of Therapeutic HSV-2 Vaccine, Identifier NCT01667341, ClinicaiTrials.gov, U.S. National Institutes of Health; available at http://clinicaltrials.gov/ct2/show/NCT01667341 ?term=matrix+m&rank=3, Mar. 9, 2014, pp. 1-4.
Sjolander, et al., ISCOMs: an adjuvant with multiple functions, Journal of Leukocyte Biology, vol. 64, pp. 713-723 (1998).
Sjolander, et al., Uptake and adjuvant activity of orally delivered saponin and ISCOM vaccines, Advanced Drug Delivery Reviews, vol. 34, pp. 321-338 (1998), Elsevier Science B.V.
Skoberne et al., An adjuvanted herpes simplex virus 2 subunit vaccine elicits a T cell response in mice and is an effective therapeutic vaccine in Guinea pigs, J. Virol. 87:3930-3942 (2013).
Sun et al., "Advances in saponin-based adjuvants," Vaccine 27:1787-1796 (2009).
Sun et al., "ISCOMs and ISOMATRIX™," Vaccine 27:4388-4401 (2009).
Wald et al., Novel Therapeutic Vaccine for Genital Herpes Reduces Genital HSV-2 Shedding, in ICAAC 2013, Denver, CO, Sep. 2013, cover page and p. 279, Abstract 183(G).
Wald, "A Novel Therapeutic Vaccine (GEN003) for Genital Herpes Reduces HSV-2 Shedding: Initial Results of Clinical Trial GEN003-001," Presented at Interscience Conference on Antimicrobial Agents and Chemotherapy (ICAAC 2013), Denver, CO, Sep. 12, 2013, pp. 1-21.
Wang et al., "Expression and purification of an influenza hemagglutinin-one step closer to a recombinant protein-based influenza vaccine," Vaccine vol. 24, Issue 12, pp. 2176-2185 (2006).
Eckert et al., "Mechanisms of Viral Membrane Fusion and Its Inhibition," Annual Review of Biochemistry 70:770-810 (2001).
Gruenke et al., "New Insights into the Spring-Loaded Conformational Change of Influenza Virus Hemagglutinin," Journal of Virology, May 2002, 76:(9) 4456-4466 (2002).

(56) References Cited

OTHER PUBLICATIONS

Wang, "Protein aggregation and its inhibition in biopharmaceutics," International Journal of Pharmaceutics 289 (2005) 1-30.

* cited by examiner

FIG. 1: HaSMaN Structures vs Matrix M and detergent core HA nanoparticles

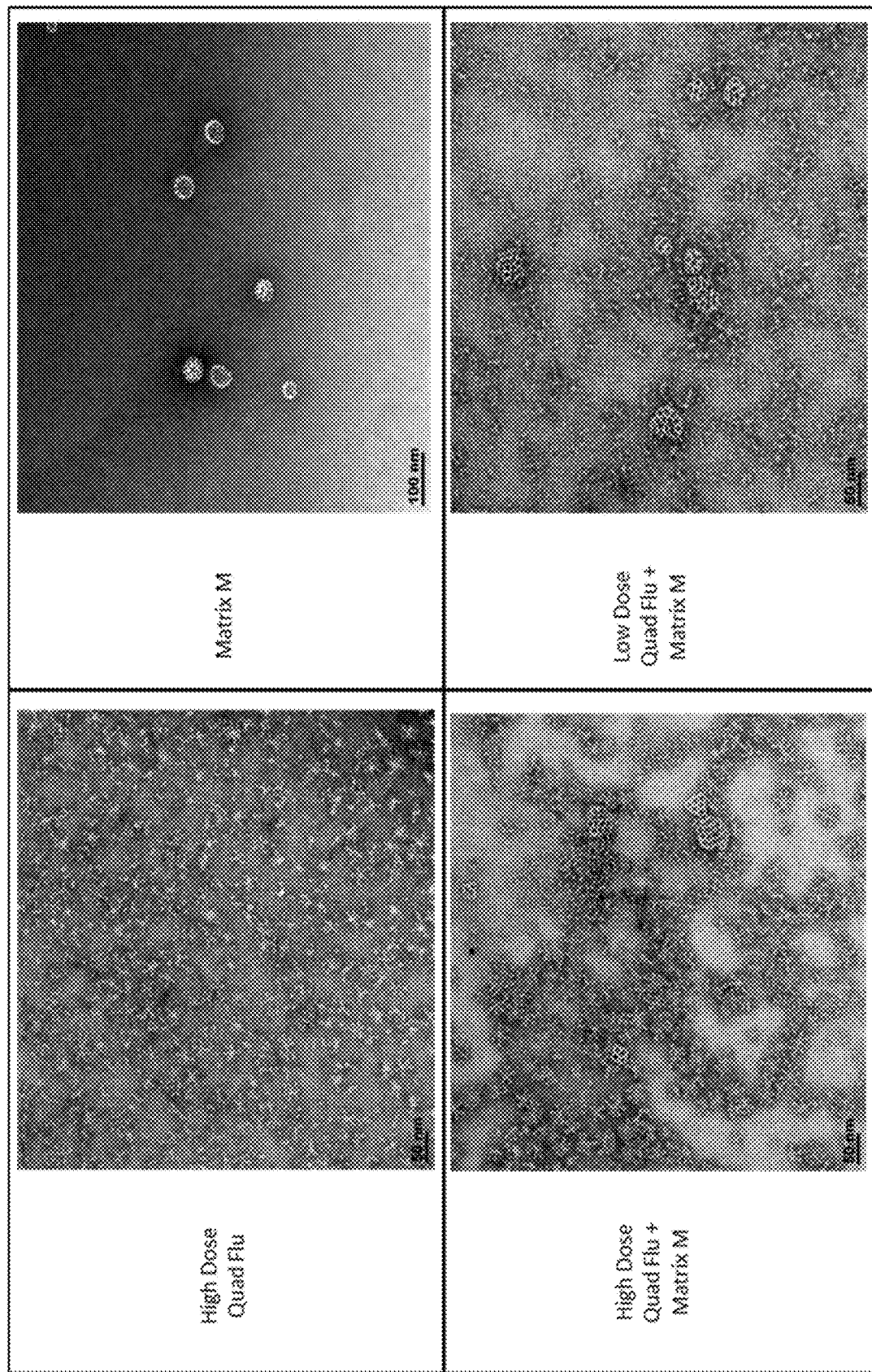
FIG. 30 HaSMaN formation at Time Zero

FIG. 31 HaSMaN formation at 4 hours

Low Dose
Quad Flu +
Matrix M
4C

Low Dose
Quad Flu +
Matrix M
25C

High Dose
Quad Flu +
Matrix M
4C

High Dose
Quad Flu +
Matrix M
25C

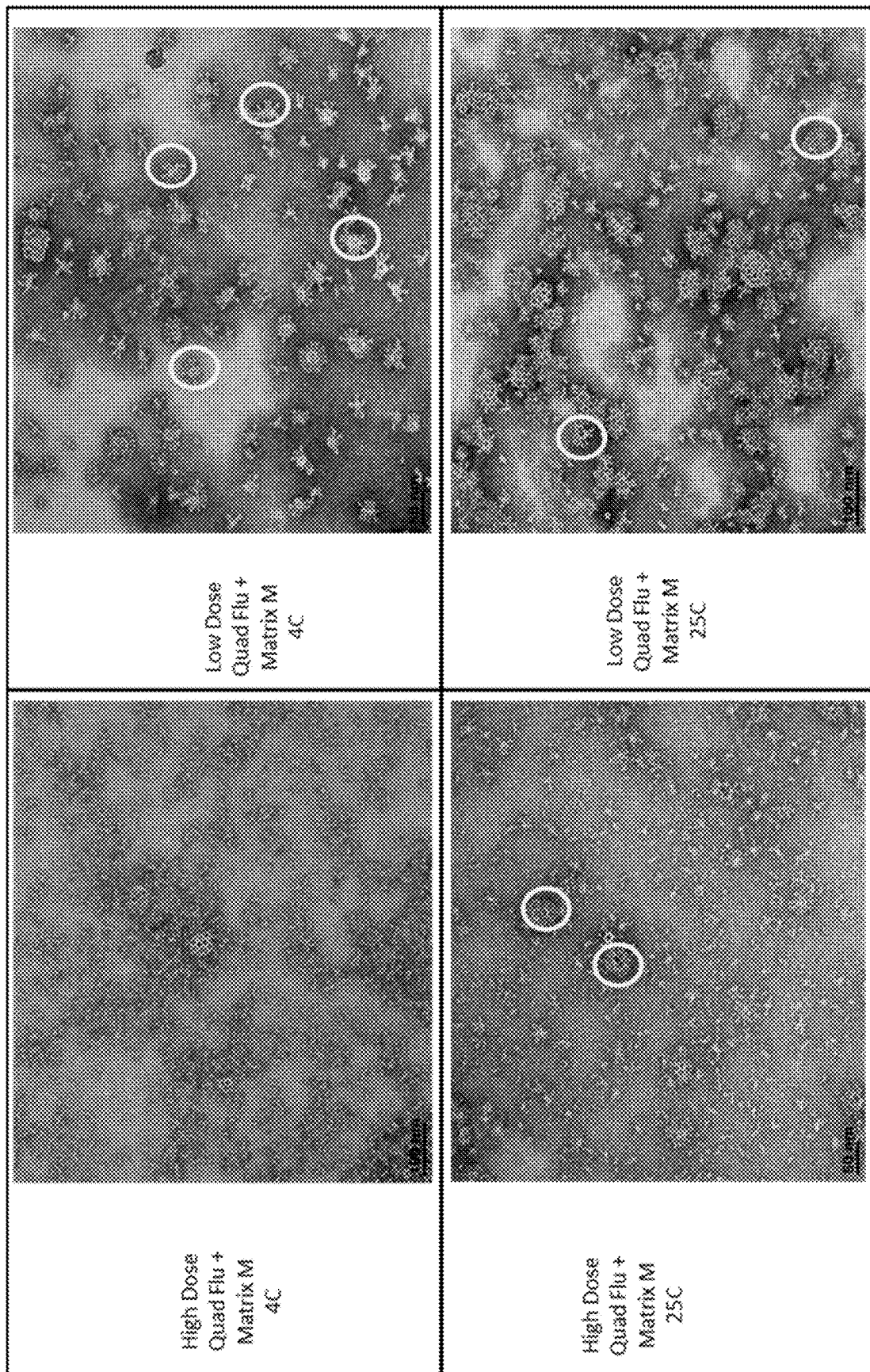
FIG. 32 HaSMaN formation at 24 hours

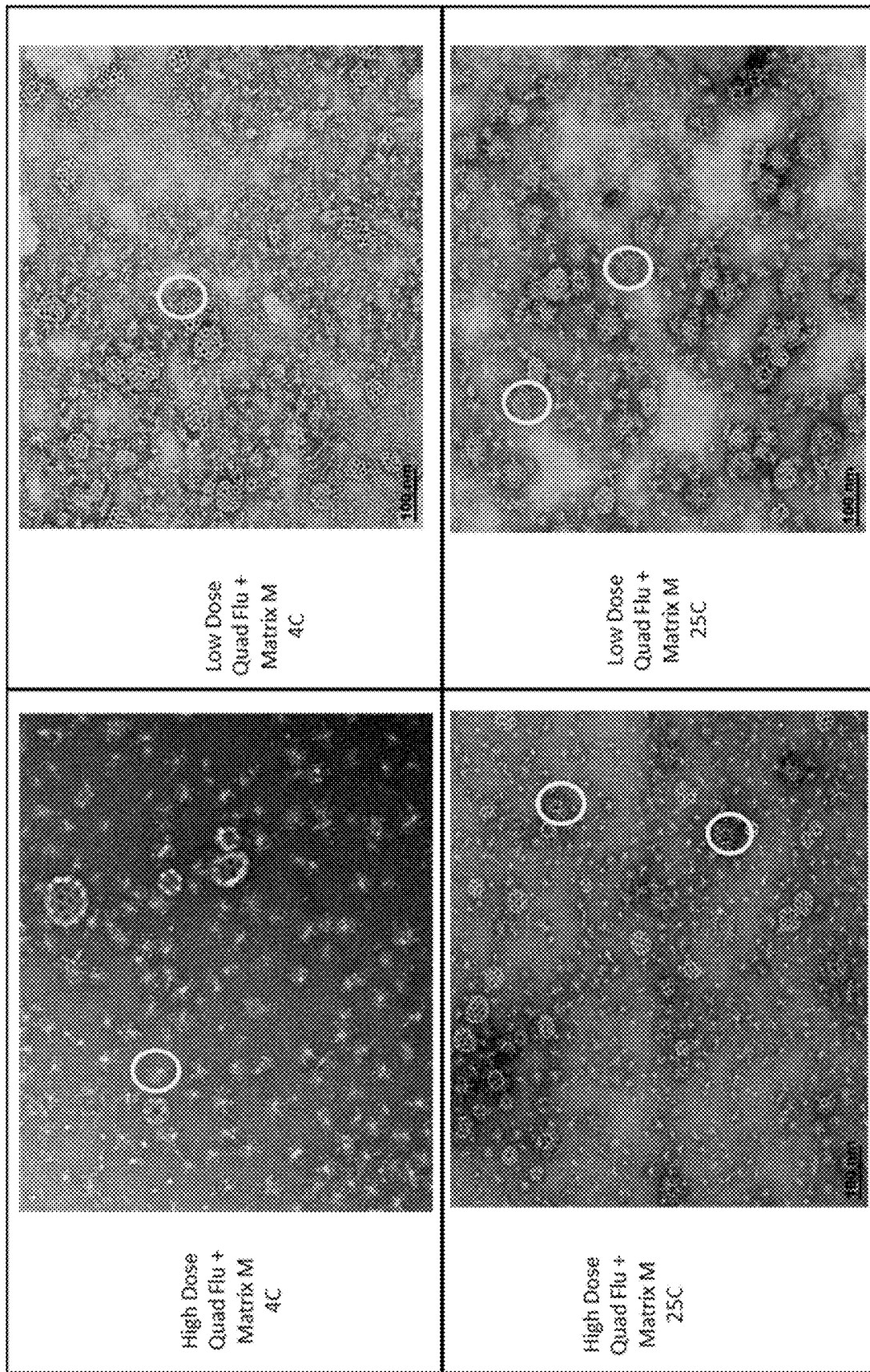
FIG. 33: HaSMaN formation at 48 hours

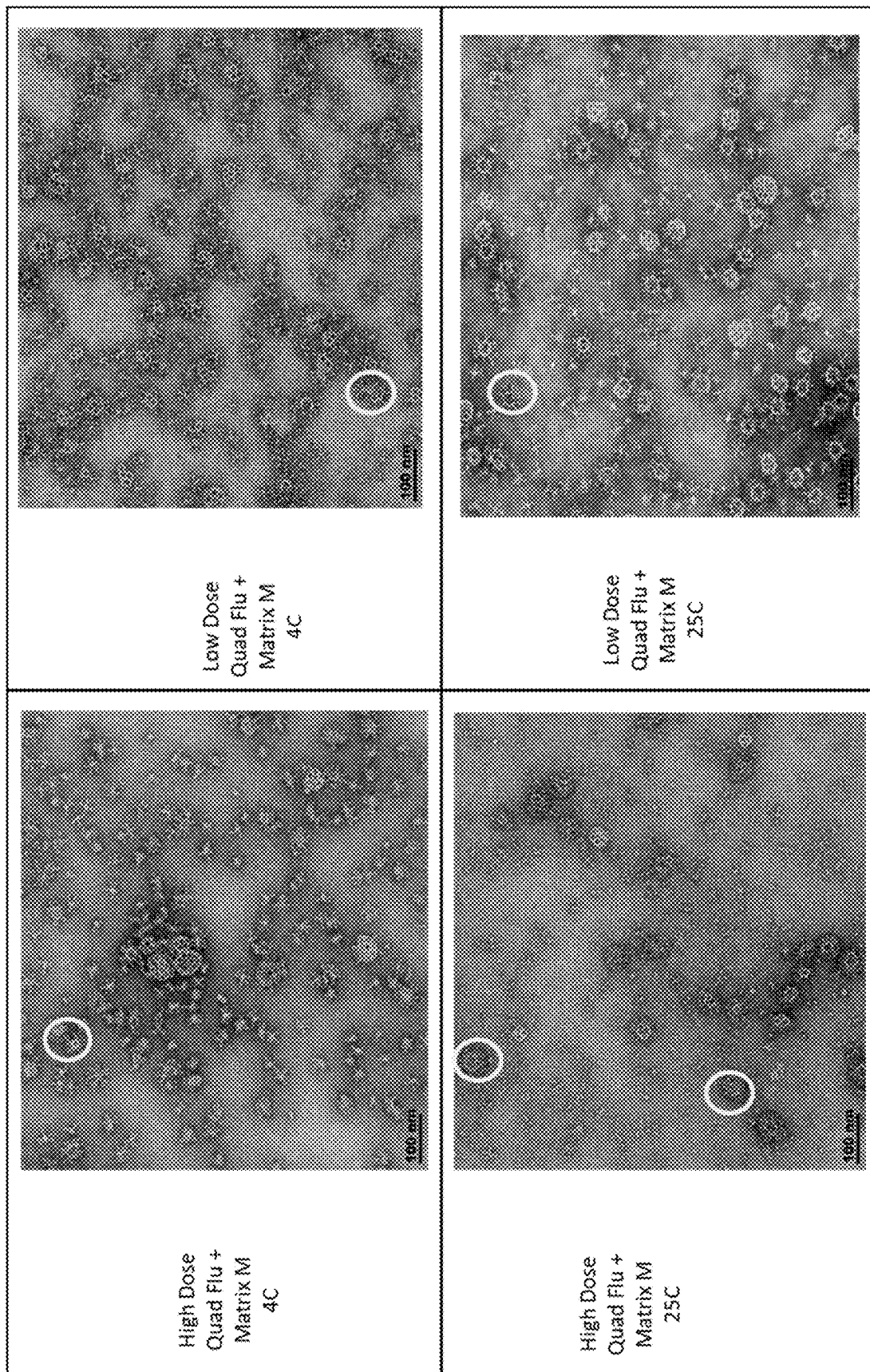
FIG. 34 HaSMaN formation at 7 days

FIG. 37: Type A but not Type B strain HA glycoproteins form HaSMaNs

MULTIVALENT INFLUENZA NANOPARTICLE VACCINES

CROSS REFERENCE TO RELATED APPLICATIONS

This application claims the benefit under 35 U.S.C. § 119(e) of U.S. Provisional Patent Application No. 62/644,623, filed Mar. 19, 2018; and U.S. Provisional Patent Application No. 62/787,980, filed Jan. 3, 2019, the contents of each of which are incorporated herein by reference in their entireties for all purposes.

The application also incorporates herein by reference the contents of U.S. application Ser. No. 15/257,436, filed Sep. 6, 2016; and U.S. application Ser. No. 15/819,962, filed Nov. 21, 2017, in their entireties for all purposes.

TECHNICAL FIELD

The present disclosure is generally related to influenza vaccine compositions useful for stimulating immune responses against influenza.

BACKGROUND

The substantial global burden of seasonal influenza has been well documented. In the US alone, around 140,000 to 10,000 hospitalizations and 12,000 to 56,000 deaths are attributable to influenza annually, with older adults accounting for a disproportionate 62% of hospitalizations and 72% of mortality. Seasonal influenza vaccination has been the mainstay of prevention efforts and has been universally recommended in the US since 2010.

However, recent developments, including a severe 2017-2018 A (H3N2) predominant US influenza season, illustrate poor vaccine effectiveness in at least Australia, Canada, and the US. Other issues such as antigenic mismatch associated with egg-based influenza vaccines, and the persistent challenge of antigenic drift also represent the need to provide more effective vaccination strategies.

Therefore, there is continuing interest in producing vaccines against influenza viruses and there remains an ongoing need to produce effective vaccines, particularly using recombinant egg-protein free approaches.

SUMMARY

The present disclosure provides multivalent influenza compositions. The compositions stimulate immune responses against multiple influenza strains. Advantageously, the immune responses may include broadly neutralizing antibodies directed to variants of the strains different from those used to prepare the compositions. Influenza mutations result in "drifted strains," and the disclosed compositions provide protection against "drifted strains". In addition, the compositions exhibit excellent stability and may be stored for extended periods and may be produced in pre-filled syringes that are ready to administer. In some aspects, a pre-filled syringe (PFS) may already contain adjuvant and influenza antigen and may be stored for extended periods. Compositions disclosed herein need not be refrigerated (2-8° C.), showing good stability at higher temperatures (e.g room temperature, about 25° C.). The compositions disclosed herein therefore offer excellent convenience as well as excellent immune responses.

In particular aspects, nanoparticles containing influenza antigens are co-formulated into vaccine compositions by mixing with ISCOM Matrix adjuvant (also referred to herein as "Matrix") for a time to form HaSMaNs (Hemagglutinin Saponin Matrix Nanoparticles) prior to administration to a subject. Compositions containing HaSMaNs exhibit good stability and immunogenicity and are thus well-suited for packaging, in pre-filled syringes, for example. Indeed, the HaSMaNs are more stable than the detergent core nanoparticles. Thermal stability measured by differential scanning calorimetry was better by about 1 degree for HaSMaNs compared to detergent core nanoparticles. Previously, approaches to using ISCOM Matrix adjuvant involved combining the vaccine composition with the adjuvant at the bed-side immediately prior to administration. In particular aspects, the compositions disclosed herein eliminate that requirement, thus providing improved methods of inducing immune responses. It was surprisingly discovered that formation of the HaSMaNs varies depending on the influenza type. HaSMaNs typically form when the compositions contain hemagglutinin (HA) proteins from Type A influenza strains, but do not form when the HA proteins are from Type B influenza strains.

In some embodiments, the ISCOM matrix adjuvant in the multivalent influenza composition is Matrix M, a combination of two types of Matrix, a first type, Matrix A containing saponin Fraction A (also referred to herein as Fraction A Matrix), and a second type, Matrix C, containing saponin Fraction C (also referred to herein as Fraction C Matrix). In certain aspects, Matrix M may contain at least about 85% (w/w) Fraction A Matrix, with the remainder as Fraction C Matrix. Unless referred to otherwise the Matrix M used herein contains Fraction A Matrix and Fraction C Matrix at a ratio of 85:15 (w/w), also referred to herein as Matrix M1.

In some embodiments, each influenza HA protein in the quadrivalent nanoparticle influenza composition can be from a different influenza strain. In some embodiments, at least one strain can be a sub-type A strain or a sub-type B strain. In some embodiments, the sub-type A strain may be complexed to the Matrix M adjuvant but the sub-type B strains are not.

While multivalent compositions are envisaged by this disclosure, particularly for use in seasonal vaccines, monovalent vaccine compositions may also be produced with HaSMaNs for use, for example, to vaccinate against pandemic influenza strains that arise from time to time.

Stability, particularly room temperature stability, is a valuable property because it reduces or eliminates the need for cold chain storage, making distribution cheaper and easier to achieve. Advantageously, the multivalent compositions disclosed herein are stable for extended periods of time, for example up to 3 months, up to 6 months, up to 12 months and at room temperature (i.e., about 25° C.) for these periods. The excellent stability, particularly when formulated with Matrix M adjuvant, means that the vaccine compositions are suited for delivery to clinical settings in a ready-to-administer format; for example, prefilled syringe formulations.

Figure 1:
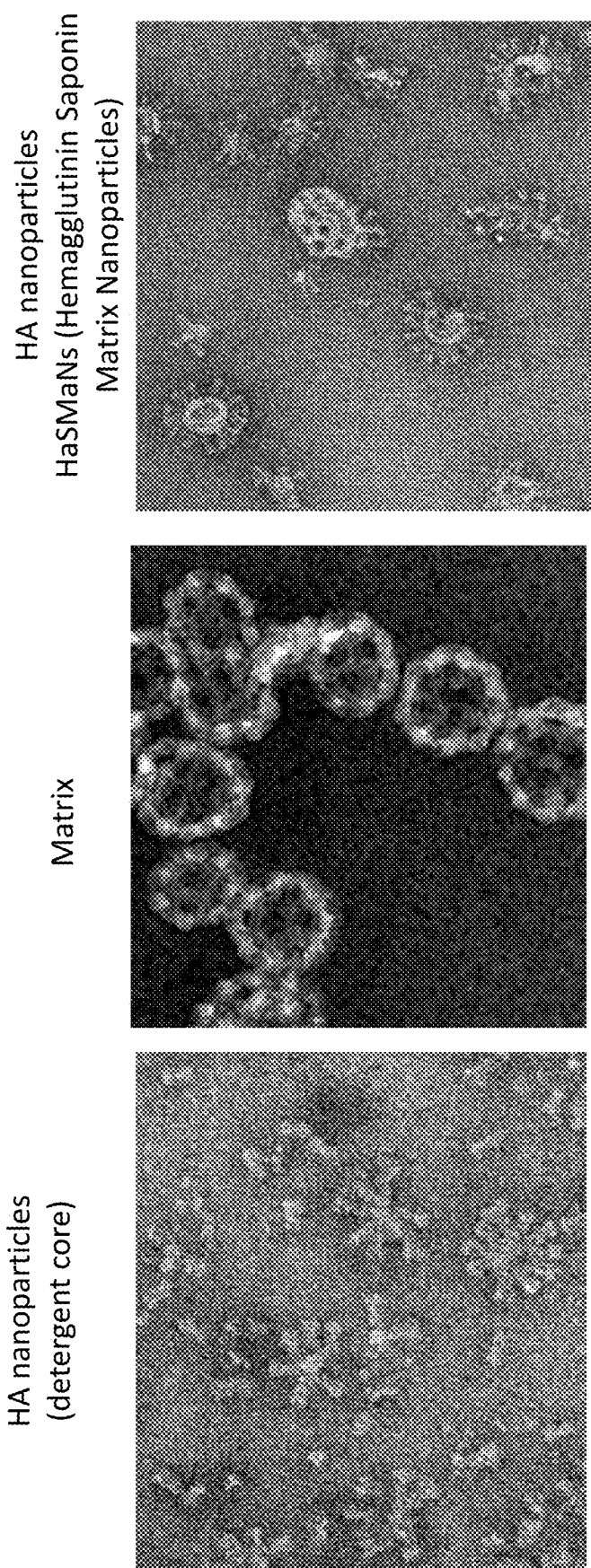
FIG. 1 shows examples of transmission electron microscopy (TEM) images of influenza HA detergent core nanoparticles alone (left), Matrix M alone (middle), and the combination of HA nanoparticles and Matrix M, which forms Hemagglutinin Saponin Matrix Nanoparticles (HaSMaNs) (right).
Figure 2:
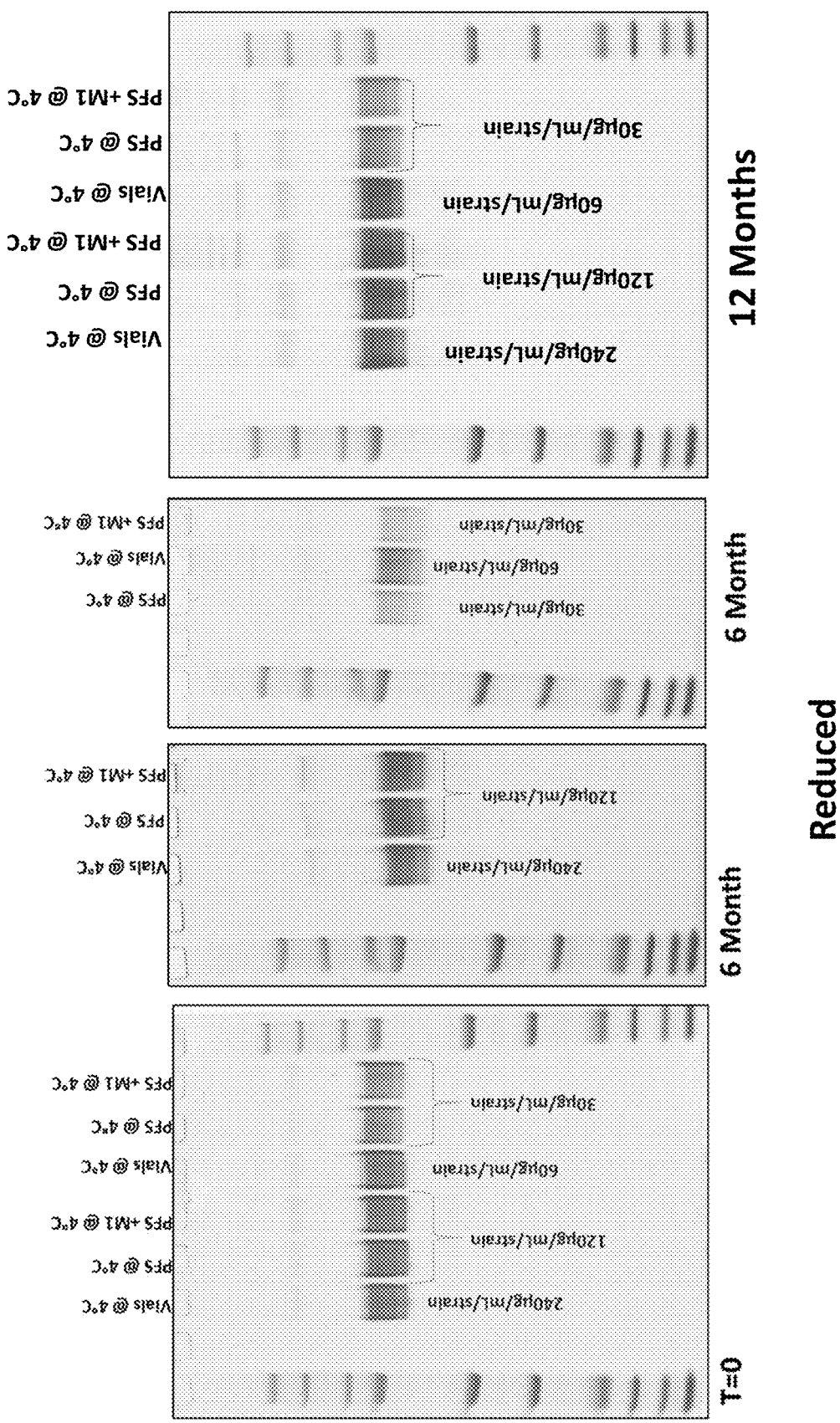
FIG. 2 illustrates reduced SDS-PAGE gel images for influenza antigens of high dose and low dose quadrivalent bedside vial formulations (240 µg/mL/strain and 60 µg/mL/strain); and pre-filled syringe (PFS) formulations (120 µg/mL/strain and 30 µg/mL/strain) with or without Matrix M at 4° C. at T=0, 6 months and 12 months. Abbreviations in the figure are PFS: prefilled syringes; M1: Matrix M.
Figure 3:
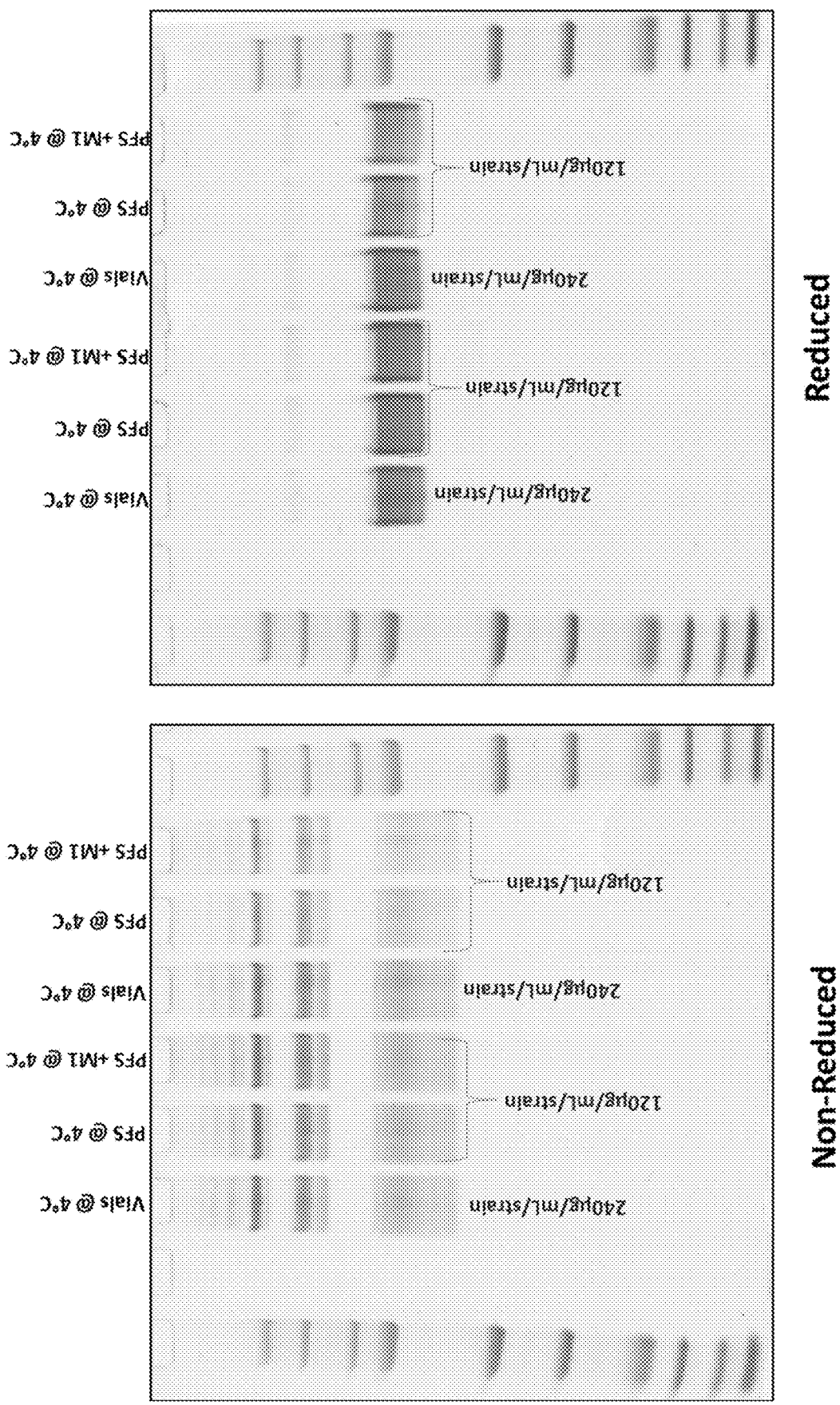
FIG. 3 illustrates non-reduced and reduced SDS-PAGE gel images for influenza antigens of high dose bedside vial formulations (240 µg/mL/strain); and PFS formulations (120 µg/mL/strain) with or without Matrix M at 4° C. at Time=0.

The terms "treat," "treatment," and "treating," as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), microneutralization assay, and HAI titers.

As used herein, the term "vaccine" refers to an immunogenic composition, such as an immunogen derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a subject to produce protective immunity.

As used herein, the term "subject" includes humans and other animals. Typically, the subject is a human. For example, the subject may be an adult, a teenager, a child (2 years to 14 years of age), an infant (1 month to 24 months), or a neonate (up to 1 month). In some aspects, the adults are seniors about 65 years or older, or about 60 years or older. In typical aspects, the adults are about 60 to about less than 75 years old, or at least about 75 years old. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

Nanoparticles: Structure and Morphology

The compositions disclosed herein comprise two types of nanoparticles. A first type, referred to as detergent-core nanoparticles are essentially as described previously. See U.S. Ser. No. 15/257,436, which is incorporated herein by reference for all purposes. Briefly, these nanoparticles are produced in insect cells by expressing HA proteins using baculovirus expression systems and then extracting the HA proteins with detergent. During purification, the first detergent is changed for a second detergent, typically a non-ionic detergent resulting in nanoparticles having a non-ionic detergent core which the terminal portion of the HA protein, in trimer form, is embedded into. FIG. 1 (left panel) illustrates these structures as observed under electron microscope.

A second type of nanoparticle is referred to herein as a HaSMaN (Hemagglutinin Saponin Matrix Nanoparticle.) FIG. 1 (right panel) illustrates these structures as observed under electron microscope. The HA glycoproteins decorate the Matrix cage-like structures. The HaSMaN structures are formed by preparing HA nanoparticles and then incubating them with ISCOM matrix adjuvant particles for a period of time. ISCOM matrix particles are shown in the center panel of FIG. 1. Notably, the HaSMaNs form readily with Type A influenza HA proteins, but not Type B. Accordingly, in particular aspects, compositions containing nanoparticles having HA proteins from Type A and Type B will contain both types of nanoparticles (i.e., detergent core nanoparticles and HaSMaNs). In some aspects, the nanoparticles will be transitioning between the two states and thus compositions may contain transitional nanoparticles.

In particular embodiments, the detergent core nanoparticles are composed of multiple protein trimers surrounding a non-ionic detergent core. For example, each nanoparticle may contain 1, 2, 3, 4, 5, 6, 7, 8, 9, 10, 11, 12, or 15 trimers. In some embodiments, each nanoparticle contains 2 to 6 trimers. In particular embodiments, each nanoparticle contains 2 to 9 trimers.

The HA proteins are associated with the non-ionic detergent-containing core of the nanoparticle. Typically, the detergent is selected from polysorbate-20 (PS20), polysorbate-40 (PS40), polysorbate-60 (PS60), polysorbate-65 (PS65) and polysorbate-80 (PS80). The presence of the detergent facilitates formation of the nanoparticles by forming a core that organizes and presents the antigens. Thus, in certain embodiments, the nanoparticles contain the antigens assembled into multi-oligomeric glycoprotein-PS80 protein-detergent nanoparticles with the head regions projecting outward and hydrophobic regions and PS80 detergent forming a central core surrounded by the antigens. In particular embodiments, the non-ionic detergent in influenza vaccine compositions is PS80. The detergent core nanoparticles range in Z-ave size from about 25 nm to about 30 nm. Once the detergent core nanoparticles are combined with Matrix M for a time, however, the HaSMaNs are formed and those are slightly larger than detergent core nanoparticles, about 50 nm to 60 nm. Particle size (Z-ave) is measured by dynamic light scattering (DLS) using a Malvern Zetasizer, unless otherwise specified.

Nanoparticles: Production

The detergent-core nanoparticles and HaSMaNs of the present disclosure are non-naturally occurring products, the components of which do not occur together in nature. Generally, the methods disclosed herein use a detergent exchange approach wherein a first detergent is used to isolate a protein and then that first detergent is exchanged for a second detergent to form the nanoparticles.

The glycoprotein antigens, typically HA, in the nanoparticles are typically produced by recombinant expression in host cells. Typically, the glycoproteins are expressed in insect host cells using a baculovirus system. In preferred embodiments, the baculovirus is a cathepsin-L knock-out baculovirus. In other preferred embodiments, the baculovirus is a chitinase knock-out baculovirus. In yet other preferred embodiments, the baculovirus is a double knock-out for both cathepsin-L and chitinase. High level expression may be obtained in insect cell expression systems. Non limiting examples of insect cells are, *Spodoptera frugiperda* (Sf) cells, e.g. Sf9, Sf21, *Trichoplusia ni* cells, e.g. High Five cells, and *Drosophila* S2 cells. Preferably, the cells are Sf9 cells, or a derivative thereof.

Typical transfection and cell growth methods can be used to culture the cells. Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 3500 L bags.

Detergent Extraction and Purification of Nanoparticles

After growth of the host cells, the protein may be harvested from the host cells using detergents and purification protocols. Once the host cells have grown for 48 to 96 hours, the cells are isolated from the media and a detergent-containing solution is added to solubilize the cell membrane, releasing the protein in a detergent extract. Triton X-100 and tergitol, also known as NP-9, are each preferred detergents for extraction. The detergent may be added to a final concentration of about 0.1% to about 1.0%. For example, the concentration may be about 0.1%, about 0.2%, about 0.3%, about 0.5%, about 0.7%, about 0.8%, or about 1.0%. In certain embodiments, the range may be about 0.1% to about 0.3%. Preferably, the concentration is about 0.5%.

In other aspects, different first detergents may be used to isolate the protein from the host cell. For example, the first detergent may be Bis(polyethylene glycol bis[imidazoylcarbonyl]), nonoxynol-9, Bis(polyethylene glycol bis[imidazoyl carbonyl]), Brij® 35, Brij®56, Brij® 72, Brij® 76, Brij® 92V, Brij® 97, Brij® 58P, Cremophor® EL, Decaethyleneglycol monododecyl ether, N-Decanoyl-N-methylglucamine, n-Decyl alpha-Dglucopyranoside,Decyl beta-D-maltopyranoside, n-Dodecanoyl-N-methylglucamide, nDodecyl alpha-D-maltoside, n-Dodecyl beta-D-maltoside, n-Dodecyl beta-D-maltoside,Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630,Igepal CA-630, Methyl-6-0-(N-heptylcarbamoyl)-alpha-D-glucopyranoside,Nonaethylene glycol monododecyl ether, N-Nonanoyl-N-methylglucamine, N-NonanoylN-methylglucamine, Octaethylene glycol monodecyl ether, Octaethylene glycol-monododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin from Quillaja bark, Span® 20, Span® 40, Span® 60, Span® 65, Span® 80, Span® 85, Tergitol Type 15-S-12, Tergitol Type 15-S-30, Tergitol Type 15-S-5, Tergitol Type 15-S-7, Tergitol Type 15-S-9, Tergitol Type NP-10, Tergitol Type NP-4, Tergitol Type NP-40, Tergitol, Type NP-7 Tergitol Type NP-9, Tergitol Type TMN-10, Tergitol Type TMN-6, Triton X-100 or combinations thereof.

The nanoparticles may then be isolated from cellular debris using centrifugation. In some embodiments, gradient centrifugation, such as using cesium chloride, sucrose and iodixanol, may be used. Other techniques may be used as alternatives or in addition, such as standard purification techniques including, e.g., ion exchange, affinity, and gel filtration chromatography.

For example, the first column may be an ion exchange chromatography resin, such as Fractogel® EMD TMAE (EMD Millipore), the second column may be a lentil (*Lens culinaris*) lectin affinity resin, and the third column may be a cation exchange column such as a Fractogel® EMD SO3 (EMD Millipore) resin. In other aspects, the cation exchange column may be an MMC column or a Nuvia C Prime column (Bio-Rad Laboratories, Inc). Preferably, the methods disclosed herein do not use a detergent extraction column; for example a hydrophobic interaction column. Such a column is often used to remove detergents during purification but may negatively impact the methods disclosed here.

Detergent Exchange

To form detergent-core nanoparticles, the first detergent, used to extract the protein from the host cell is substantially replaced with a second detergent to arrive at the nanoparticle structure. NP-9 is a preferred extraction detergent. Typically, the nanoparticles do not contain detectable NP-9 when measured by HPLC. The second detergent is typically selected from the group consisting of PS20, PS40, PS60, PS65, and PS80. Preferably, the second detergent is PS80.

In particular aspects, detergent exchange is performed using affinity chromatography to bind glycoproteins via their carbohydrate moiety. For example, the affinity chromatography may use a legume lectin column. Legume lectins are proteins originally identified in plants and found to interact specifically and reversibly with carbohydrate residues. See, for example, Sharon and Lis, "Legume lectins—a large family of homologous proteins," FASEB J. 1990 November; 4(14):3198-208; Liener, "The Lectins: Properties, Functions, and Applications in Biology and Medicine," Elsevier, 2012. Suitable lectins include concanavalin A (con A), pea lectin, sainfoin lect, and lentil lectin. Lentil lectin is a preferred column for detergent exchange due to its binding properties. Lectin columns are commercially available; for example, Capto Lentil Lectin, is available from GE Healthcare. In certain aspects, the lentil lectin column may use a recombinant lectin. At the molecular level, it is thought that the carbohydrate moieties bind to the lentil lectin, freeing the amino acids of the protein to coalesce around the detergent resulting in the formation of a detergent core providing nanoparticles having multiple copies of the antigen, e.g., glycoprotein oligomers which can be dimers, trimers, or tetramers anchored in the detergent.

The detergent, when incubated with the protein to form the nanoparticles during detergent exchange, may be present at up to about 0.1% (w/v) during early purification steps.

Typically the influenza detergent core nanoparticles are prepared individually as a monovalent, single strain product. For example, the non-ionic detergent (e.g., PS80) may be about 0.03% to about 0.5%. In a particular aspect, a monovalent drug substance may contain about 1.5 mg/mL of protein measured by A280 and about 0.12% PS80, providing a molar ratio of about 40:1. In particular quadrivalent compositions, the protein concentration may be about 0.48 mg/mL, as measured by single radial immunodiffusion assay (SRID), and the calculated amount of PS80 is about 0.04%.

Detergent exchange may be performed with proteins purified as discussed above and purified, frozen for storage, and then thawed for detergent exchange.

Formation of HaSMaNs

HaSMaNs disclosed herein are produced by incubating the detergent-core nanoparticles with an ISCOM Matrix adjuvant comprising a saponin fraction, cholesterol and a phospholipid.

Figure 35:
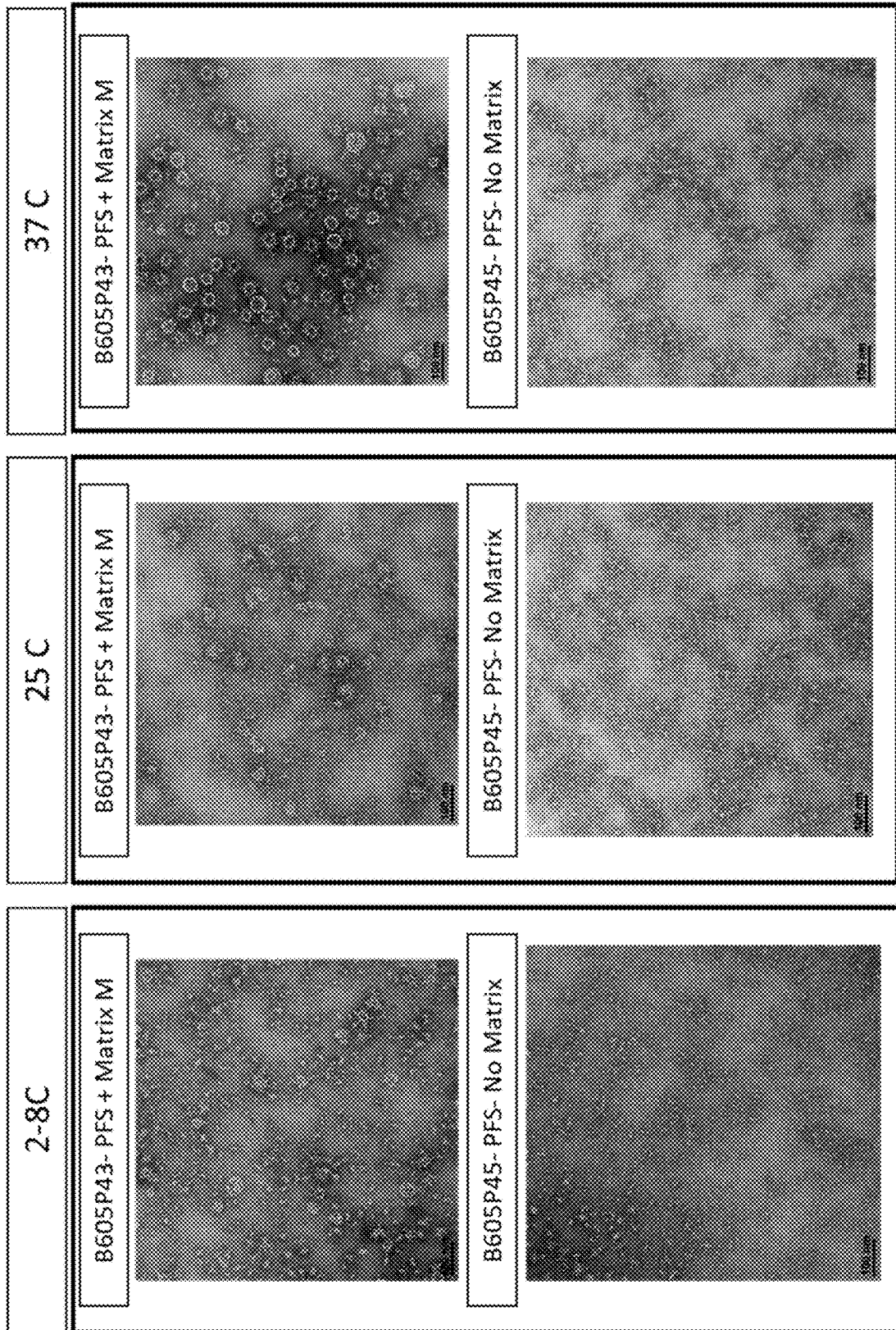

Typically, about 24 to 48 hours at 4° C. or 25° C. incubation is required for formation. Formation of HaSMaNs is promoted by higher temperatures. See e.g. FIGS. 33 and 35. Thus, in particular aspects, formation of HaSMaN occurs by incubation of at least 24 hours at about 25° C. Mixing detergent core nanoparticles with ISCOM Matrix adjuvant shortly prior to administering to a subject—i.e. bedside mix, does not produce HaSMaNs. Longer incubation periods do not negatively impact HaSMaNs formation.

Nanoparticle Influenza HA Proteins

The HA glycoproteins used as influenza antigens may be from any influenza virus strain. Human influenza Type A and Type B viruses cause seasonal epidemics of disease almost every winter in the United States. Influenza Type A viruses are divided into subtypes based on two proteins on the surface of the virus: the hemagglutinin (HA) and the neuraminidase (NA).

The HA protein may be selected from the sub-types H1, H2, H3, H4, H5, H6, H7, H8, H9, H10, H11, H12, H13, H14, H15, H16, H17, and H18. Phylogenetically, the influenza is split into groups. For HA, Group 1 contains H1, H2, H5, H6, H8, H9, H11, H12, H13, H16, H17, and H18 and group 2 contains H3, H4, H7, H10, H14, and H15.

In certain aspects, the influenza nanoparticles are trypsin-resistant nanoparticles produced using neutral pH purification. Trypsin resistance is achieved by neutral pH range of above 6.9 to 8.5 during purification and formulation of the HA nanoparticles. Trypsin resistant influenza glycoproteins and trypsin resistant influenza nanoparticles; and methods of making thereof are described in detail in U.S. application Ser. No. 15/819,962, the contents of which are incorporated herein by reference in its entirety for all purposes.

Modified Antigens

Typically the antigen is a full-length wild type sequence, however, the antigen may be a variation or mutant of the wild type antigen. In certain aspects, the antigen may share identity to a disclosed antigen; for example, the percentage identity may be at least 80%, at least 90%, at least 95%, at least 97%, or at least 98%. Percentage identity can be calculated using the alignment program ClustalW2, available at www.ebi.ac.uk/Tools/msa/clustalw2/. The following default parameters may be used for Pairwise alignment: Protein Weight Matrix=Gonnet; Gap Open=10; Gap Extension=0.1.

Other variants may be used. HA is a homotrimer with each monomer consisting of ~550 amino acid residues. Each monomer of HA has been conceptually divided into three domains: the ectodomain of ~515 residues constitutes the extraviral part of the molecule; a single stretch of 27 residues defines the transmembrane (TM) domain; and ~10 residues constitute the cytoplasmic tail (CT) While some changes may be made to the antigens, formation of both detergent core nanoparticles and HaSMaNs requires an intact transmembrane domain (TM). Thus, in particular examples, a modified HA protein sequence comprises 100% identity (i.e. is wild type) over the TM and CT domains with some flexibility in the remaining ectodomain portion, where identity may be at least 90% or at least 95%. The domains may be identified by homology to the amino acid sequences of the TM domains and CT of Japan/305/57 HA shown in FIG. 1 of Melikyan et al. (Mol Biol Cell. 1999 June; 10(6): 1821-1836) though it should be noted that the boundaries between ectodomain, TM, and CT domains may vary from HA protein to HA protein by up to three amino acids.

Vaccine Stability

Advantageously, the disclosed nanoparticle influenza vaccine formulations are stable and are suitable for long-term storage. The formulations provided herein may be particularly suitable for the co-formulation strategies (i.e., where antigens and matrix adjuvant are combined well in advance of administration; for example, in a pre-filled syringe). As disclosed herein, co-formulation influenza vaccine strategies may provide advantages to clinical practice and may be a cost effective alternative to the currently used bedside mix formulations.

In some embodiments, influenza antigens in the co-formulated vaccine compositions are stable when the compositions are stored up to 12 months. While the vaccine compositions may be stored at 2-8° C. they show excellent stability at 25° C.

The stability of pre-mix (co-formulated) formulations can be evaluated by methods and protocols known in the art. The stability can be measured by the levels of degradation of vaccine antigens and by immunogenicity of the vaccines. The stability can be examined by evaluating the thermostability of viral antigens in the vaccines.

The stability of vaccine formulations at room temperature (25° C.) for extended period is advantageous for cost effective vaccine strategies, especially for areas where cold chain distribution and storage may be limited. As stated in the WHO's guidelines for evaluating the stability of vaccines, controlled temperature chain during manufacturing, distribution, and storage is important to ensure the efficacy of vaccines ("Guidelines on the stability evaluation of vaccines for use in a controlled temperature chain; available at www.who.int/biologicals/WHO_CTC_first_draft_22_Dec_2014_amended.pdf).

Figure 36:
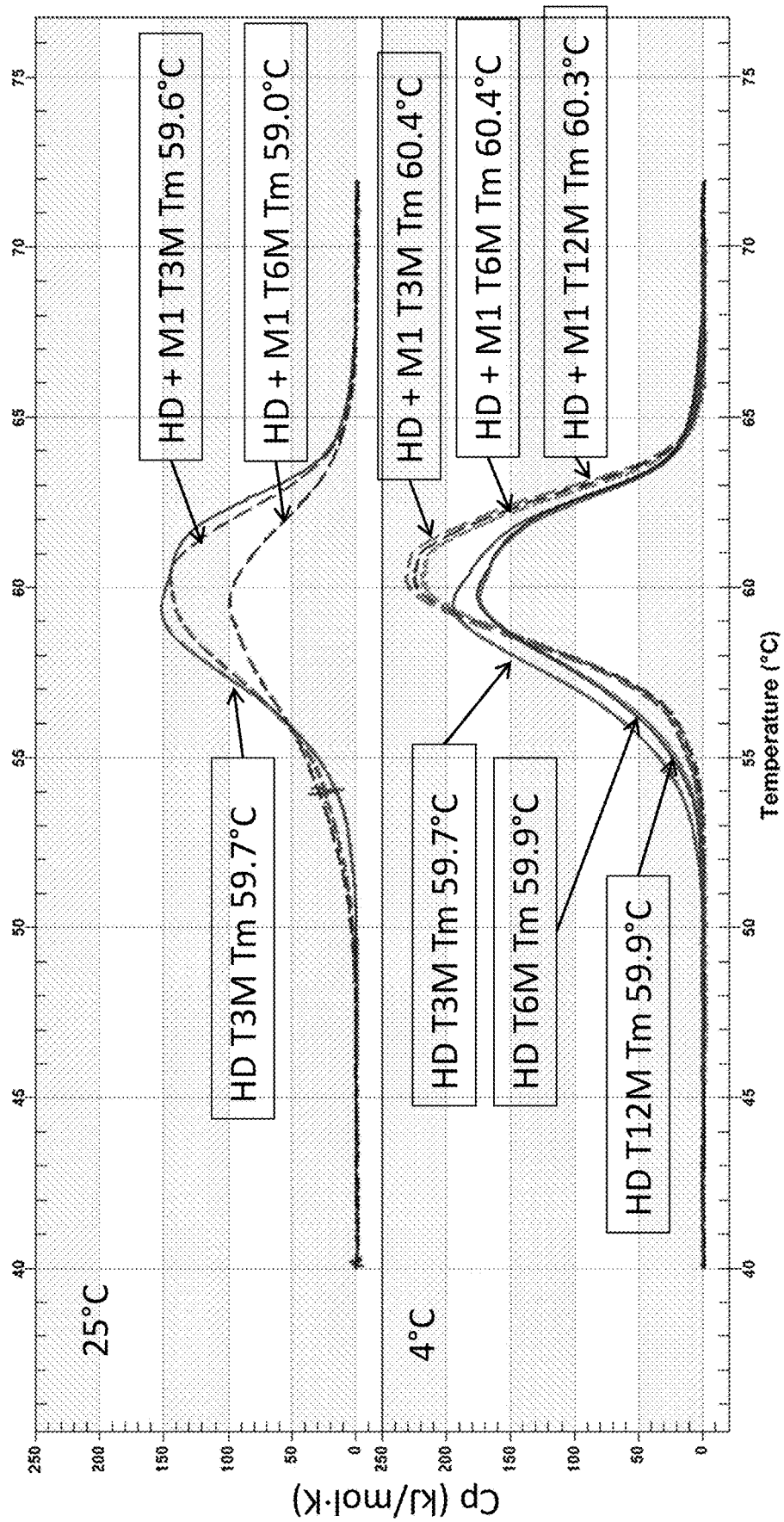

Without being bound by theory, it is thought that the HaSMaN structure may contribute to the stability of co-formulated vaccine formulations. (see FIG. 36 showing greater thermal stability in the presence of Matrix adjuvant; i.e., showing that HaSMaNs particles have greater stability than detergent-core only formulations). Mixing detergent-core nanoparticles with Matrix M to provide HaSMaNs provides vaccine compositions with an increase of about 0.5° C. to about 1.0° C. (as measured by differential scanning calorimetry) compared to vaccine compositions containing only detergent-core nanoparticles.

This improved thermal stability contributes to vaccine shelf-life. In particular aspects, the vaccine formulations may be stable for up to 6 months, or up to 12 months. A tested sample is considered to be "stable" in the context of this disclosure if the HAI titer against the tested sample after 12 months storage at 2-8° C. is not statistically different from a freshly prepared sample; and if Single Radial Immunodiffusion (SRID) assays give a value of at least about 70% after 12 months storage at 2-8° C. Analysis of the statistical significance of HAI titer measurements was done in the following manner. The geometric mean titer (GMT) and associated 95% confidence intervals (CI) were calculated by group. The mean of the log 10 transformed titer measurements by HAI were compared between groups using the Tukey HSD analysis with JMP13 software. A p-value <0.05 indicates a statistically significant difference between two compared groups.

Vaccine Compositions

Compositions disclosed herein may be used either prophylactically or therapeutically. The disclosure includes methods for preventing infection of influenza virus. The methods involve administering to the subject a therapeutic or prophylactic amount of the immunogenic compositions of the disclosure. Preferably, the pharmaceutical composition is a vaccine composition that provides a protective effect. In aspects, the protective effect may include amelioration of a symptom associated with infection in a percentage of the exposed population. For example, the composition may prevent or reduce one or more influenza symptoms selected from: fever fatigue, muscle pain, headache, and sore throat, compared to an untreated subject.

The vaccine compositions may contain various excipients, pharmaceutically acceptable buffers, and the like. For example, the pharmaceutically acceptable buffers in the vaccine compositions may contain one or more of sodium phosphate, sodium chloride, histidine, arginine hydrochloride and trehalose. Sodium phosphate may be present at about 10 mM to about 50 mM, about 15 mM to about 30 mM. In particular cases, about 25 mM sodium phosphate is present. Histidine may be present in a range from about 0.1% (w/v) to about 2.5% (w/v); for example, histidine may be present at about 0.1% (w/v), about 0.5% (w/v), about 0.7% (w/v), about 1% (w/v), about 1.5% (w/v), about 2% (w/v), or about 2.5% (w/v).

Sodium chloride may be in a range from about 50 mM to about 300 mM. Typically, sodium chloride, when present in a composition, is about 150 mM.

Arginine hydrochloride may be present at about 50 mM to about 200 mM, about 80 mM to about 150 mM, or about 100 mM to about 180 mM. In particular cases, about 100 mM arginine hydrochloride is present.

Trehalose may be present in a range from about 1% to about 10%; for example, at about 1%, about 2%, about 3%, about 4%, about 5%, about 6%, about 7%, about 8%, about 9%, or about 10%.

The pH range for influenza vaccine composition is typically near neutral and are maintained above pH 6.9 during purification and in the compositions. For example, the pH of buffers and compositions may be about pH 7.2 to about pH 7.8, more preferably about 7.2 to about 7.5. In particular aspects, the pH is about pH 7.5. pH levels below 6.9 are avoided because they negatively impact the stability of the HA structure.

Adjuvants

In certain embodiments, the compositions disclosed herein may be combined with one or more adjuvants to enhance an immune response. In other embodiments, the compositions are prepared without adjuvants, and are thus available to be administered as adjuvant-free compositions.

The immunogenicity of a particular composition may be enhanced by the use of non-specific stimulators of the immune response, known as adjuvants. Effective amounts of adjuvants have long been used to promote a generalized increase in immunity against antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this disclosure.

While various adjuvants may be included, the HaSMaNs are produced using an ISCOM matrix adjuvant, which retains its adjuvant effective activity after administration to a subject. Accordingly, in some aspects, no additional adjuvant may be added into a formulation. As noted above, this formulation approach, allows for the preparation of pre-filled syringes containing vaccine without the requirement for bed-side mixing of antigen with adjuvant.

Saponin Adjuvants for Matrix

ISCOM matrix is prepared using saponin fractions. Saponins are glycosides derived from the bark of the *Quillaja saponaria* Molina tree. Typically, saponin is prepared using a multi-step purification process resulting in multiple fractions. As used, herein, the term "a saponin fraction from *Quillaja saponaria* Molina" is used generically to describe a semi-purified or defined saponin fraction of *Quillaja saponaria* or a substantially pure fraction thereof.

Saponin Fractions

Several approaches for producing saponin fractions are suitable. Fractions A, B, and C are described in U.S. Pat. No. 6,352,697 and may be prepared as follows. A lipophilic fraction from Quil A, a crude aqueous *Quillaja saponaria* Molina extract, is separated by chromatography and eluted with 70% acetonitrile in water to recover the lipophilic fraction. This lipophilic fraction is then separated by semi-preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Other saponin fractions have been described. Fractions B3, B4 and B4b are described in EP 0436620. Fractions QA1-QA22 are described EP03632279 B2, Q-VAC (NorFeed, AS Denmark), *Quillaja saponaria* Molina Spikoside (Isconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9.

The saponin fractions described herein and used for forming adjuvants are often substantially pure fractions; that is, the fractions are substantially free of the presence of contamination from other materials. In particular aspects, a substantially pure saponin fraction may contain up to 40% by weight, up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, or up to 0.1% by weight of other compounds such as other saponins or other adjuvant materials.

Other saponin fractions, such as QS-7 and QS-21 fractions, their production and their use is described in U.S. Pat. Nos. 5,057,540; 6,231,859; 6,352,697; 6,524,584; 6,846,489; 7,776,343, and 8,173,141. These fractions may be used in the methods and compositions disclosed herein.

Matrix Particles

Matrix particle adjuvants disclosed herein may be used to produce HaSMaNs or used as discrete particles for their adjuvant properties. An ISCOM matrix comprises at least one saponin fraction and a lipid. The lipid is at least a sterol, such as cholesterol. In particular aspects, the lipid is a phospholipid. The ISCOM matrix complexes may also contain one or more other immunomodulatory (adjuvant-active) substances, not necessarily a glycoside, and may be produced as described in EP0436620B1.

The saponin fraction may be fraction A, fraction B, or fraction C of *Quillaja saponaria*, a semipurified preparation of *Quillaja saponaria*, a purified preparation of *Quillaja saponaria*, or any purified sub-fraction e.g., QA 1-21.

The matrix particles may contain mixtures of saponin fractions or a particle may be formed using only one saponin fraction. Compositions disclosed herein may contain multiple particles wherein each particle contains only one saponin fraction. That is, certain compositions may contain one or more different types of ISCOM-matrix where each individual particle contains one saponin fraction from *Quillaja saponaria* Molina, wherein the saponin fraction in one particle is different from the saponin fraction in the other complex particles.

In particular aspects, one type of saponin fraction or a crude saponin fraction may be integrated into one ISCOM matrix particle and another type of substantially pure saponin fraction, or a crude saponin fraction, may be integrated into another ISCOM matrix particle. A composition or vaccine may comprise at least two types of complexes or particles each type having one type of saponins integrated into physically different particles.

In the compositions, mixtures of ISCOM matrix particles may be used in which one saponin fraction *Quillaja saponaria* Molina and another saponin fraction *Quillaja saponaria* Molina are separately incorporated into different ISCOM matrix complex particles and/or ISCOM complex particles.

The ISCOM matrix that each have one saponin fraction may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of an ISCOM matrix containing a first saponin fraction with the remaining portion made up by an ISCOM matrix containing a different saponin fraction. In some aspects, the remaining portion is one or more ISCOM matrix particle containing only one saponin fraction. In other aspects, the ISCOM matrix particle may contain more than one saponin fraction.

In preferred compositions, the saponin fraction in a first ISCOM matrix is Fraction A (a "Fraction A Matrix") and the saponin fraction in a second ISCOM matrix or ISCOM complex particle is Fraction C (a "Fraction C Matrix"). Thus, preferred compositions comprise, as an adjuvant, a Fraction A Matrix adjuvant and a Fraction C Matrix adjuvant. The amounts of each Matrix in the composition may vary. For example, the amount of Fraction A Matrix may be about 80% (w/w), about 85% (w/w), about 90% (w/w), about 92% (w/w), or about 95% (w/w) with the remainder Fraction C Matrix. An example of a suitable 85:15 Fraction A Matrix and Fraction C Matrix combination (referred to herein as Matrix M or Matrix MD may be sourced from Novavax AB, Uppsala, Sweden as Matrix-M™.

In some aspects, Matrix-M may be used as an adjuvant in the compositions provided herein. In some aspects, Matrix-M may be used as the only adjuvant in the nanoparticle influenza vaccine composition provided herein.

In some embodiments, the amount of Matrix-M per dose administered may range from about 20 µg to about 140 µg; for example about 20 µg, about 30 µg, about 40 µg, about 50 µg, about 60 µg, about 70 µg, about 75 µg, about 80 µg, about 90 µg, about 100 µg, about 110 µg, about 120 µg, about 130 µg, or about 140 µg. In particular aspects the adjuvant may be present at about 50 µg to about 75 µg.

Other Adjuvants

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/Tween® 80 emulsion. In other preferred aspects, Alum such as 2% Alhydrogel ($Al(OH)_3$) is used. In some aspects, the adjuvant may be a paucilamellar lipid vesicle; for example, Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant (see, U.S. Pat. Nos. 5,629,021, 6,387,373, and 4,911,928.

Administration and Dosage of Nanoparticle Vaccine Compositions

Compositions disclosed herein may be administered via a systemic route or a mucosal route or a transdermal route or directly into a specific tissue. As used herein, the term "systemic administration" includes parenteral routes of administration. In particular, parenteral administration includes subcutaneous, intraperitoneal, intravenous, intramuscular, or intrasternal injection. Typically, the compositions are administered by intramuscular injection. In particular aspects, the compositions may be administered mucosally. As used herein, the term "mucosal administration" includes oral, intranasal, intravaginal, intra-rectal, and intra-tracheal.

The compositions may be administered to a subject in need thereof, typically a human.

Compositions may be administered on a single dose schedule or a multiple dose schedule. Multiple doses may be used in a primary immunization schedule or in a booster immunization schedule. In a multiple dose schedule the various doses may be given by the same or different routes e.g., a parenteral prime and mucosal boost, a mucosal prime and parenteral boost, etc. In some aspects, a follow-on boost dose is administered about 2 weeks, about 3 weeks, about 4 weeks, about 5 weeks, or about 6 weeks after the prior dose.

In some embodiments, at least one strain out of the four strains in the quadrivalent influenza vaccine compositions is a type A strain. For example, a quadrivalent influenza vaccine can contain three type A strains and one type B strain.

The total amount of the influenza HA in the vaccine compositions may range from of about 25 µg to about 200 µg, about 30 µg to about 150 µg, about 50 µg to about 100 µg, about 45 µg to about 180 µg, about 60 µg to about 190 µg, or about 100 µg to about 200 µg. In certain embodiments, the amount of the influenza HA protein in the vaccine composition may be in the range of about 5 µg per strain to about 80 µg per strain, about 10 µg per strain to about 75 µg per strain, about 15 µg per strain to about 70 µg per strain, about 20 µg per strain to about 65 µg per strain, about 25 µg per strain to about 60 µg per strain, about 30 µg per strain to about 55 µg per strain, about 35 µg per strain to about 50 µg per strain, about 15 µg per strain to about 60 µg per strain. Advantageously, the compositions exhibit stability up to 9 to 12 months such that the amount remaining, as measured by SRID, is a substantial percentage of the initial amount; for example, at least about 70%, at least about 75%, or at least about 80% of the initial amount.

In some embodiments, the disclosure provides co-formulation (i.e., prefilled syringes or pre-mix) strategies for nanoparticle influenza vaccine compositions. Typical influenza vaccine administration strategies currently being utilized are bedside mix formulations. That is, vaccine compositions and adjuvants are stored separately and are mixed prior to administration. Pre-mix, co-formulation, or prefilled syringe strategies for influenza vaccine are less common due to the concerns of the stability of the influenza antigens and their subsequent immunogenic capabilities. The present disclosure provides nanoparticle influenza vaccine compositions that can be pre-mixed and stored in advance. The disclosed vaccination strategies and formulations may improve the efficiency of vaccination and may reduce the risks of bedside mixing errors, while maintaining the overall safety and immunogenicity.

Immunogenicity of the Nanoparticle Influenza Vaccine

The present disclosure provides methods of preventing influenza infection. Immunogenicity of the nanoparticle influenza vaccines disclosed herein may be determined using suitable approaches, including performing HAI assays or by measuring neutralizing antibodies. In some embodiments, the immunogenicity of the nanoparticle influenza vaccines may be compared to a commercially available influenza vaccine composition. As used herein, "commercially available influenza vaccine composition" can be any influenza vaccine compositions that are available for medical uses. For example, the commercially available influenza vaccine composition can be formulated for a trivalent or a quadrivalent injection. In some aspects, the formulation for an injection can comprise the inactivated form of the virus. In another example, the commercially available influenza vaccine composition can be formulated for a nasal spray. In some aspects, the formulation for a nasal spray can comprise attenuated or weakened forms of the virus.

The composition disclosed herein provide non-inferior immune responses compared to other vaccines, in particular commercially available vaccines, including Afluria Quadrivalent, Fluarix Quadrivalent, FluLaval Quadrivalent, Fluzone Quadrivalent, Flucelvax Quadrivalent, Fluzone Intradermal Quadrivalent, Afluria, Fluvirin, Fluad, Fluzone High-Dose, Flublok Quadrivalent, Flublok, and FluMist Quadrivalent.

Advantageously, the compositions disclosed herein induce neutralizing antibodies that bind to a strain that has drifted (i.e. undergone slight mutation) relative to the sequence used in the virus within the same sub-type of influenza. In particular aspects, one, two, three four, or all of the strains used in the compositions induce neutralizing antibodies against one drifted strain, against two drifted strains, against three drifted strains, against four drifted strains, or against five drifted strains. Without being bound by theory it is thought that the presence of the Matrix adjuvant in the compositions promotes exposure of additional antigens, providing broadened protection against the drifted strain. Similarly, formation of the HaSMaNs following incubation with Matrix adjuvant with the sub-type A HA proteins is thought to contribute to this process.

Importantly, the HaSMaNs are at least as immunogenic as detergent-core nanoparticles. For instance, as shown in Table 6 below, the HAI titer against A/Michigan at day 35 for 1.5 pre-mix formulations was about 538 at 25° C., whereas the HAI titer against A/Michigan for 1.5 bedside mix formulations was about 453 at 25° C. In another example shown in Table 8, the HAI titer against A/Hong Kong at day 35 for 1.5 μg pre-mix formulations was about 538 at 25° C., whereas the HAI titer against A/Michigan for 1.5 μg bedside mix formulations was about 494 at −60° C. Similar immunogenicity among pre-mix formulations and bedside mix formulations further suggests that pre-mix formulations are stable at room temperature. In addition, the present pre-mix formulations stored at room temperature surprisingly can have similar immunogenicity compared with bedside mix formulations that are incubated at −60° C.

Containers

A variety of containers may be used to store and transport the pre-mix formulations, including syringes for single administrations and plastic ampules. In some instances, plastic ampules can be manufactured using the blow-fill-seal manufacturing technique or method. In general, the blow-fill-seal (BFS) manufacturing method includes extruding a plastic material (e.g., resin) to form a parison, which is then placed into a mold and cut to size. A filling needle or mandrel is then used to inflate the plastic, which in turn, results in a hollow ampule that substantially conforms to the shape of the mold. Once inflated, a desired volume of liquid can be injected into the ampule, the filling needle or mandrel can be removed, and the ampule can be sealed. Accordingly, BFS can be an automated process that can be performed in a sterile environment without direct human intervention.

In some instances, the ability to aseptically manufacture sterile ampules containing a desired liquid can make BFS manufactured ampules particularly well suited for the pharmaceutical industry. BFS technology, however, has not been compatible with all pharmaceutical liquids, products, etc. For example, some known BFS manufacturing methods include delivering the liquid or product into the ampule while the plastic is still relatively hot, which can result in adverse effects to temperature sensitive liquids and/or products such as vaccines, biologics, etc. Advances in cool BFS technology, however, have increased the variety of suitable products, liquids, etc. allowing some vaccines, biologics, and/or other temperature sensitive pharmaceuticals to be contained in BFS ampules.

In some instances, a BFS ampule can have a size, shape, and/or configuration that is at least partially based on a desired use and/or a desired pharmaceutical liquid or dosage that the ampule is configured to contain. For example, some known BFS ampules can include a pierce through top, a twist-off top, a top including a male or female luer, and/or the like. Some known BFS ampules can have a size and/or shape based on volume of the liquid or dosage configured to be disposed therein. In addition, some known BFS ampules can be manufactured in a strip of multiple, temporarily connected ampules, which can increase manufacturing, packaging, and/or storing efficiencies and/or the like.

All patents, patent applications, references, and journal articles cited in this disclosure are expressly incorporated herein by reference in their entireties for all purposes.

EXAMPLES

Example 1: Purification of HA Nanoparticles

HA proteins from a single strain were expressed in Sf9 cells via baculovirus infection and allowed to grow for 48-96 hours before harvesting. The HA proteins were then harvested by detergent extraction and turned into detergent core nanoparticles during purification. Briefly, the TMAE column was pre-equilibrated with buffer composed of 25 mM Tris, pH 8.0, 1.5M sodium chloride, 0.02% NP9. Sample was loaded at <90 cm/hr (24 min residence time) and then washed with EQ buffer (25 mM Tris, pH 8.0, 50 mM sodium chloride or 81 mM sodium chloride (A, B strains respectively), 0.02% NP-9). The purified sample was then eluted using 1.5 CV EQ buffer.

For A strains, Nanofiltration was performed for the product from the TMAE column followed by application onto a Lentil lectin affinity chromatography column pre-equilibrated with buffer composed of 25 mM Tris, 50 mM and 107 mM Sodium Chloride (for A and B strains respectively), 0.02% (w/v) NP-9, pH 8.0 for 3CV (Flow Rate: 150 cm/h). Sample was loaded at 4 min resident time. After loading, washing was performed with 3CV of the Lentil Lectin equilibration buffer. The product was eluted with 25 mM Sodium Phosphate, pH 7.5, 200 mM Sodium Chloride, 500 mM Methyl-α-D-Mannopyranoside, 0.01% (w/v) PS80, pH 7.5 by collecting 2CV's at 75 cm/hr and 8 minute residence time.

For B strains, TMAE column product was further purified using Capto Blue column. The column was equilibrated with 25 mM Tris, pH 8.0, 107 mM Sodium Chloride, 0.02% (w/v) NP-9 followed by loading the TMAE product with a flow rate of 225 cm/hr at 4 minute residence time and collection with 2CV of equilibration buffer. Nanofiltration was performed for the product from the Capto Blue column followed by application onto a Lentil lectin affinity chromatography column pre-equilibrated with buffer composed of 25 mM Tris, 50 mM and 107 mM Sodium Chloride (for A and B strains respectively), 0.02% (w/v) NP-9, pH 8.0 for 3CV (Flow Rate: 150 cm/h). Sample was loaded at 4 min resident time. After loading, washing was performed with 3CV of the Lentil Lectin equilibration buffer. The product was eluted with 25 mM Sodium Phosphate, pH 7.5, 200 mM Sodium Chloride, 500 mM Methyl-α-D-Mannopyranoside, 0.01% (w/v) PS80, pH 7.5 by collecting 2CV's at 75 cm/hr and 8 minute residence time.

The Lentil Lectin products for both A and B strains were concentrated to target HA concentration and then buffer exchanged to the final Drug Substance formulation buffer. Concentration and buffer exchange was performed by ultrafiltration and diafiltration.

Example 2—SDS PAGE Analysis

Figure 4:
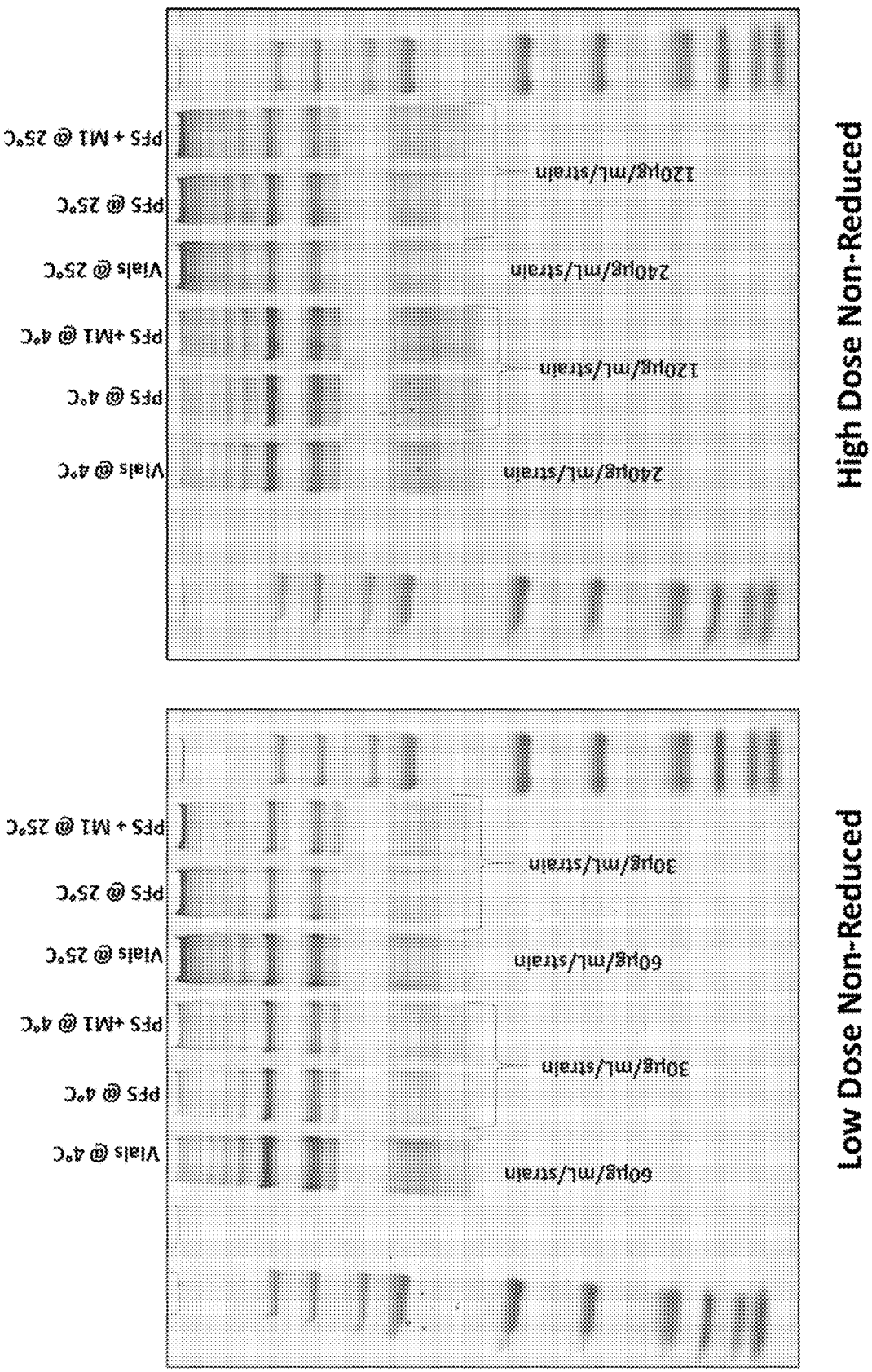
FIG. 4 illustrates non-reduced SDS-PAGE gel images for influenza antigens of high dose and low dose bedside vial formulations (240 µg/mL/strain and 60 µg/mL/strain); and PFS formulations (120 µg/mL/strain and 30 µg/mL/strain) with or without Matrix M at 4° C. and 25° C. at 3-month time point.

To evaluate the stability of co-formulating the Quad-NIV and ISCOM matrix adjuvant (Matrix M) in pre-filled syringes and to understand the physical, chemical and biological properties of such a vaccine, formulations were prepared as shown in Table 1 below. The tested vaccine compositions were assigned to three groups: (1) glass bedside vials containing HA antigens only, (2) pre-filled syringes (PFS) containing HA vaccine antigens co-formulated with Matrix M1, and (3) PFS containing HA vaccine antigens. Glass vials for the bedside mix and the PFS were purchased commercially (Schott).

TABLE 1

Comparison Study of Bedside Vial Formulations and PFS Formulations

| | | Concentration (μg/mL) | |
|---|---|---|---|
| Containers | Dose | HA/Strain | Matrix M1 |
| Bedside Vials | Low (LD) | 60 | N/A |
| | High (HD) | 240 | N/A |
| PFS (Co-Formulation) | Low (LD) | 30 | 100 |
| | High (HD) | 120 | 100 |
| PFS (No Matrix M) | Low (LD) | 30 | N/A |
| | High (HD) | 120 | N/A |

FIG. 2 shows reduced SDS-PAGE gel images showing bands of proteins from either bedside vials stored at 4° C.; or pre-filled syringes (PFS), with or without Matrix M1 stored at 4° C. At all the time points tested, the band pattern of proteins from PFS was similar to the band pattern of the proteins from bed side vials, indicating that the proteins in the PFS were at least as stable as the proteins in the bedside vials. The presence or the absence of Matrix M did not change the band patterns among the PFS groups nor did storage for 6 months or even 12 months. LD bedside vial groups and LD PFS groups also had consistently similar band patterns at 4° C., although the LD groups had weaker band patterns compared with their HD cohorts at the same time point.

FIG. 3 shows band patterns of proteins from PFS or bedside vials stored at 4° C., examined on a non-reduced SDS-PAGE gel and reduced SDS-PAGE gel. The results show that the protein band patterns were similar for all groups even on a non-reduced gel, further showing that the proteins in the PFS were similar the proteins in the bedside vials at time zero.

In addition, protein stability for the bedside vial groups; and PFS groups with or without Matrix M, stored at 4° C. or 25° C. for 3 months, was examined using non-reduced SDS-PAGE assays (FIG. 4). Bands with higher molecular weights tended to appear in some of the groups that were stored at the higher temperature (25° C.) compared to those that were stored at the lower temperature (e.g., 4° C.). Stronger expression of the proteins was also observed in groups stored in lower temperatures. The results show that the proteins in the PFS were at least as stable as the proteins in the bedside vials even after an extended period of storage, such storage for 3 months.

These data show that PFS co-formulation vaccine strategies would be feasible with respect to the stability. Storage of PFS co-formulation vaccines at both 4° C. and 25° C. is feasible. The presence of Matrix M1 and the duration of the storage time (for example, 3 months) did not negatively impact the stability of vaccine formulations, confirming that formation of the HaSMaNs does not interfere with protein stability over extended periods of time.

Example 3—SRID Analysis

Figure 5:
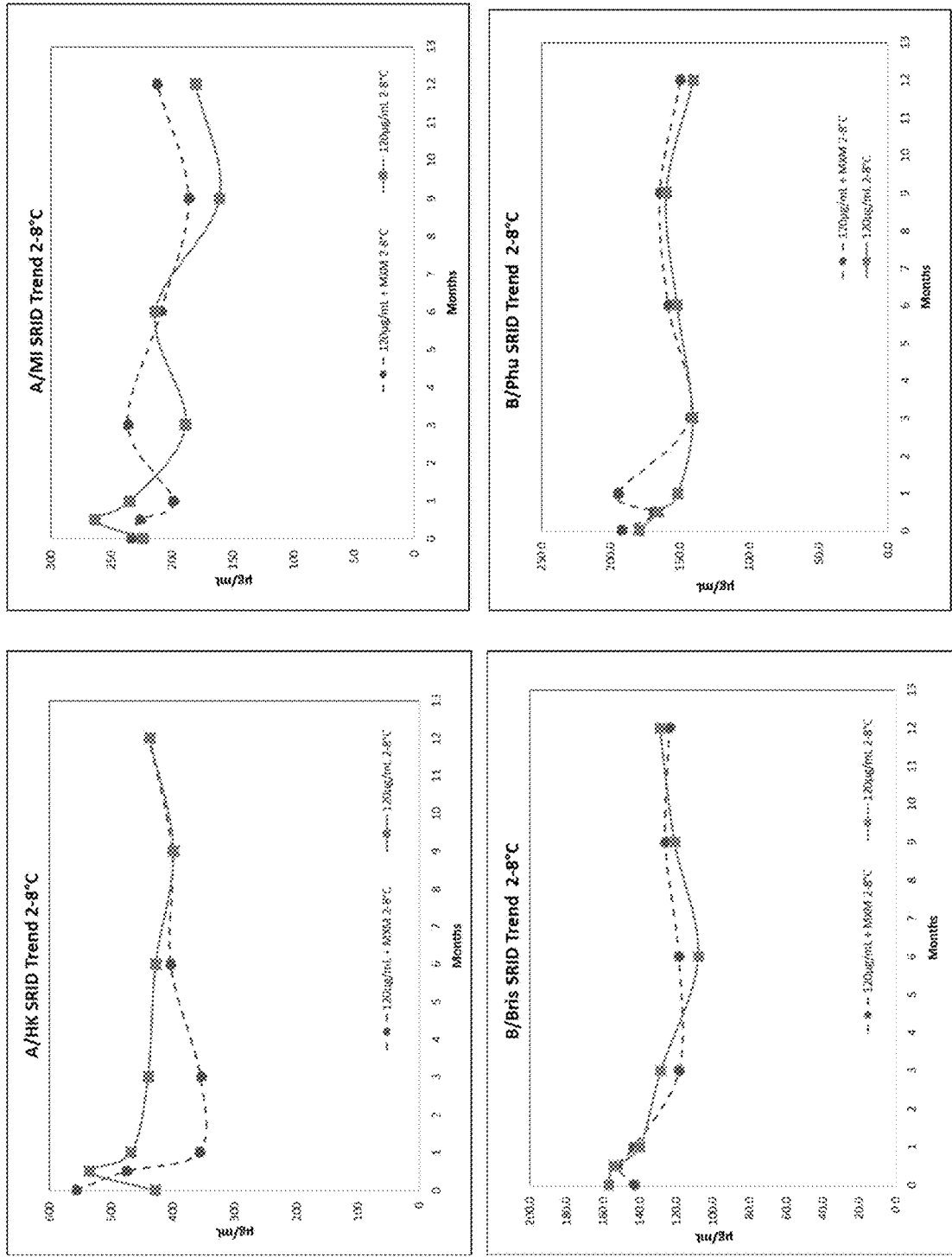
FIG. 5 illustrates single radial immunodiffusion assay (SRID) results of A/Hong Kong, A/Michigan, B/Brisbane, and B/Phuket strains for a dose of 120 µg/mL/strain PFS formulations either with or without Matrix M at 2-8° C. at T=0, 2 weeks, 1 month, 3 months, 6 months, 9 months and 12 months. Abbreviations in the figure are MXM: Matrix M; HK: Hong Kong; MI: Michigan; Bris: Brisbane; Phu: Phuket.
Figure 6:
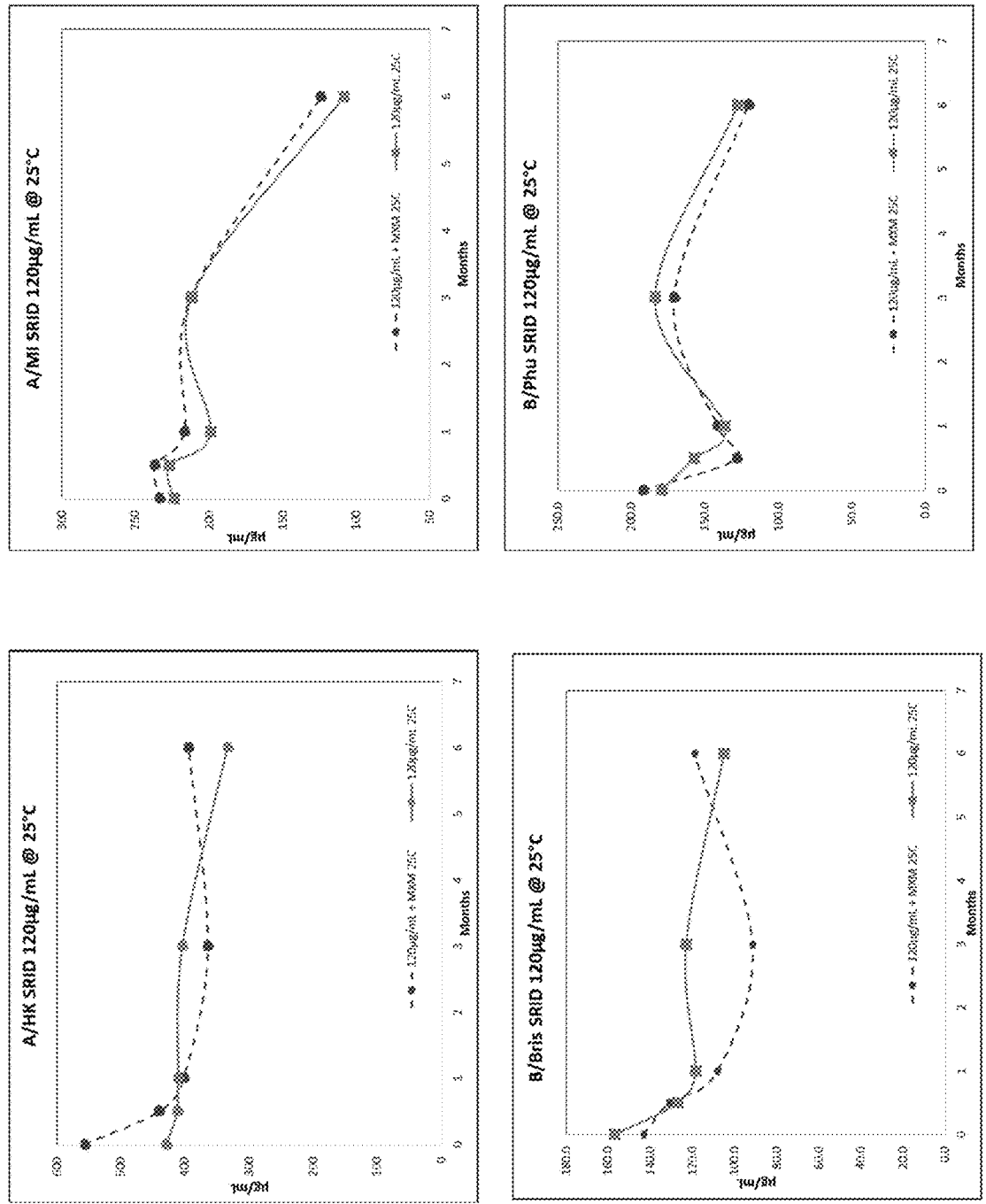
FIG. 6 illustrates SRID results of A/Hong Kong, A/Michigan, B/Brisbane, and B/Phuket strains for a dose of 120 µg/mL/strain PFS formulations either with or without Matrix M at 25° C. at T=0, 2 weeks, 1 month, 3 months, and 6 months.
Figure 7:
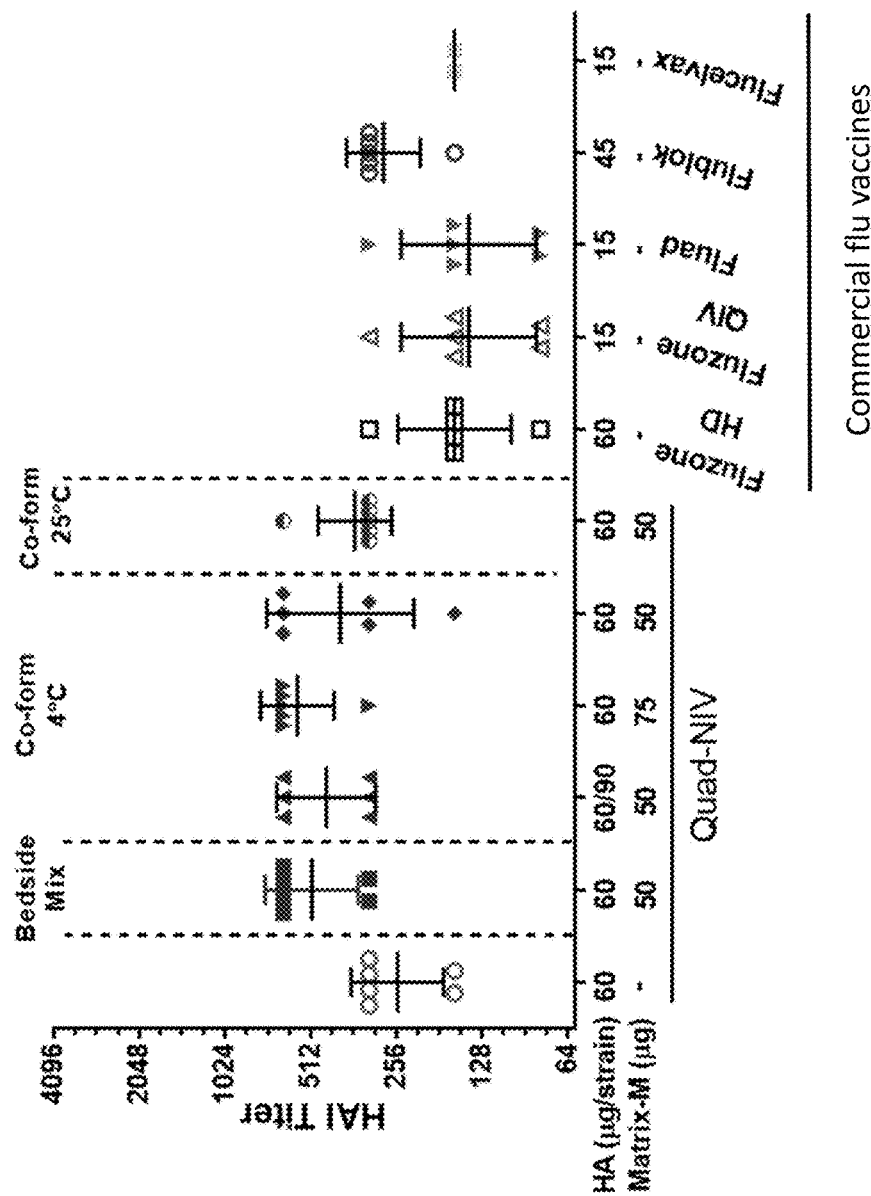
FIG. 7 illustrates hemagglutination inhibition antibody response in mice administered with Quad-NIV co-formulations; or bedside mix formulations with or without Matrix M, compared to commercial influenza vaccines against A/Hong Kong/4801/2014. The antibody response is presented as the HAI titers. Abbreviations in the figure are HAI: hemagglutination inhibition; HA: hemagglutinin; Co-form: co-formulations; Quad-NIV: quadrivalent nanoparticle influenza vaccine; QIV: quadrivalent influenza vaccine.
Figure 8:
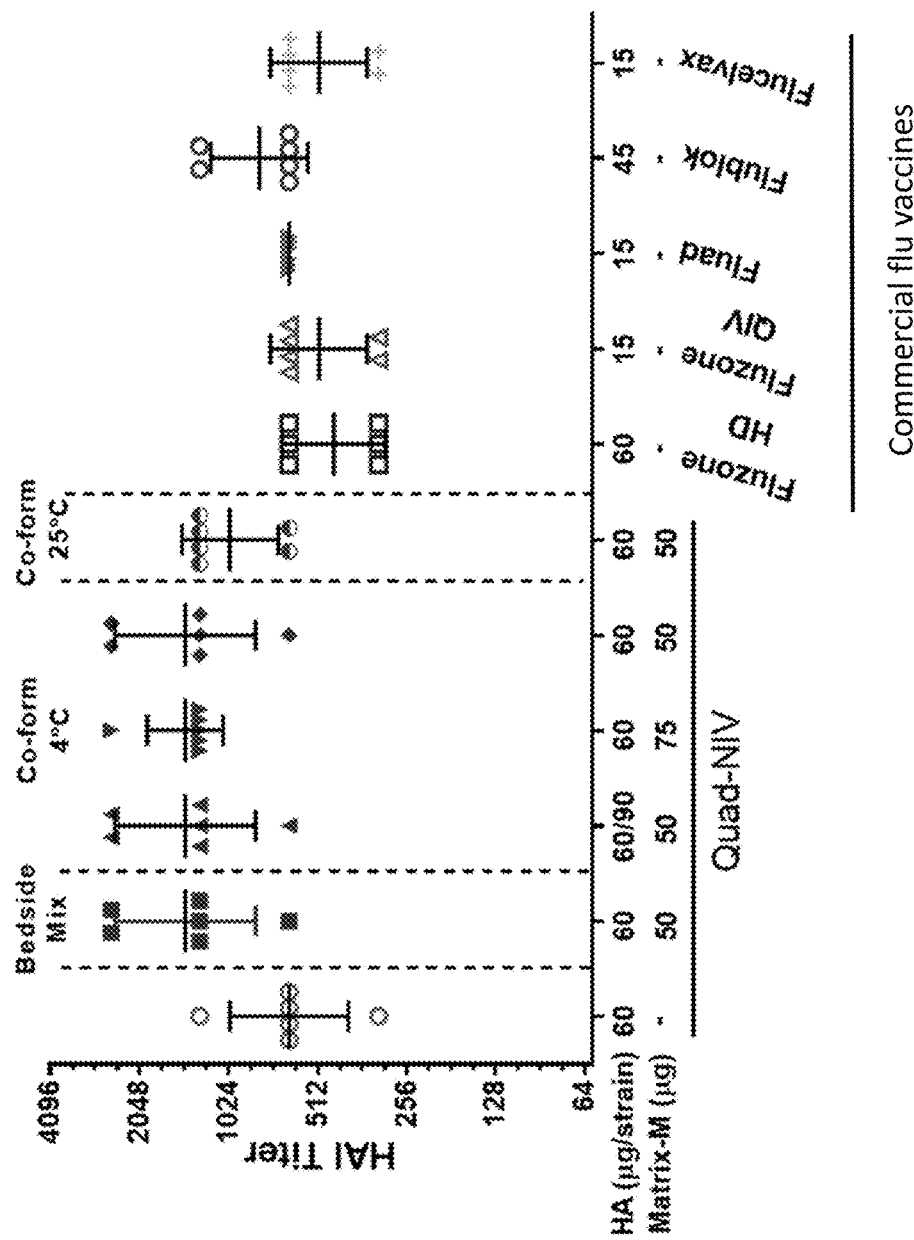
FIG. 8 illustrates hemagglutination inhibition antibody response against A/Michigan/45/2015 in mice administered with Quad-NIV co-formulations; or bedside mix formulations with or without Matrix M, compared to commercial influenza vaccines.
Figure 9:
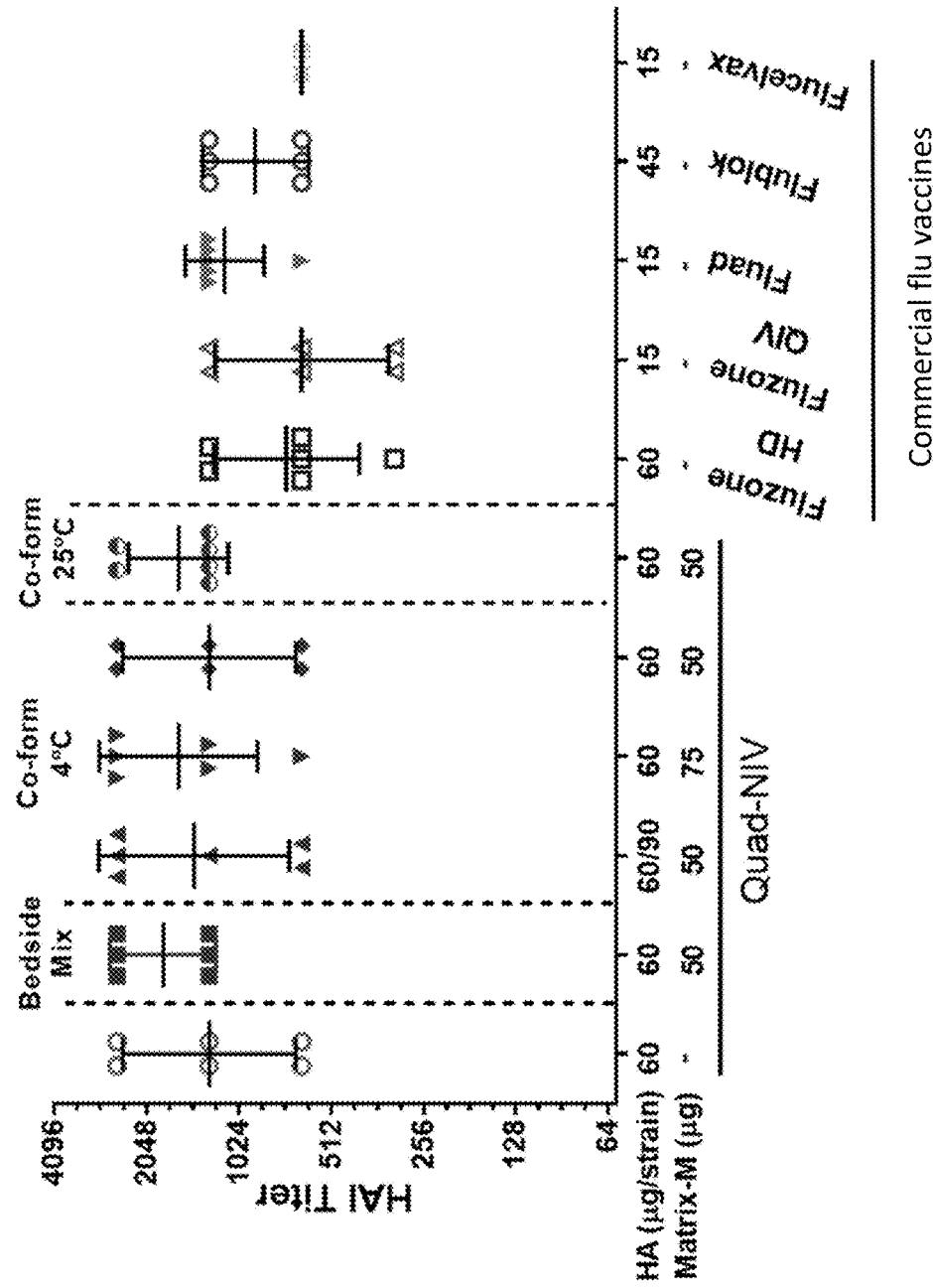
FIG. 9 illustrates hemagglutination inhibition antibody response against B/Brisbane/60/2008 in mice administered with Quad-NIV co-formulations; or bedside mix formulations with or without Matrix M, compared to commercial influenza vaccines.
Figure 10:
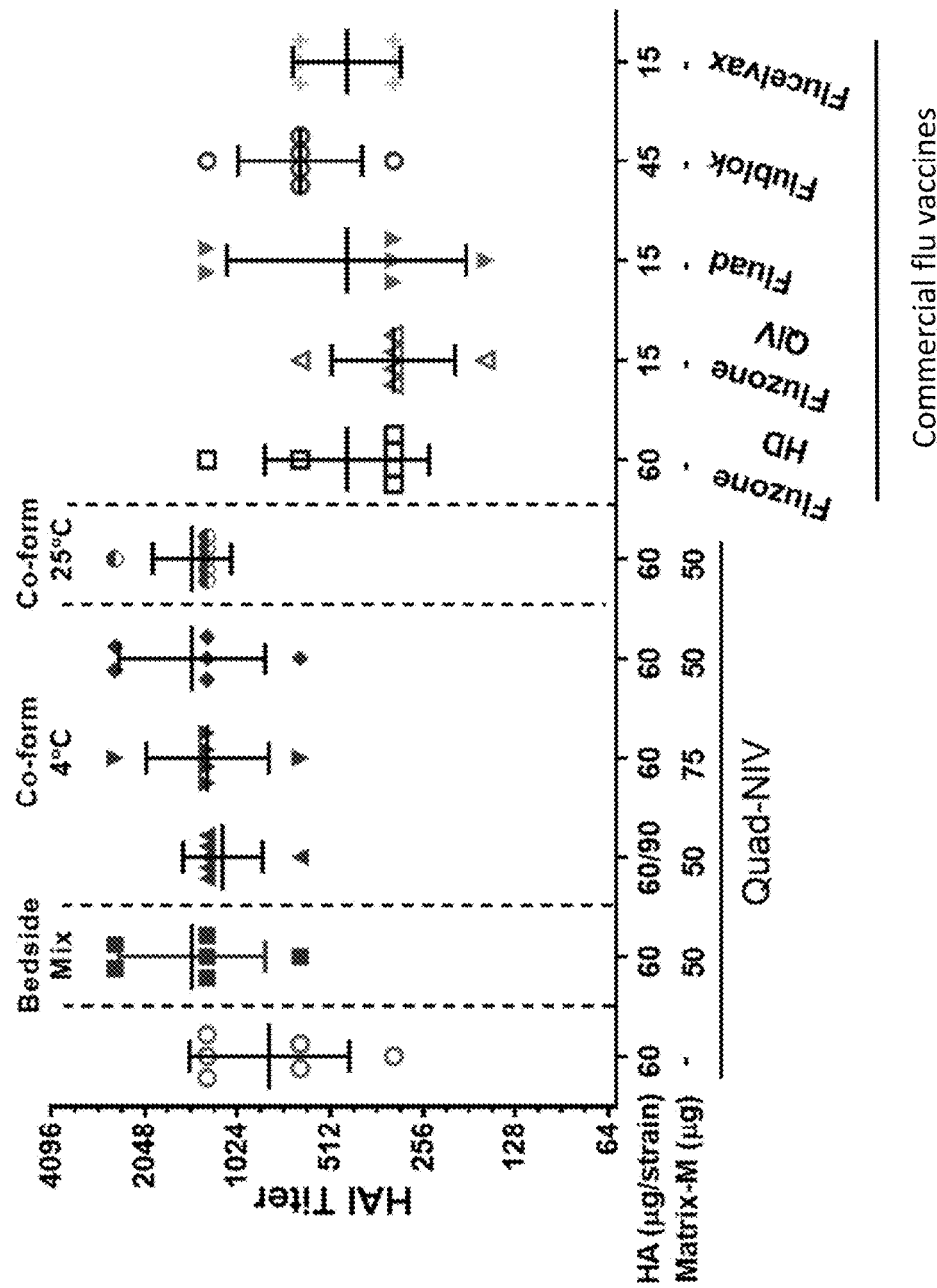
FIG. 10 illustrates hemagglutination inhibition antibody response against B/Phuket/3073/2013 in mice administered with Quad-NIV co-formulations; or bedside mix formulations with or without Matrix M, compared to commercial influenza vaccines.

Protein stability was tested by conducting the SRID assay for various influenza A strains and B strains formulated in PFS groups. The SRID assay was performed at 2-8° C. (e.g., 4° C.) at T=0, 2 weeks, 1 month, 3 months, 6 months, 9 months and 12 months; and at 25° C. at T=0, 2 weeks, 1 month, 3 months and 6 months. FIGS. 5 and 6 show the SRID data for 120 µg/mL PFS formulations containing A/Hong Kong, A/Michigan, B/Brisbane or B/Phuket, with or without 100 µg/mL Matrix M at 2-8° C. (FIG. 5) and 25° C. (FIG. 6).

The SRID immunoreactivity results of PFS with Matrix M were similar to, or better than, the SRID immunoreactivity results of PFS without Matrix M. The data show that the general trend of immunoreactivity with time upon storage at 25° C. does not noticeably differ from the results observed at 4° C. The absence of notable changes in vaccine immunoreactivity indicates that the Quad-NIV PFS formulations are stable at various temperatures for at least up to 6 months. The stability of Quad-NIV PFS formulations at room temperature (25° C.) provides advantageously cost effective vaccine strategies because the PFS formulations would not need long-term refrigeration or be limited to low temperature handling. These data further show that mass production of stable, pre-mixed vaccines (comprising influenza antigens and Matrix M) long before vaccination at clinics is a feasible approach.

Example 4—Comparative Immunogenicity Study of Quad-NIV and Commercial Flu Vaccines in Ferrets Ferret studies were performed to compare the immunogenicity of various test vaccine strategies (bedside and co-formulations) with the commercially available flu vaccines.

TABLE 2

Immunogenicity Comparative Study for Quad-NIV and Commercial Vaccine in Ferrets

| Group (n = 6) | Vaccine | HA dose (µg/strain) | Matrix-M1 dose (µg) | Formulation | Immunization | Blood Draw[#] |
|---|---|---|---|---|---|---|
| 1 | NVX Quad-NIV | 60 | N/A | N/A | Day 0, 21 | Day −1, 21, 42 |
| 2 | NVX Quad-NIV | 60 | 50 | Bed-side Mix | Day 0, 21 | Day −1, 21, 42 |
| 3 | NVX Quad-NIV | 60/90* | 50 | Co-form (4° C.) | Day 0, 21 | Day −1, 21, 42 |
| 4 | NVX Quad-NIV | 60 | 75 | Co-form (4° C.) | Day 0, 21 | Day −1, 21, 42 |
| 5 | NVX Quad-NIV | 60 | 50 | Co-form (4° C.) | Day 0, 21 | Day −1, 21, 42 |
| 6 | NVX Quad-NIV | 60 | 50 | Co-form (25° C.) | Day 0, 21 | Day −1, 21, 42 |
| 7 | Fluzone HD (TIV) | 60 | — | N/A | Day 0, 21 | Day −1, 21, 42 |
| 8 | Fluzone (QIV) | 15 | — | N/A | Day 0, 21 | Day −1, 21, 42 |
| 9 | Fluad (TIV) | 15 | MF59C.1 | N/A | Day 0, 21 | Day −1, 21, 42 |
| 10 | Flublok (QIV) | 45 | — | N/A | Day 0, 21 | Day −1, 21, 42 |
| 11 | Flucelvax (QIV) | 15 | — | N/A | Day 0, 21 | Day −1, 21, 42 |

*Each B strain dose was 90 µg; and each A strain dose was 60 µg.
[#]The results depicted in FIGS. 7-10 correspond to day 42.

For the Quad-NIV formulations, A/Michigan/45/2015-H1N1 strains, A/Hong Kong/4801/2014-H3N2 strains, B/Brisbane/60/2008 strains, B/Phuket/3073/2013 strains were used. For Fluzone HD (TIV; Sanofi Pasteur), A/Michigan/45/2015-H1N1, A/HongKong/4801/2014-H3N2, and B/Brisbane/60/2008 were used. For Fluzone HD (QIV; Sanofi Pasteur), A/Michigan/45/2015-H1N1, A/HongKong/4801/2014-H3N2, B/Brisbane/60/2008, and B/Phuket/3073/2013 were used. For Fluad (TIV; Seqirus), A/Singapore/GP1908/2015 (A/Michigan/45/2015-H1N1 like), A/HongKong/4801/2014-H3N2 and B/Brisbane/60/2008 were used. For Flublok (QIV; Protein Sciences), A/Michigan/45/2015-H1N1, A/HongKong/4801/2014-H3N2, B/Brisbane/60/2008 and B/Phuket/3073/2013 were used. For Flucelvax (QIV; Seqirus), A/Singapore/GP1908/2015 (A/Michigan/45/2015-H1N1 like), A/Singapore/GP2050/2015 (A/Hong Kong/4801/2014-H3N2 like), B/Hong Kong/259/2010 (B/Brisbane/60/08-like), and B/Utah/9/2014 (B/Phuket/3073/2013-like) were used.

The ferrets were immunized at day 0 and day 21 of the study. Blood was drawn on the day before the start of the study, on day 21 and on day 42 of the study. HAI assay was conducted using human red blood cells to evaluate the immunogenicity of tested formulations in the ferrets. The experimental protocols are known in the art and are discussed above. The following HAI reagents were used in the assay as the reference influenza antigens in the VLP forms: (1) A/Michigan 45/15 (BV #001), (2) A/HongKong/4801/14 (BV #1808), (3) B/Bris/60/08 (BV #714), (4) B/Phuket/3073/13 (BV #1659), (5) A/Switzerland/9715293/13 (BV #1660), (6) A/Singapore/2016 (BV #2165), (7) A/Texas/50/2012 (BV #1324), (8) A/Victoria/36/11 (BV #1577) and (9) A/Perth/16/09. Methods of making the influenza antigen VLPs are disclosed, for example, in the U.S. patent application Ser. No. 15/901,000, herein incorporated by reference in its entirety for all purposes.

All commercially available influenza vaccines had lower HAI titers compared with all Quad-NIV formulations in the presence of Matrix M, regardless of the dosing regimens, the types of formulations (i.e., bedside and co-formulations). See FIG. 7 (A/Hong Kong/4801-2014), FIG. 8 (A/Michigan/45/2015), FIG. 9 (B/Brisbane/60/2008) and FIG. 10 (B/Phuket/3073/2013).

In summary, Quad-NIV formulations can elicit more robust immunogenic effects in ferrets for all tested influenza strains disclosed herein compared with the commercial vaccines, while the differences are more significant with the presence of Matrix M in the formulations. The Quad-NIV co-formulations (pre-mixed) containing HaSMaN had similar immunogenicity compared with the Quad-NIV bedside formulations. Among the co-formulation groups, formulations stored at 4° C. and at 25° C. generally had very similar immunogenicity.

Example 5—Immunogenicity Assessments of Quadrivalent Nanoparticle Influenza Vaccines Stored at 4° C.

Table 3 shows the mouse study design for examining the immunogenicity and the stability of pre-mixed PFS vaccine formulations and bedside mixed vaccines. PFS formulations were stored at 4° C. for 3 months. For bedside mixed vaccines, the viral antigens were stored at −60° C. for 3 months and mixed with the Matrix M adjuvant right before administration.

Immunizations were intramuscularly administered on day 0 and day 21. Blood samples were collected on the day before the study began and again on day 42 of the study (or day 21 post-second immunization) for immunogenicity analyses. The immunogenicity was determined based on Hemagglutination inhibition (HAI) responses to the following influenza A and B strains: (1) A/Hong Kong/4801/2014; (2) A/Michigan/45/2015; (3) B/Brisbane/60/2008; and (4) B/Phuket/3073/2013. HAI were measured as described in Manual for the laboratory diagnosis and virological surveillance of influenza (World Health Organization 2011, Accessed Feb. 15, 2018, at: www.who.int/influenza/gisrs_laboratory/manual_diagnosis_surveillance_influenza/en/, which are incorporated by references for those disclosures.

Figure 11:
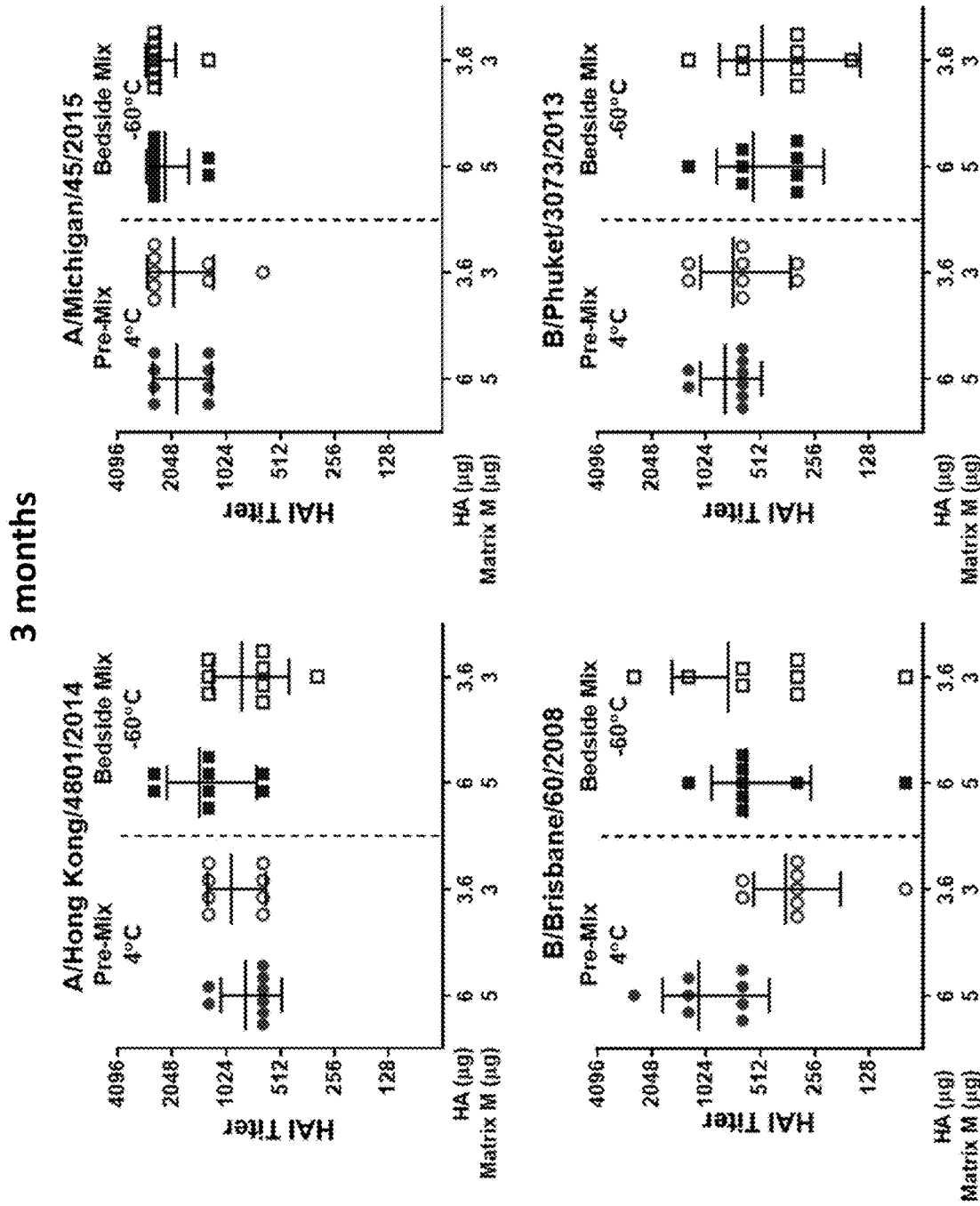
FIG. 11 illustrates the hemagglutination inhibition antibody response in mice administered with Quad-NIV pre-mix or bedside mix formulations with Matrix M against A/Hong Kong/4801/2014, A/Michigan/45/2015, B/Brisbane/60/2008, and B/Phuket/3073/2013. PFS formulations were stored at 4° C. for 3 months. For the bedside mixed vaccines, the viral antigen was stored at −60° C. for 3 months and mixed with the Matrix M adjuvant right before administration. The antibody response was presented as the HAI GMT titers. 95% lower control limit and 95% upper control limit were used for the GMT results. Abbreviations in the figure are HAI: hemagglutination inhibition; HA: hemagglutinin; GMT: geometric mean titer; LCL: lower control limit; UCL: upper control limit.
Figure 12:
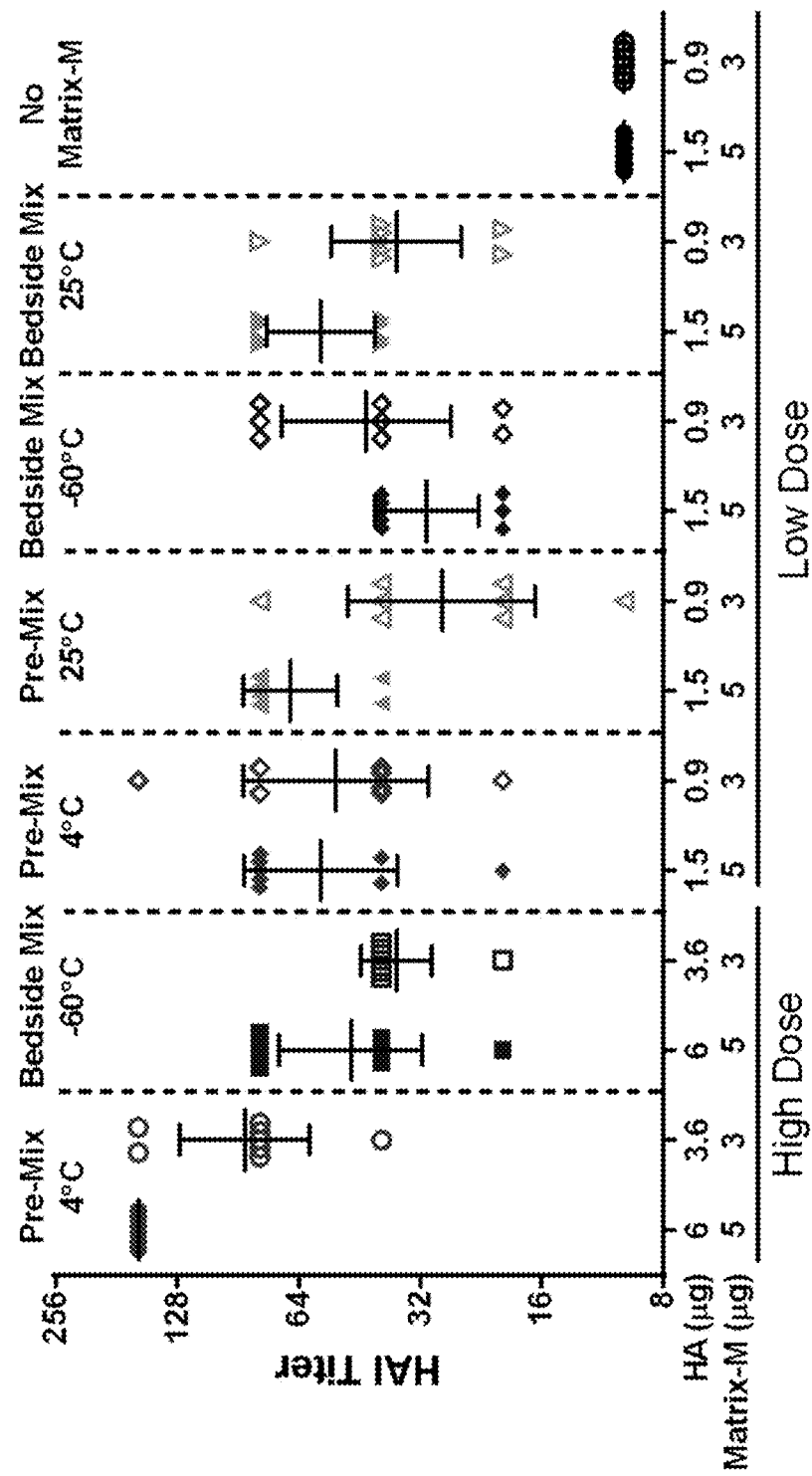
FIG. 12 illustrates hemagglutination inhibition antibody response against A/Michigan strains in mice administered with Quad-NIV co-formulations; or bedside mix formulations with or without Matrix M (100 µg/mL) at 21 days. The pre-mixed Quad-NIV co-formulations were stored at the indicated temperatures for 6 months.
Figure 13:
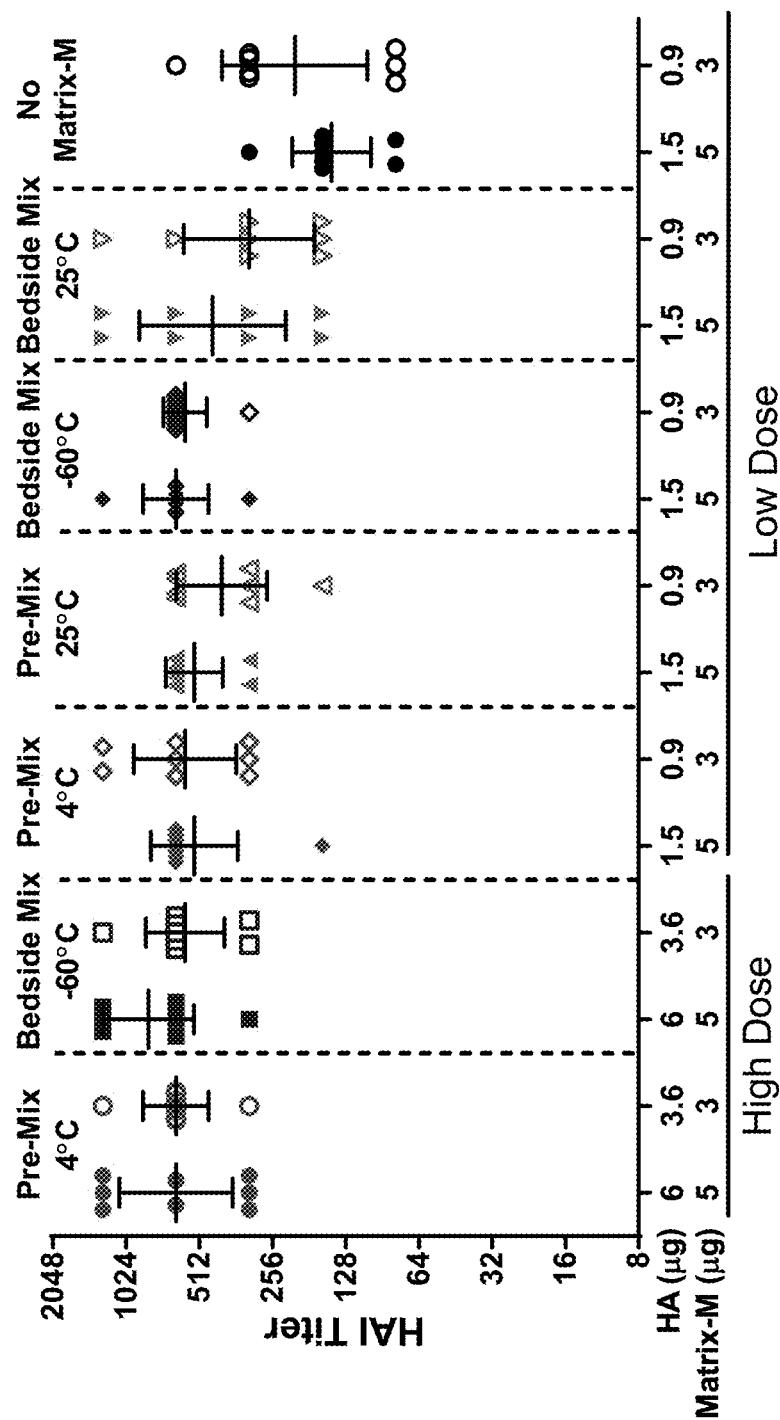
FIG. 13 illustrates hemagglutination inhibition antibody response against A/Michigan strain in mice administered with Quad-NIV co-formulations; or bedside mix formulations with or without Matrix M (100 µg/mL) at 35 days. The pre-mixed Quad-NIV co-formulations were stored at the indicated temperatures for 6 months.
Figure 14:
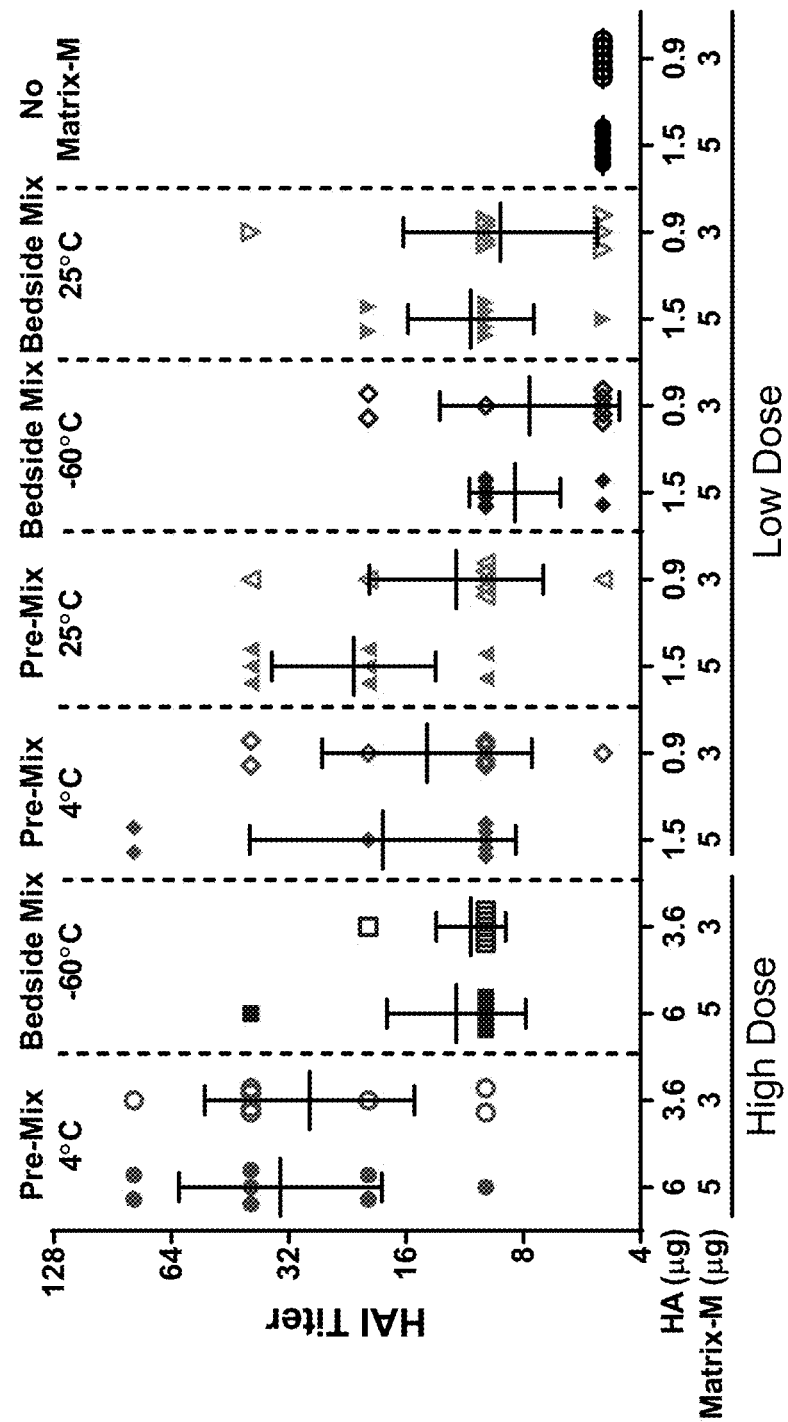
FIG. 14 illustrates hemagglutination inhibition antibody response against A/Hong Kong/4801/2014 in mice administered with Quad-NIV co-formulations; or bedside mix formulations with or without Matrix M (100 µg/mL) at 21 days. The pre-mixed Quad-NIV co-formulations were stored at the indicated temperatures for 6 months.
Figure 15:
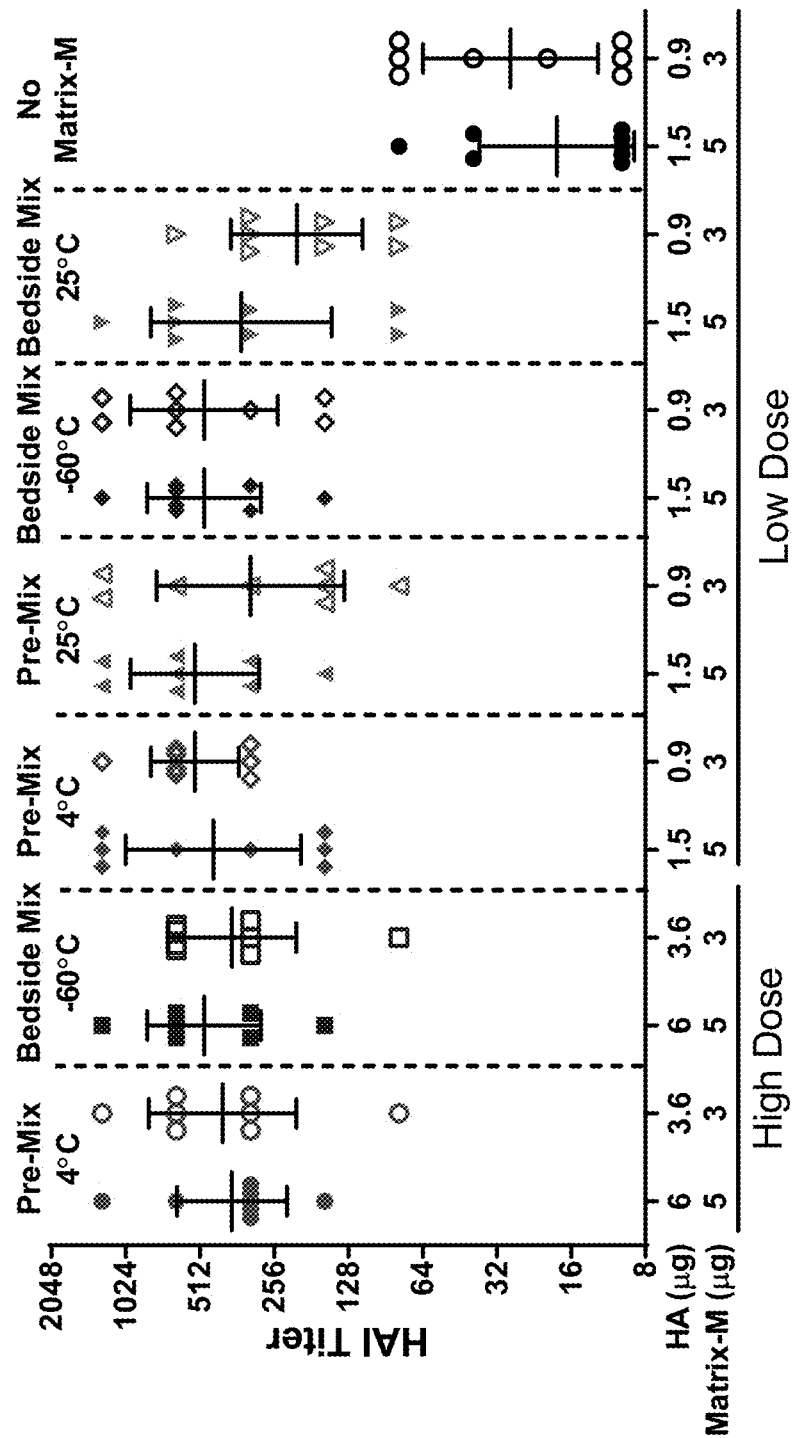
FIG. 15 illustrates hemagglutination inhibition antibody response against A/Hong Kong strain in mice administered with Quad-NIV co-formulations; or bedside mix formulations with or without Matrix M (100 µg/mL) at 35 days. The pre-mixed Quad-NIV co-formulations were stored at the indicated temperatures for 6 months.
Figure 16:
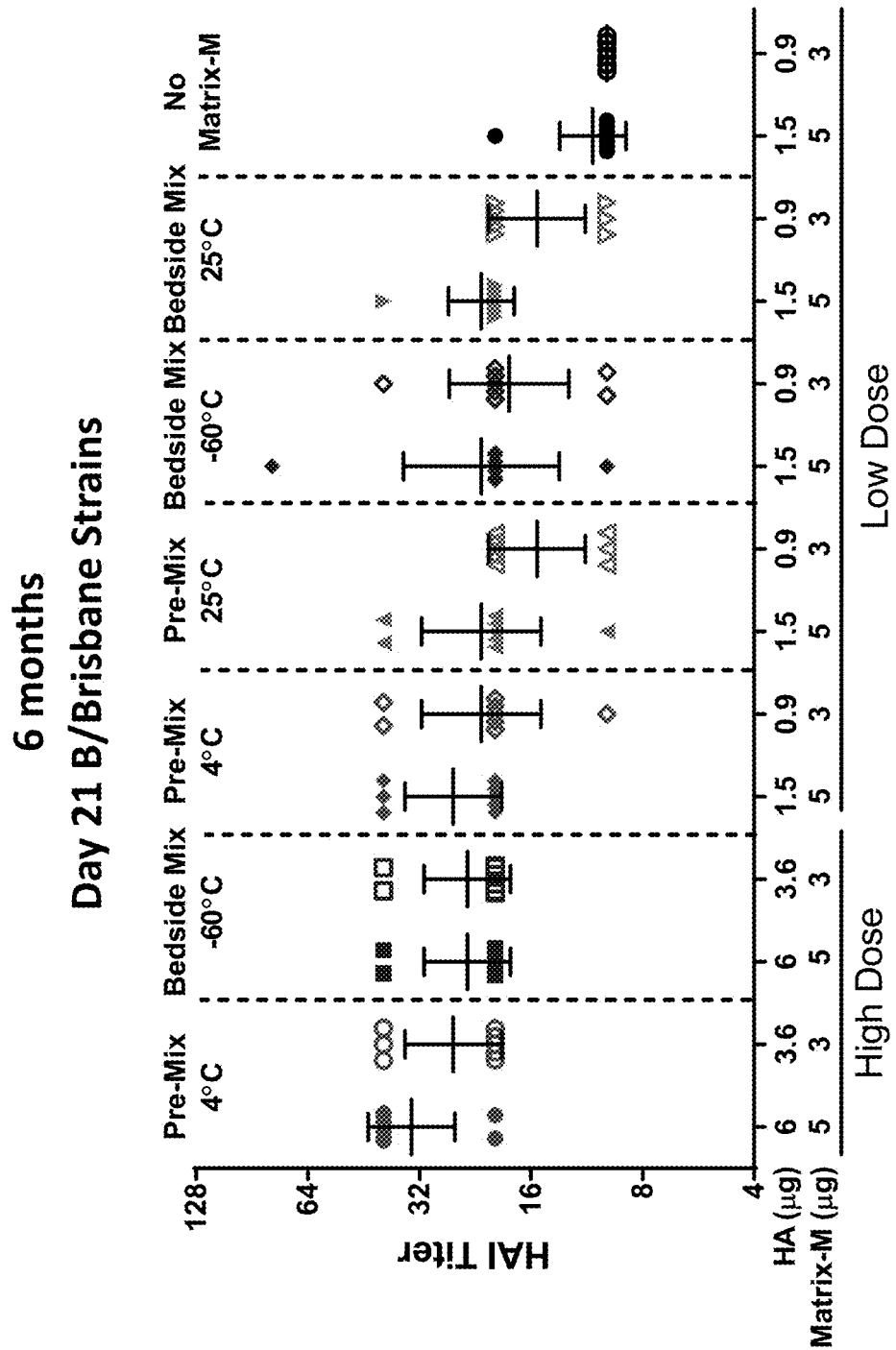
FIG. 16 illustrates hemagglutination inhibition antibody response against B/Brisbane strain in mice administered with Quad-NIV co-formulations; or bedside mix formulations with or without Matrix M (100 µg/mL) at 21 days. The pre-mixed Quad-NIV co-formulations were stored at the indicated temperatures for 6 months.
Figure 17:
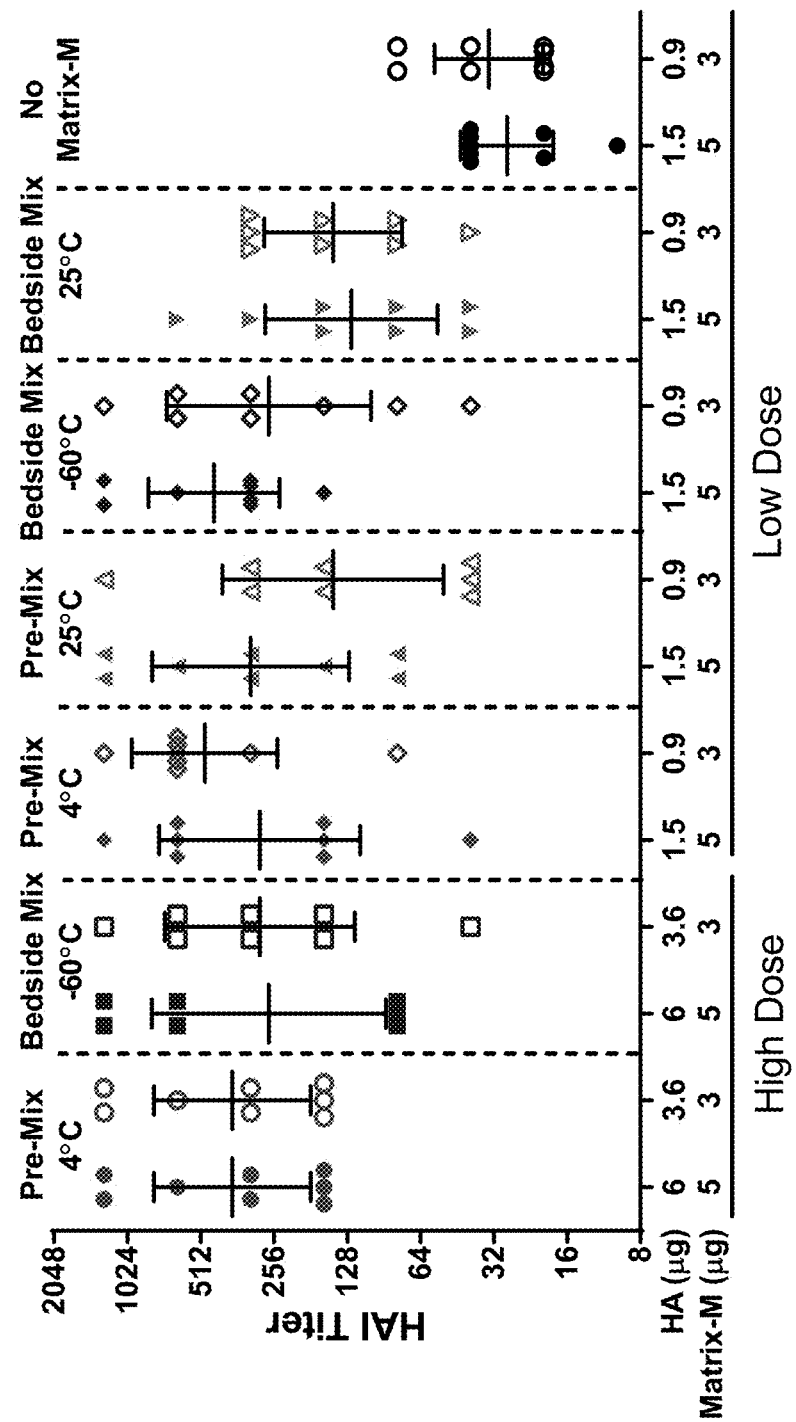
FIG. 17 illustrates hemagglutination inhibition antibody response against B/Brisbane strain in mice administered with Quad-NIV co-formulations; or bedside mix formulations with or without Matrix M (100 µg/mL) at 35 days. The antibody response was presented as the HAI titers. The pre-mixed Quad-NIV co-formulations were stored at the indicated temperatures for 6 months.
Figure 18:
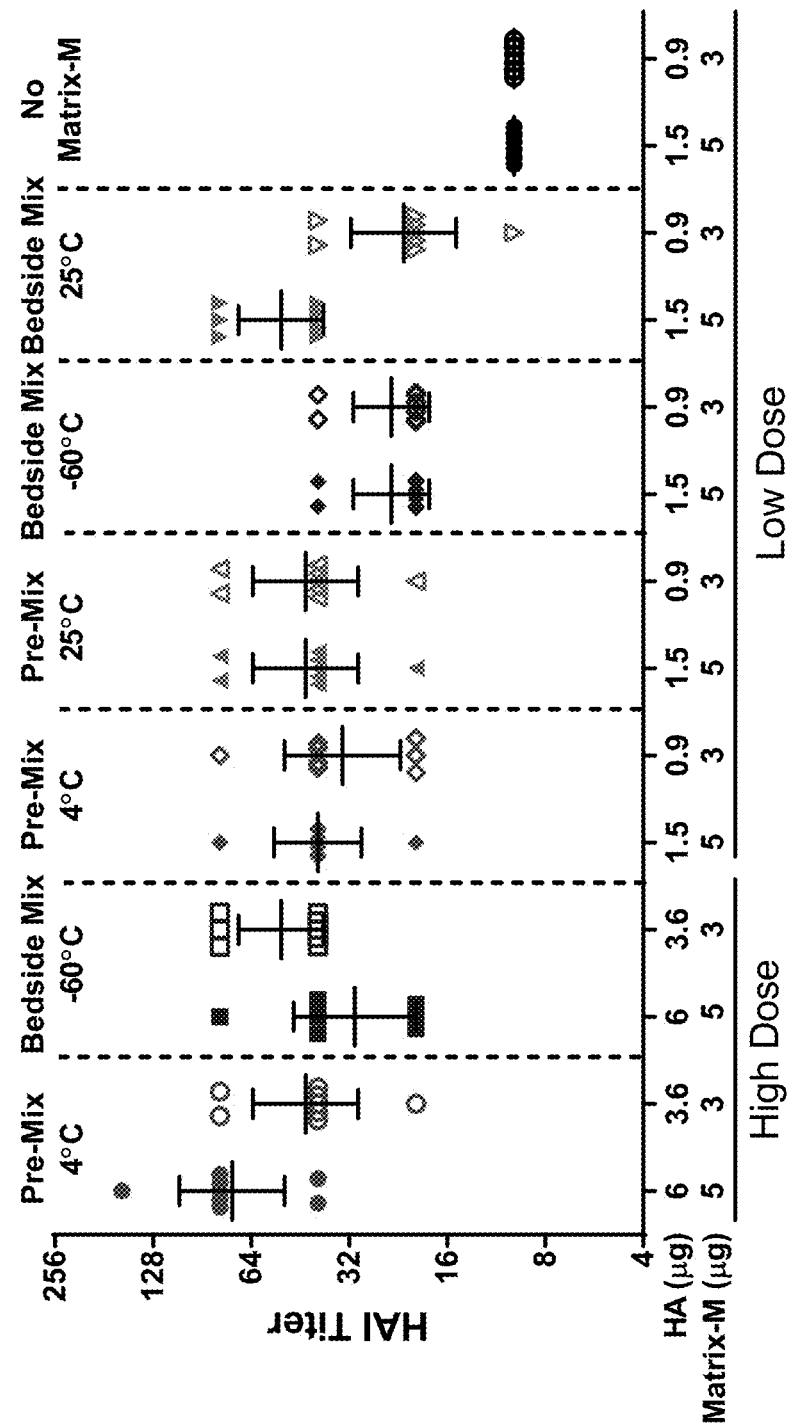
FIG. 18 illustrates hemagglutination inhibition antibody response against B/Phuket strain in mice administered with Quad-NIV co-formulations; or bedside mix formulations with or without Matrix M (100 µg/mL) at 21 days. The pre-mixed Quad-NIV co-formulations were stored at the indicated temperatures for 6 months.
Figure 19:
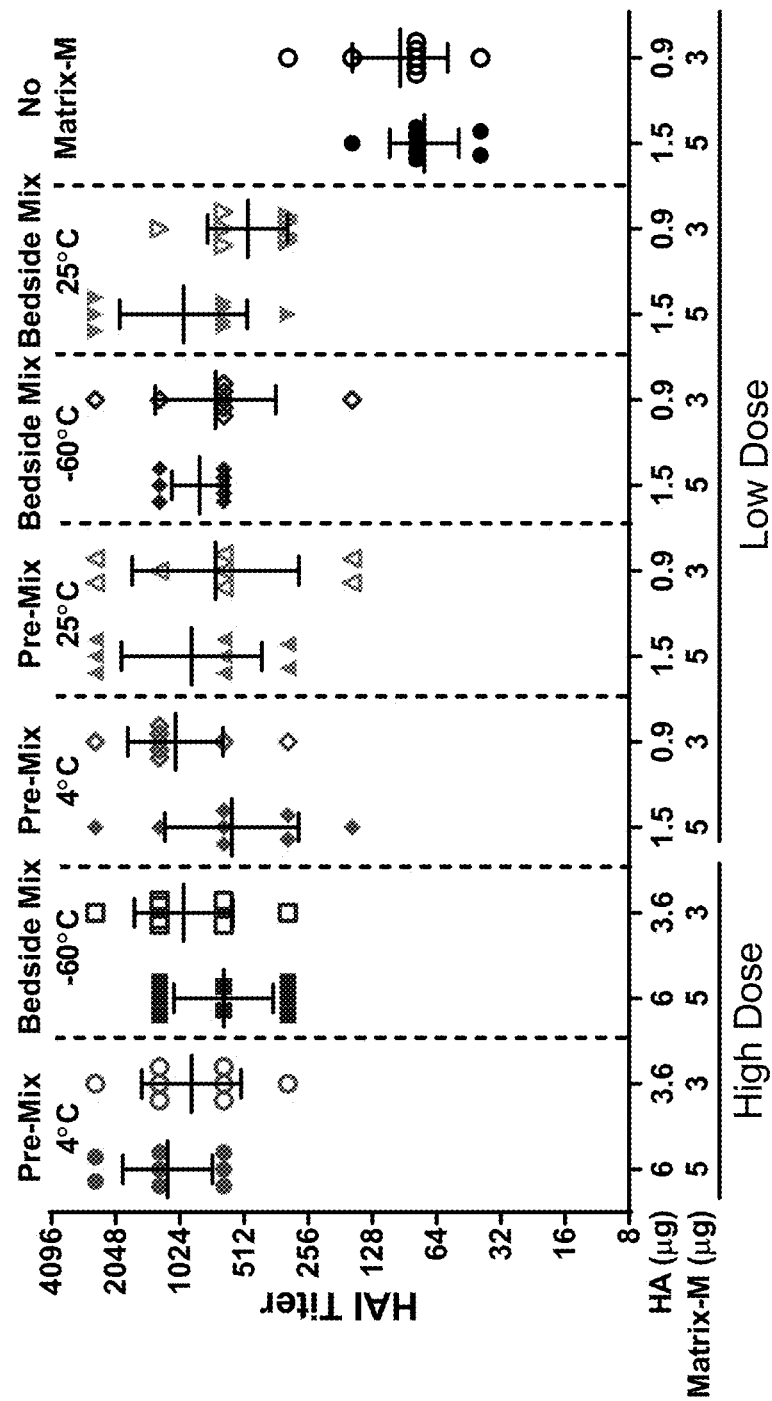
FIG. 19 illustrates hemagglutination inhibition antibody response against B/Phuket strain in mice administered with Quad-NIV co-formulations; or bedside mix formulations with or without Matrix M (100 µg/mL) at 35 days. The antibody response was presented as the HAI titers. The pre-mixed Quad-NIV co-formulations were stored at the indicated temperatures for 6 months.
Figure 20:
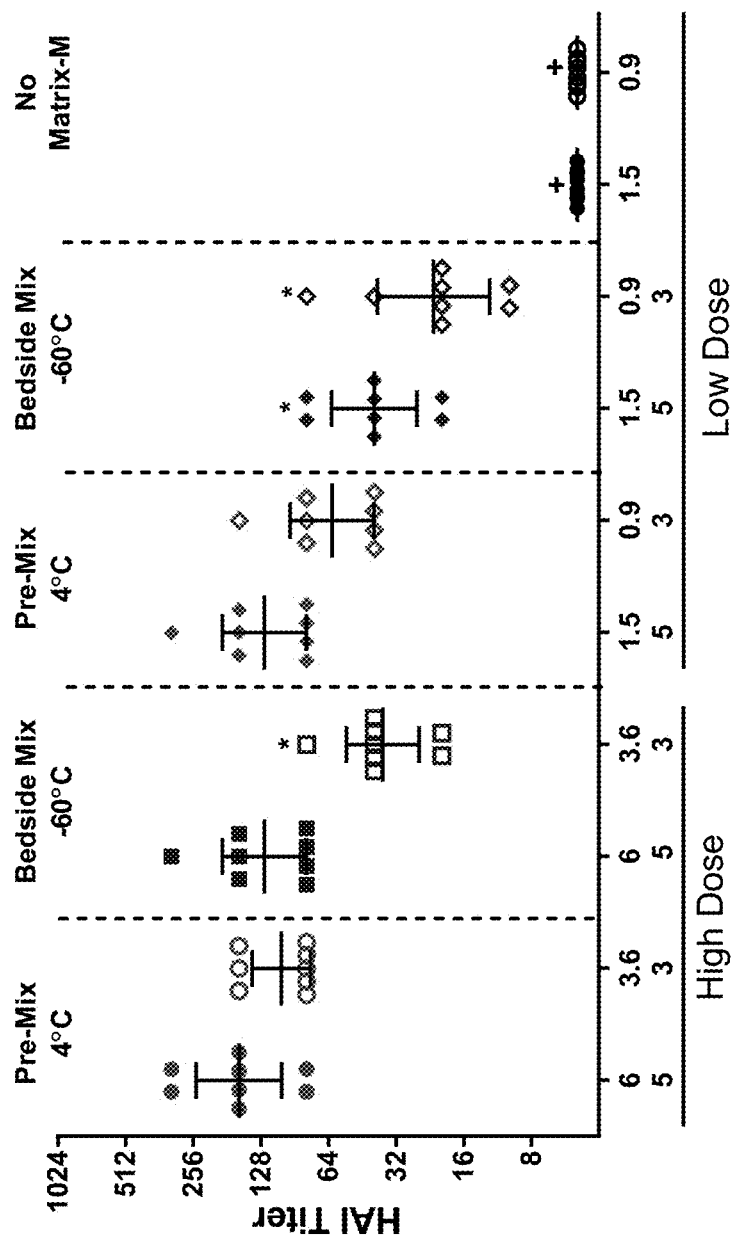
FIG. 20 illustrates hemagglutination inhibition antibody response against A/Hong Kong/4801/2014 in mice administered with Quad-NIV co-formulations; or bedside mix formulations with or without Matrix M (100 µg/mL) at 21 days. The pre-mixed Quad-NIV co-formulations were stored at 4° C. for 12 months.
Figure 21:
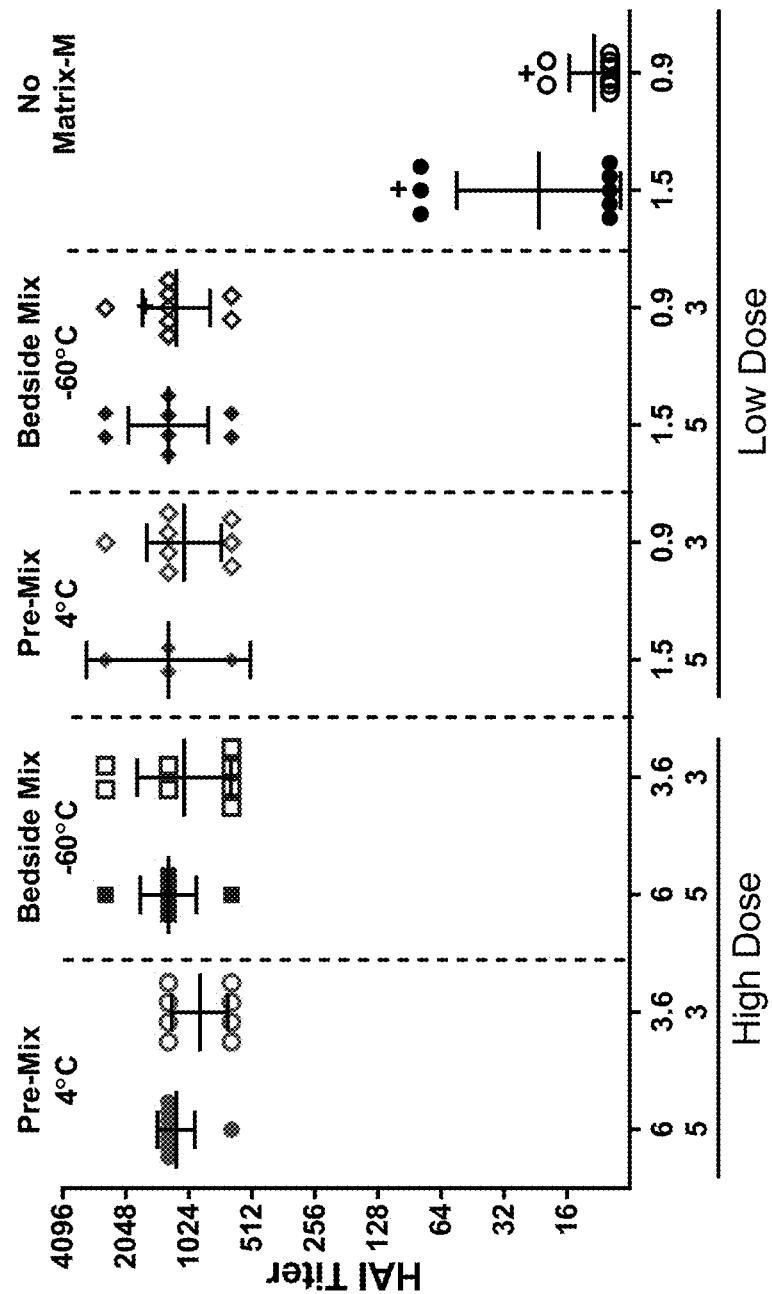
FIG. 21 illustrates hemagglutination inhibition antibody response against A/Hong Kong strain in mice administered with Quad-NIV co-formulations; or bedside mix formulations with or without Matrix M (100 µg/mL) at 35 days. The pre-mixed Quad-NIV co-formulations were stored at 4° C. for 12 months.
Figure 22:
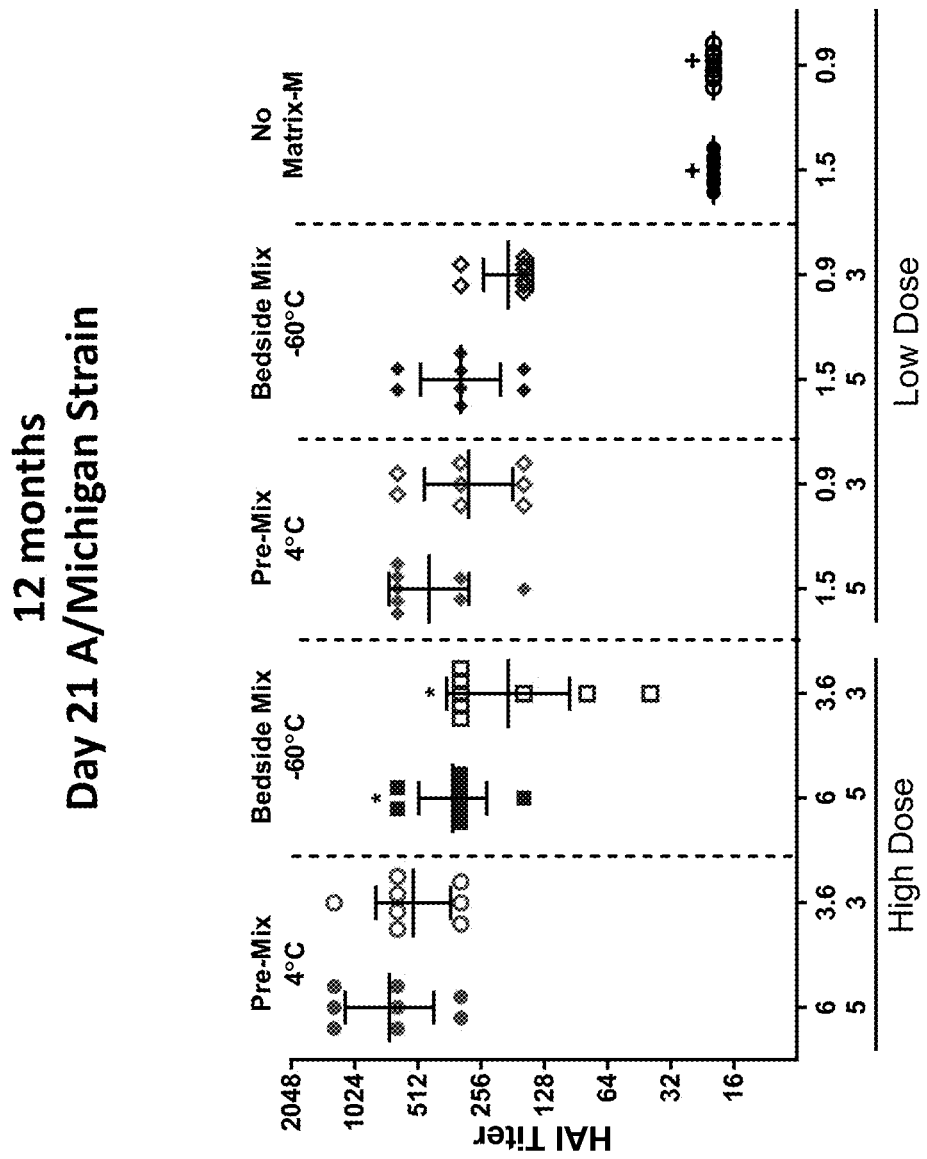
FIG. 22 illustrates hemagglutination inhibition antibody response against A/Michigan strains in mice administered with Quad-NIV co-formulations; or bedside mix formulations with or without Matrix M (100 µg/mL) at 21 days. The pre-mixed Quad-NIV co-formulations were stored at 4° C. for tions contain a combination of influenza antigens and ISCOM matrix adjuvant in the same container and prepared under conditions sufficient to form HaSMaNs (Hemagglutinin Saponin Matrix Nanoparticles).
Figure 23:
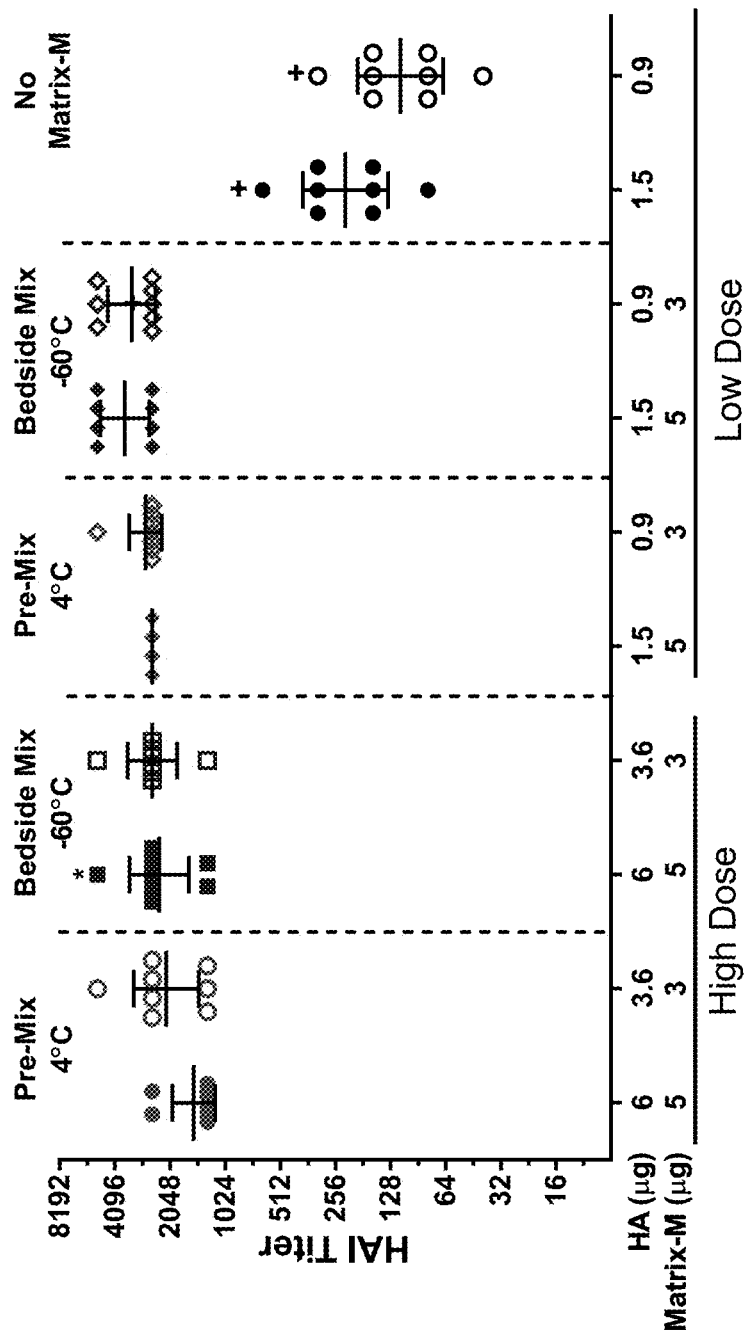
Figure 24:
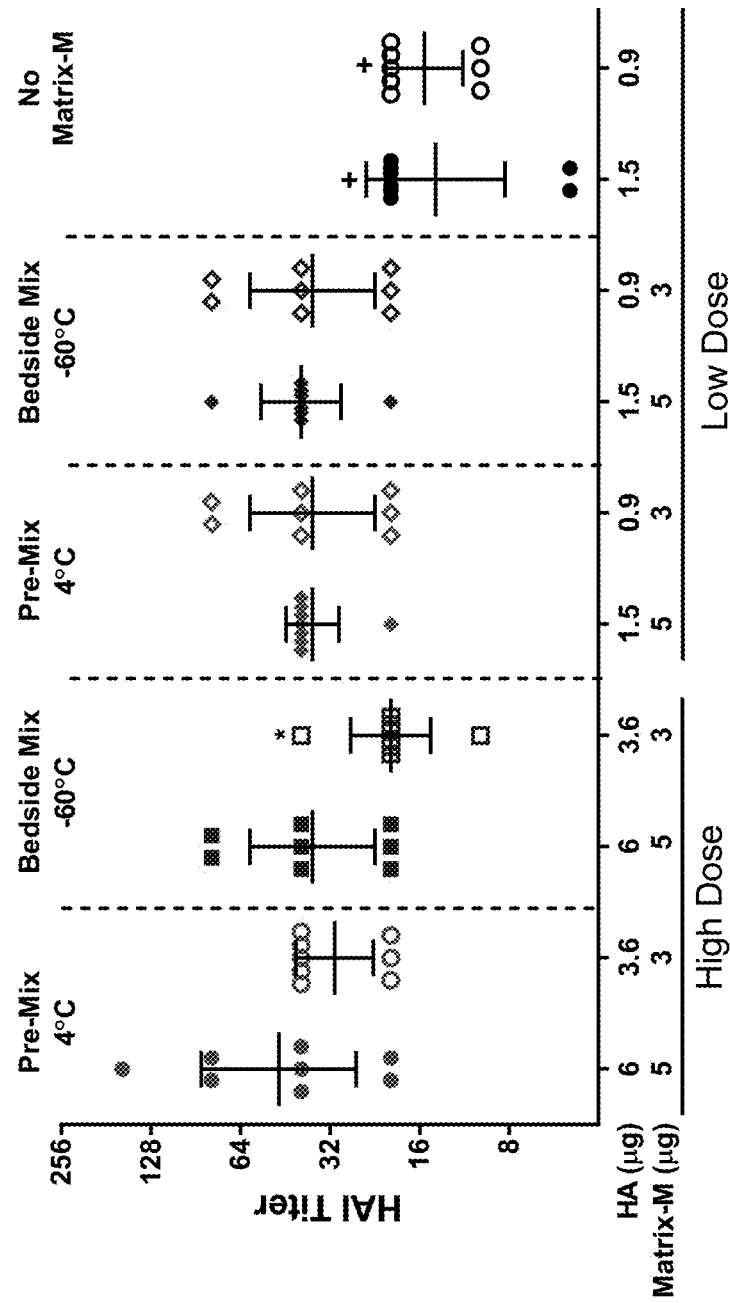
Figure 25:
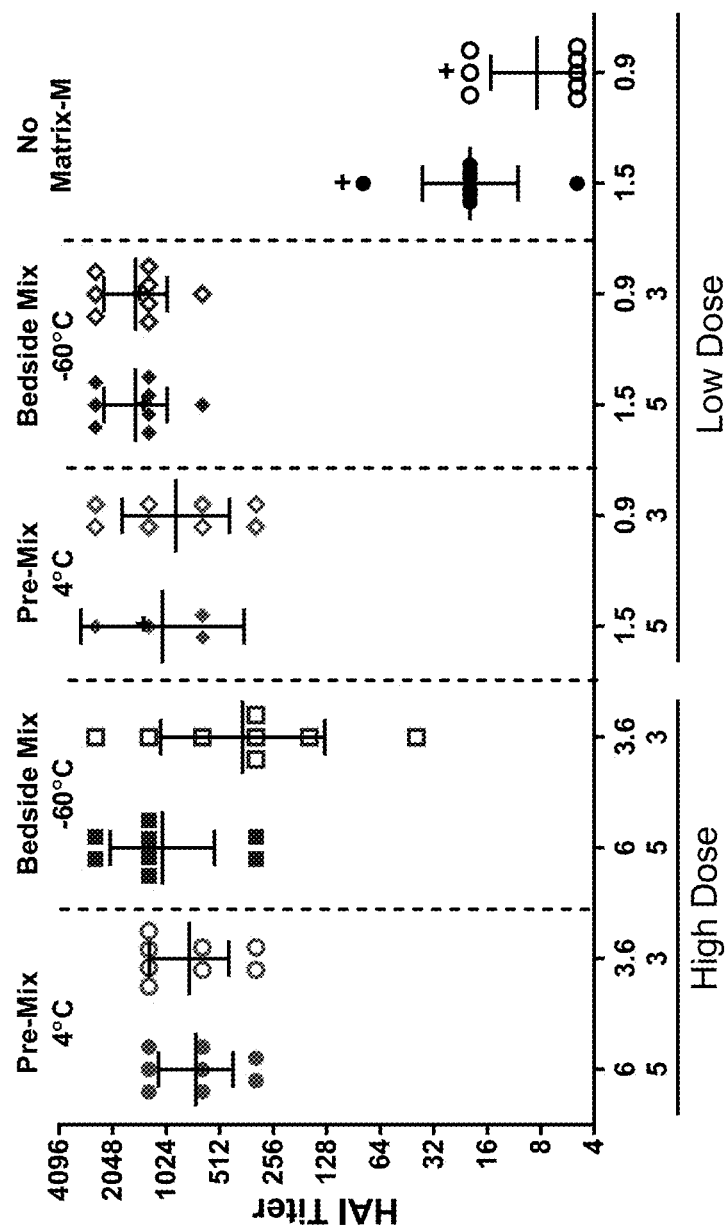
Figure 26:
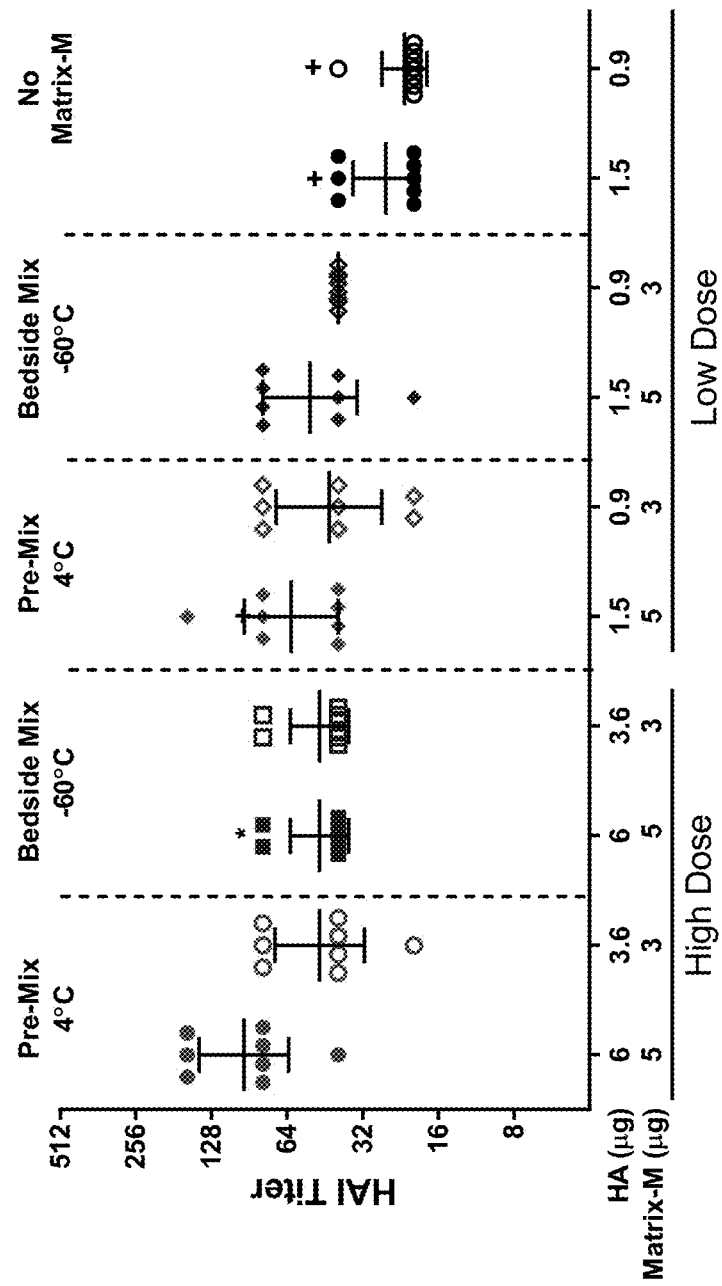
Figure 27:
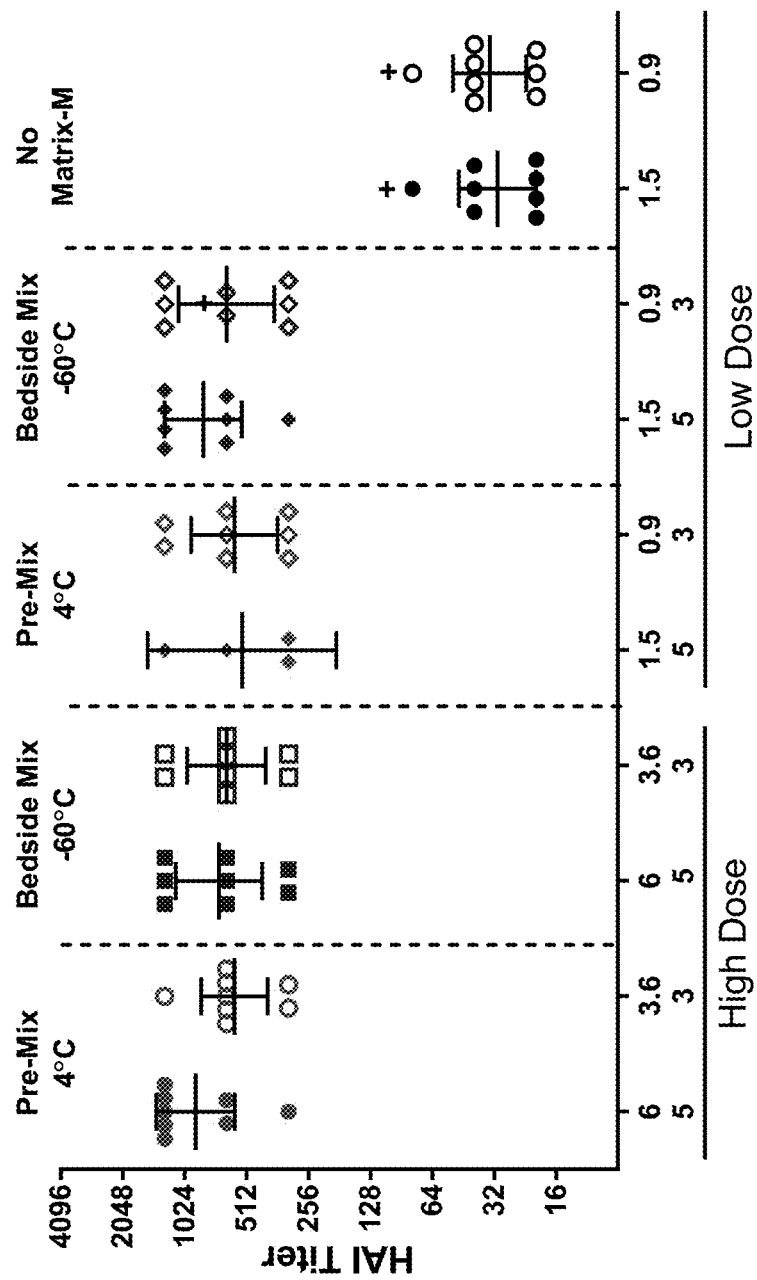
Figure 28:
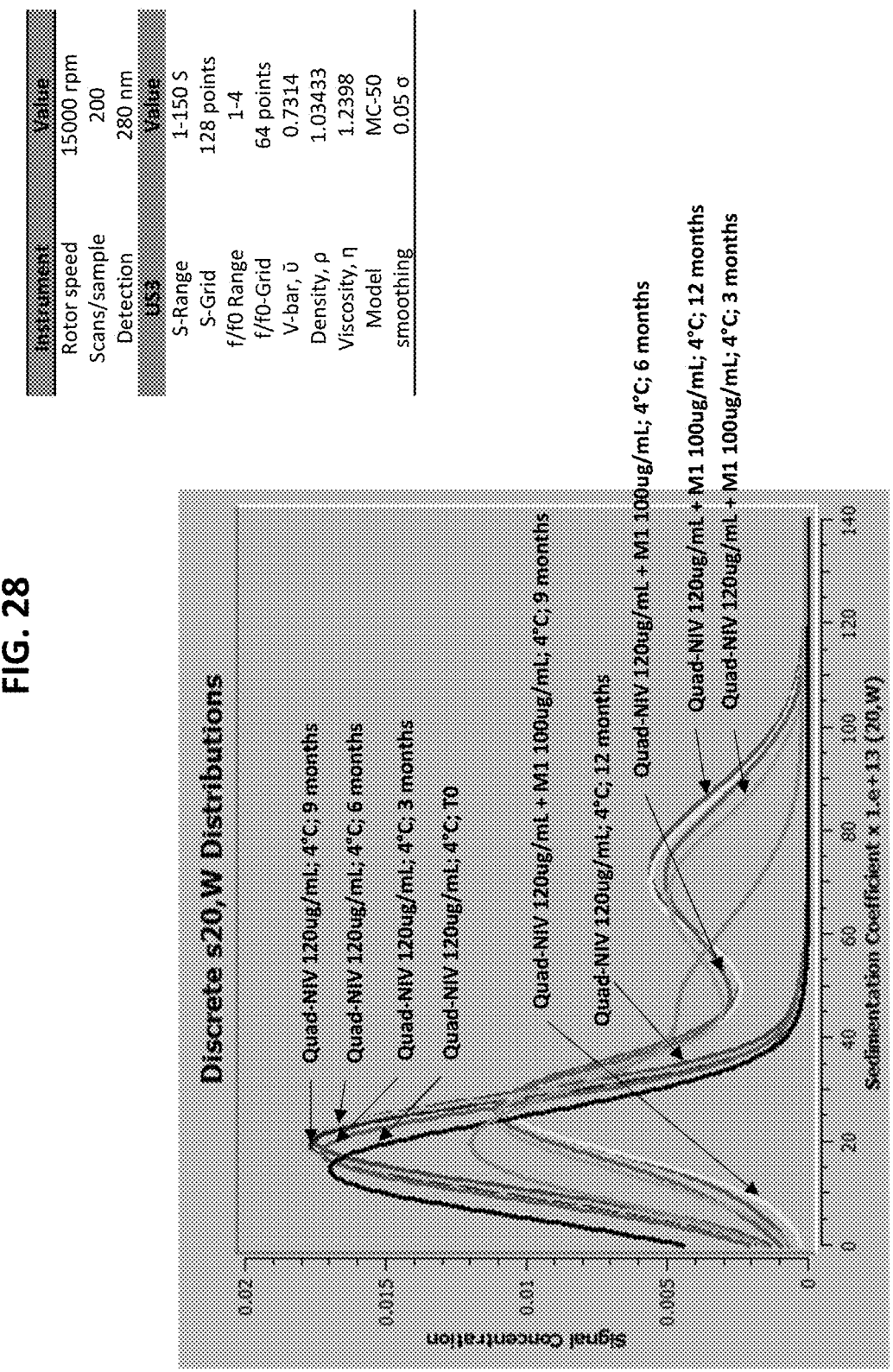
Figure 29:
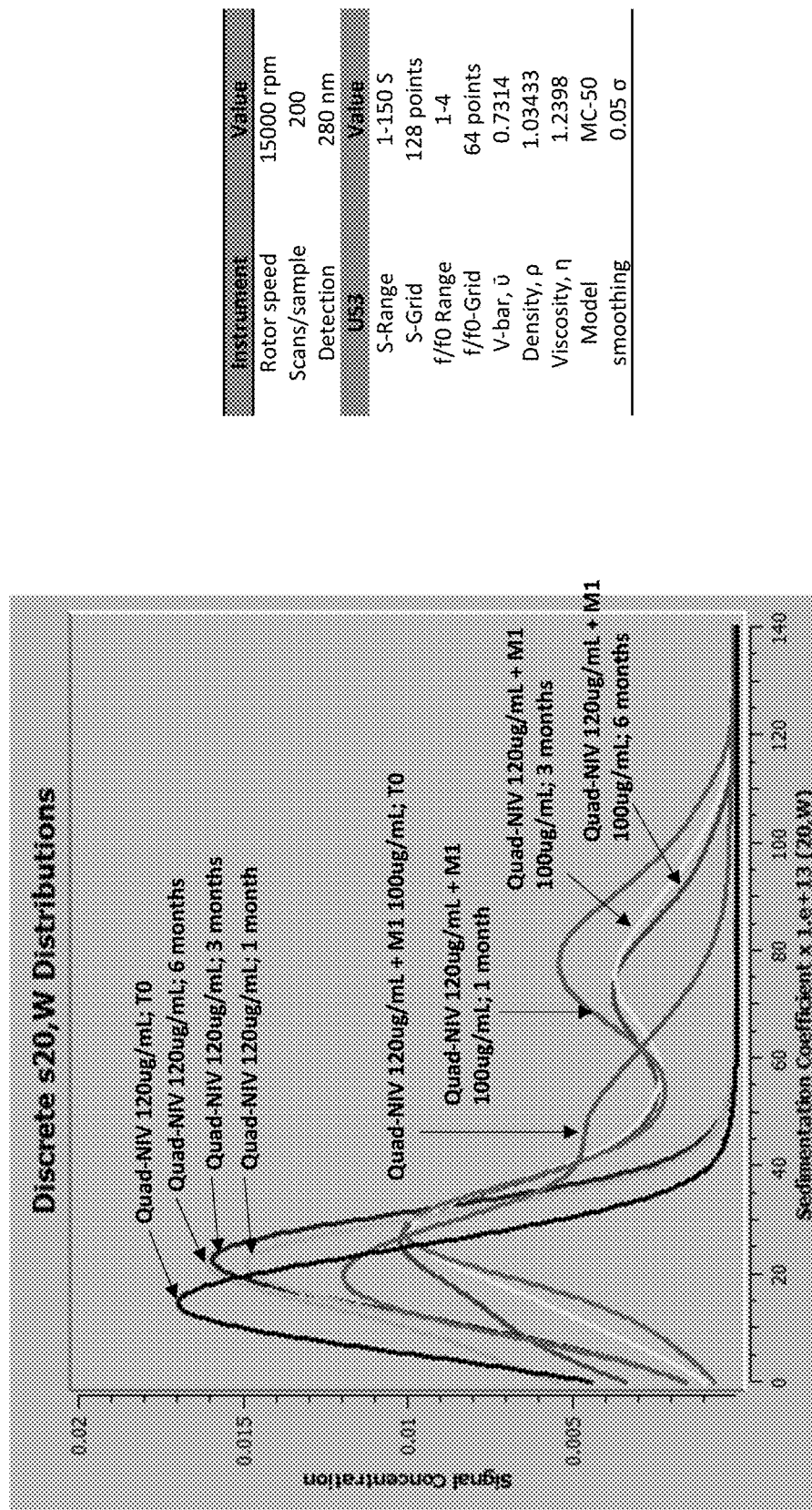

FIG. 11 shows the HAI titers against the four influenza strains for all HD groups at 3 months for the formulations listed in Table 3. The results show that pre-mixed formulations stored at 4° C. for 3 months had similar immunogenic capabilities compared with bedside mix formulations stored at −60° C. The results also show that Matrix M does not change the immunogenicity of the tested Quad-NIV formulations, even when the pre-mix formulation is stored for an extended period, such as 3 months.

Example 6—Immunogenicity and Long-Term Stability of Pre-Mix Versus Bedside Mix HA Nanoparticles with Matrix M at 25° C.

Groups 1 to 14 were prepared as shown in Table 4 below. For pre-mix groups, HA nanoparticles and Matrix M (85:15 w/w of Fraction A matrix and Fraction C matrix) were combined and stored at 4° C. for 6 months or 12 months, or at 25° C. for 6 months prior to administration. For bedside mix groups, HA was stored at 25° C. or frozen at −60° C. for 6 months or frozen at −60° C. at 12 months, then combined with Matrix M immediately before administration to the mouse. The HA protein nanoparticles contained HA from the following strains A/Michigan H1N1, A/Hong Kong-H3N2 B/Brisbane, and B/Phuket.

TABLE 3

Quad-NIV Formulations for Immunogenicity Assessments

| Group (N = 8) | Vaccine | Injection Volume | HA Dose | Matrix M | Immunization (Day) | Blood Collection (Day) |
| --- | --- | --- | --- | --- | --- | --- |
| 1 | Pre-Mix Stored at 4° C. | 50 µL | 6 µg | 5 µg | 0, 21 | −1, 42 |
| 2 | Pre-Mix Stored at 4° C. | 30 µL | 3.6 µg | 3 µg | 0, 21 | −1, 42 |
| 3 | Bedside Mix: Viral HA antigens stored at −60° C. mixed with Matrix immediately before administration | 50 µL | 6 µg | 5 µg | 0, 21 | −1, 42 |
| 4 | Bedside Mix: Viral HA antigens stored at −60° C. mixed with Matrix immediately before administration | 30 µL | 3.6 µg | 3 µg | 0, 21 | −1, 42 |

TABLE 4

Formulations for 6 Month and 12 months[3] Stability Analysis

| Group (N = 8) | Dose level | Vaccine | HA Dose | Matrix M | Immunization (Day) | Blood & Spleens Collection (Day) |
| --- | --- | --- | --- | --- | --- | --- |
| 1 | [1]High Dose | Pre-Mix | 6 µg | 5 µg | 0, 21 | −1, 20, 35 |
| 2 | | 4° C. | 3.6 µg | 3 µg | 0, 21 | −1, 20, 35 |
| 3 | | Bedside Mix | 6 µg | 5 µg | 0, 21 | −1, 20, 35 |
| 4 | | −60° C. | 3.6 µg | 3 µg | 0, 21 | −1, 20, 35 |
| 5 | [2]Low Dose | Pre-Mix | 1.5 µg | 5 µg | 0, 21 | −1, 20, 35 |

TABLE 4-continued

Formulations for 6 Month and 12 months[3] Stability Analysis

| Group (N = 8) | Dose level | Vaccine | HA Dose | Matrix M | Immunization (Day) | Blood & Spleens Collection (Day) |
|---|---|---|---|---|---|---|
| 6 | | 4° C. | 0.9 μg | 3 μg | 0, 21 | −1, 20, 35 |
| 7 | | Pre-Mix | 1.5 μg | 5 μg | 0, 21 | −1, 20, 35 |
| 8 | | 25° C. | 0.9 μg | 3 μg | 0, 21 | −1, 20, 35 |
| 9 | | Bedside Mix | 1.5 μg | 5 μg | 0, 21 | −1, 20, 35 |
| 10 | | −60° C. | 0.9 μg | 3 μg | 0, 21 | −1, 20, 35 |
| 11 | | Bedside Mix | 1.5 μg | 5 μg | 0, 21 | −1, 20, 35 |
| 12 | | 25° C. | 0.9 μg | 3 μg | 0, 21 | −1, 20, 35 |
| 13 | Antigen Only (No Matrix M) | Bedside Mix | 1.5 μg | N/A | 0, 21 | −1, 20, 35 |
| 14 | | −60° C. | 0.9 μg | N/A | 0, 21 | −1, 20, 35 |

[1]High dose: 120 μg/mL/strain (480 μg HA total) + 100 μg/mL Matrix.
[2]Low dose: 30 μg/mL/strain HA (120 μg HA total) + 100 μg/mL Matrix.
[3]The 12 month stability study did not include samples stored at 25° C.

We measured HAI titers against each of the four strains. FIGS. 12-19 and Tables 5-12 show HAI titers against A/Hong Kong, A/Michigan, B/Brisbane, and B/Phuket strains for HD and LD groups at 6 months.

TABLE 5

Day 21 A/Michigan H1N1-HAI Titers

| | Pre-Mix (4° C.) | | Bedside Mix (−60° C.) | | Pre-Mix (4° C.) | | Pre-Mix (25° C.) | | Bedside Mix (−60° C.) | | Bedside Mix (25° C.) | | No Matrix-M | |
|---|---|---|---|---|---|---|---|---|---|---|---|---|---|---|
| HA dose (μg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (μg) | 5 | 3 | 5 | 3 | 5 | 3 | 5 | 3 | 5 | 3 | 5 | 3 | — | — |
| GMT | 160 | 87 | 48 | 37 | 57 | 52 | 67 | 28 | 31 | 44 | 57 | 37 | 10 | 10 |
| 95% LCL | 160 | 60 | 32 | 30 | 37 | 31 | 51 | 17 | 23 | 27 | 42 | 25 | 10 | 10 |
| 95% UCL | 160 | 127 | 72 | 45 | 88 | 88 | 88 | 48 | 42 | 71 | 77 | 53 | 10 | 10 |

TABLE 6

Day 35 A/Michigan H1N1-HAI Titers

| | Pre-Mix (4° C.) | | Bedside Mix (−60° C.) | | Pre-Mix (4° C.) | | Pre-Mix (25° C.) | | Bedside Mix (−60° C.) | | Bedside Mix (25° C.) | | No Matrix-M | |
|---|---|---|---|---|---|---|---|---|---|---|---|---|---|---|
| HA dose (μg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (μg) | 5 | 3 | 5 | 3 | 5 | 3 | 5 | 3 | 5 | 3 | 5 | 3 | — | — |
| GMT | 640 | 640 | 830 | 587 | 538 | 587 | 538 | 415 | 640 | 587 | 453 | 320 | 147 | 208 |
| 95% LCL | 374 | 470 | 539 | 405 | 357 | 362 | 412 | 270 | 470 | 478 | 226 | 172 | 101 | 104 |
| 95% UCL | 1,094 | 872 | 1,277 | 851 | 811 | 952 | 704 | 639 | 872 | 720 | 905 | 595 | 213 | 413 |

TABLE 7

Day 21 A/Hong Kong-H3N2 HAI Titers

| | Pre-Mix (4° C.) | | Bedside Mix (−60° C.) | | Pre-Mix (4° C.) | | Pre-Mix (25° C.) | | Bedside Mix (−60° C.) | | Bedside Mix (25° C.) | | No Matrix-M | |
|---|---|---|---|---|---|---|---|---|---|---|---|---|---|---|
| HA dose (μg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (μg) | 5 | 3 | 5 | 3 | 5 | 3 | 5 | 3 | 5 | 3 | 5 | 3 | — | — |
| GMT | 34 | 28 | 12 | 11 | 18 | 14 | 22 | 12 | 8 | 8 | 11 | 9 | 5 | 5 |
| 95% LCL | 18 | 15 | 8 | 9 | 8 | 8 | 13 | 7 | 6 | 5 | 8 | 5 | 5 | 5 |
| 95% UCL | 61 | 53 | 18 | 13 | 40 | 26 | 35 | 20 | 11 | 13 | 16 | 16 | 5 | 5 |

TABLE 8

Day 35 A/Hong Kong-H3N2 HAI Titers

|  | Pre-Mix (4° C.) | | Bedside Mix (-60° C.) | | Pre-Mix (4° C.) | | Pre-Mix (25° C.) | | Bedside Mix (-60° C.) | | Bedside Mix (25° C.) | | No Matrix-M | |
| --- | --- | --- | --- | --- | --- | --- | --- | --- | --- | --- | --- | --- | --- | --- |
| HA dose (µg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (µg) | 5 | 3 | 5 | 3 | 5 | 3 | 5 | 3 | 5 | 3 | 5 | 3 | — | — |
| GMT | 381 | 415 | 494 | 381 | 453 | 538 | 538 | 320 | 494 | 494 | 349 | 208 | 18 | 28 |
| 95% LCL | 228 | 209 | 290 | 209 | 199 | 357 | 295 | 133 | 290 | 248 | 150 | 112 | 9 | 12 |
| 95% UCL | 636 | 826 | 839 | 693 | 1,027 | 811 | 980 | 769 | 839 | 982 | 812 | 384 | 38 | 64 |

TABLE 9

Day 21 B/Brisbane HAI Titers

|  | Pre-Mix (4° C.) | | Bedside Mix (-60° C.) | | Pre-Mix (4° C.) | | Pre-Mix (25° C.) | | Bedside Mix (-60° C.) | | Bedside Mix (25° C.) | | No Matrix-M | |
| --- | --- | --- | --- | --- | --- | --- | --- | --- | --- | --- | --- | --- | --- | --- |
| HA dose (µg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (µg) | 5 | 3 | 5 | 3 | 5 | 3 | 5 | 3 | 5 | 3 | 5 | 3 | — | — |
| GMT | 34 | 26 | 24 | 24 | 26 | 22 | 22 | 15 | 22 | 18 | 22 | 15 | 11 | 10 |
| 95% LCL | 26 | 19 | 18 | 18 | 19 | 15 | 15 | 11 | 13 | 13 | 18 | 11 | 9 | 10 |
| 95% UCL | 44 | 35 | 31 | 31 | 35 | 32 | 32 | 21 | 35 | 27 | 27 | 21 | 13 | 10 |

TABLE 10

Day 35 B/Brisbane HAI Titers

|  | Pre-Mix (4° C.) | | Bedside Mix (-60° C.) | | Pre-Mix (4° C.) | | Pre-Mix (25° C.) | | Bedside Mix (-60° C.) | | Bedside Mix (25° C.) | | No Matrix-M | |
| --- | --- | --- | --- | --- | --- | --- | --- | --- | --- | --- | --- | --- | --- | --- |
| HA dose (µg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (µg) | 5 | 3 | 5 | 3 | 5 | 3 | 5 | 3 | 5 | 3 | 5 | 3 | — | — |
| GMT | 381 | 381 | 269 | 293 | 293 | 494 | 320 | 147 | 453 | 269 | 123 | 147 | 28 | 34 |
| 95% LCL | 181 | 181 | 89 | 119 | 113 | 248 | 126 | 51 | 244 | 102 | 55 | 76 | 18 | 20 |
| 95% UCL | 800 | 800 | 813 | 722 | 760 | 982 | 810 | 418 | 841 | 708 | 279 | 282 | 44 | 56 |

TABLE 11

Day 21 B/Phuket HAI Titers

|  | Pre-Mix (4° C.) | | Bedside Mix (-60° C.) | | Pre-Mix (4° C.) | | Pre-Mix (25° C.) | | Bedside Mix (-60° C.) | | Bedside Mix (25° C.) | | No Matrix-M | |
| --- | --- | --- | --- | --- | --- | --- | --- | --- | --- | --- | --- | --- | --- | --- |
| HA dose (µg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (µg) | 5 | 3 | 5 | 3 | 5 | 3 | 5 | 3 | 5 | 3 | 5 | 3 | — | — |
| GMT | 73 | 44 | 31 | 52 | 40 | 34 | 44 | 44 | 24 | 24 | 52 | 22 | 10 | 10 |
| 95% LCL | 51 | 30 | 20 | 38 | 29 | 22 | 30 | 30 | 18 | 18 | 38 | 15 | 10 | 10 |
| 95% UCL | 106 | 63 | 47 | 70 | 55 | 51 | 63 | 63 | 31 | 31 | 70 | 32 | 10 | 10 |

TABLE 12

Day 35 B/Phuket HAI Titers

|  | Pre-Mix (4° C.) | | Bedside Mix (-60° C.) | | Pre-Mix (4° C.) | | Pre-Mix (25° C.) | | Bedside Mix (-60° C.) | | Bedside Mix (25° C.) | | No Matrix-M | |
| --- | --- | --- | --- | --- | --- | --- | --- | --- | --- | --- | --- | --- | --- | --- |
| HA dose (µg) | 6 | 3.6 | 6 | 3.6 | 1.5 | 0.9 | 1.5 | 0.9 | 1.5 | 0.9 | 1.5 | 0.9 | 1.5 | 0.9 |
| Matrix M (µg) | 5 | 3 | 5 | 3 | 5 | 3 | 5 | 3 | 5 | 3 | 5 | 3 | — | — |
| GMT | 1,174 | 905 | 640 | 987 | 587 | 1,076 | 905 | 698 | 830 | 698 | 987 | 494 | 73 | 95 |
| 95% LCL | 724 | 529 | 374 | 581 | 285 | 644 | 424 | 284 | 615 | 363 | 496 | 321 | 51 | 57 |
| 95% UCL | 1,904 | 1,548 | 1,094 | 1,678 | 1,208 | 1,799 | 1,933 | 1,716 | 1,120 | 1,340 | 1,964 | 760 | 106 | 159 |

FIGS. 20-27 show HAI titers against A/Hong Kong strains, A/Michigan strains, B/Brisbane strains, and B/Phuket strains for high dose (HD) and low dose (LD) groups at 12 months.

The data show that bedside mix vaccines and pre-mix vaccines produce similar immunogenicity in mice even after 6 months or 12 months storage by the measurements of HAI titers. The study also confirmed that the presence of Matrix M was beneficial for generating greater immune responses. Matrix M, even when stored for extended periods, does not change the immunogenicity of the tested Quad-NIV formulations.

Pre-mixed formulations at 25° C. had similar immunogenic capabilities compared with bedside mix formulations at 25° C. For instance, the 1.5 µg pre-mix groups stored at 4° C. or 25° C. elicited similar HAI titer response against A/Michigan strain on day 21 (Table 5; GMT: 57 vs. 67, respectively). Combined with the stability of the pre-mix formulations stored at 25° C. for extended periods, the vaccines are thus especially useful for settings where cold-chain storage may be limited or absent.

The data shown in FIGS. 12-27 show that the high dose groups, particularly the pre-mix formulations, had higher HAI titer responses compared with the low dose groups across all strains on day 21. The HAI titer responses on day 35 were higher in all groups across all strains compared with the HAI titer responses observed on day 21 (e.g., the A/Hong Kong HAI titers of the 1.5 pre-mix formulations at 25° C. on day 21 vs. day 35: 22 vs. 538), while minimal differences were observed between the high dose groups and the low dose groups on day 35.

The data confirm that the HaSMaN particles, formed with type A HA proteins, are at least as effective at inducing immune responses as HA nanoparticles with a detergent core not in HaSMaN form. The data shows that the interaction of HA nanoparticles with Matrix to form the HaSMaN does not negatively impact either the adjuvant effect of the Matrix or the immunogenicity of the HA protein itself. While HA nanoparticles appear to preserve stability of the HA protein by insertion in the detergent core, the data thus suggests that the HaSMaN particles may provide some protection for the HA protein structure and may also positively impact presentation to the immune system, without requiring the HA protein embedded in the detergent core.

Example 7—Sedimentation Coefficient Analysis

The quadrivalent compositions that were previously tested for stability in mice in Example 6 were analyzed by analytical ultracentrifugation (AUC) to measure sedimentation velocity (SV) to determine particle size. FIG. 28 shows results with the Quad-NIV 120 μg/mL/strain alone (QIV alone) at 0, 3 months, 6 months, 9 months and 12 months at 4° C.; or QIV+100 μg/mL M1 at time 3 months, 6 months, 9 months and 12 months at 4° C. The data shows that as time progressed, there was an increasing amount of fast sedimenting species, i.e., structures appearing at higher values showing that the HA particles are formed into HaSMaNs with increasing time. FIG. 29 shows results with the Quad-NIV, alone or with 100 μg/mL M1 at 0, 3 months or 6 months at 25° C. and confirms that HaSMaNs formation is faster at higher temperature.

Example 8—Transmission Electron Microscopy (TEM) Analysis of Formation of HaSMaNs As previously described, FIG. 1 illustrates the different structures of HA nanoparticles (Flu), matrix M, and HaSMaNs (Flu-matrix interaction), as viewed using TEM. As expected, HA nanoparticles were free of HaSMaN formation. Rather, the HA nanoparticles exhibit the detergent core structure with HA proteins surrounding the core. Matrix M exhibits cage-like structures, which contain saponin fraction (either Fraction A or Fraction C but not both), phospholipid, and cholesterol. In the HaSMaN structures, the HA glycoprotein is attached to the cage-like matrix particles with the HA head portion extending outwards.

Next, we viewed a time-course of various samples described below under TEM to visually assess formation of HaSMaNs under the different conditions. Table 13 below shows the sample conditions and time points for testing the nanoparticle structures of pre-mix Quad-NIV formulations (high dose, HD and low dose, LD) by using TEM. The mark "X" indicates the sample conditions available for each time point. In addition, LD formulations were tested under various temperatures at 1 month (FIG. 35).

FIG. 30-FIG. 34 show representative images with HaSMaN structures. The data show that HaSMaN formation is visible at about 4 hours of incubation; and that there is no evidence of HaSMaN formation prior to 4 hours (FIG. 30 and FIG. 31). By 24 hours, HaSMaNs formed at both low (4° C.) and high (25° C.) temperatures; however, HaSMaN formation was not observed in high dose Quad-NIV at 4° C. High dose Quad-NIV shows HaSMaN formation at 4° C. by 48 hours (FIG. 33), and at 7 days (FIG. 34). The data also shows that by 1 month, HaSMaN structures remained in LD group and were more prominent at higher temperatures, especially at 37° C. (FIG. 35).

TABLE 13

TEM Imaging: Study Design

| Sample | T = 0 | 4 hrs | 24 hrs | 48 hrs | 7 days |
|---|---|---|---|---|---|
| 120 μg/mL/strain Quad Flu (4° C.) | X | | | | |
| 120 μg/mL/strain Quad Flu + Matrix M (4° C.) | X | X | X | X | X |
| 120 μg/mL/strain Quad Flu + Matrix M (25° C.) | | X | X | X | X |
| 30 μg/mL/strain Quad Flu + Matrix M (4° C.) | X | X | X | X | X |
| 30 μg/mL/strain Quad Flu + Matrix M (25° C.) | | X | X | X | X |
| Matrix M (4° C.) | X | | | | |

Matrix M concentration: 100 μg/mL in all samples

These data show that HaSMaN formation requires upwards of about 4 hour co-incubation of the HA nanoparticles with Matrix M1. All conditions show HaSMaN formation within 48 hours. The formed HaSMaN particles are stable for extended periods. HaSMaN formation develops earlier with higher temperature and lower dosing amounts of the Quad-NIV.

This suggests that pre-filled syringe formulations containing HaSMaNs may be stored at room temperature, or higher (e.g., 37° C.), which will avoid costs for low temperature storage and shipping, and prevent potential inconsistencies of mixing and preparing the vaccines right before vaccination in the clinic.

Example 9

Differential Scanning Calorimetry (DSC) Profiles of Quad-NIV

The stability of Quad-NIV formulations described in Examples 6 and 7 was examined by DSC assay. 120

µg/mL/strain Quad-NIV with 100 µg/mL Matrix M1 was prepared in buffers containing 25 mM *NaPi*, 150 mM NaCl, 100 mM Arginine, 5% Trehalose, 0.03% PS80 at pH 7.5. All Quad-NIV samples were incubated at 4° C. for 3 months, 6 months or 12 months; or 25° C. for 3 months or 6 months. The DSC scan was conducted from 4° C. to 120° C. at 1° C. per minute and the molar heat capacities (Cp: kFmol·k) of Quad-NIV were measured.

FIG. 36 shows that the formulations incubated at 25° C. had a smaller shift in melting temperature (Tm) and had broader peak width than the same groups incubated at 4° C. Table 14 shows that 120 µg/mL/strain Quad-NIV+Matrix M1 formulations incubated at 25° C. had lower $T_m$ than 4° C. at both 3 months (59.6° C. vs. 60.4° C.) and 6 months (59.0° C. vs. 60.4° C.). Table 14 also shows that formulations at 25° C. required less changes in Hcal to reach to the peak temperatures than 4° C., which further suggests that this formulation has relatively fewer HaSMaN complexes.

DSC profiles and $T_m$ are a measure of the thermal stability of a protein. The results show that the formation of HaS-MaNs increases the $T_m$ of the HA protein by about 0.5° C. to about 1° C., thereby improving the thermal stability of the HA protein in the HaSMaN compared to a detergent-core nanoparticle.

TABLE 14

DSC Profiles of High dose and Low dose Quad-NIV Formulations

| Samples | Conditions | Tm (° C.) | ΔHcal (kJ/mol) | ΔHv (kJ/mol) |
|---|---|---|---|---|
| Quad-NIV 120 µg/mL/strain + Matrix M1 100 µg/mL | 25 C. T3M | 59.59 | 953.3 | 574.5 |
| | 25 C. T6M | 58.99 | 723.0 | 497.4 |
| | 4 C. T3M | 60.40 | 1195 | 754.3 |
| | 4 C. T6M | 60.39 | 1139 | 772.1 |
| Quad-NIV 120 µg/mL/strain | 25 C. T3M | 59.69 | 1013 | 585.2 |
| | 4 C. T3M | 59.68 | 1194 | 623.2 |
| | 4 C. T6M | 59.93 | 1057 | 640.3 |
| Quad-NIV 30 µg/mL/strain + Matrix M1 100 µg/mL | 25 C. T3M | 60.48 | 1029 | 659.9 |
| | 4 C. T3M | 60.42 | 1159 | 686.6 |
| | 4 C. T6M | 60.44 | 1021 | 733.8 |
| Quad-NIV 30 µg/mL/strain | 25 C. T3M | 60.05 | 1090 | 573.5 |
| | 4 C. T3M | 60.15 | 1045 | 619.4 |
| | 4 C. T6M | 59.91 | 1124 | 633.0 |

Example 10—Type A Strains but not Type B Strain for HaSMaNs

We investigated the ability of HA glycoproteins from different influenza strains to form HaSMaNs. Detergent-core nanoparticles were prepared and purified as described in Example 1 for the following strains: Type A: A/Hunan, A/Guangdong (both H7N9 sub-type) and A/Panama and A/Hong Kong/4801/2014 (both H3N2 subtype) and for Type B: B/Brisbane/60/2008.

The nanoparticles were mixed with Matrix M (85:15 w/w of Fraction A matrix and Fraction C matrix) for up to 4 weeks. The final HA concentration was 120 µg/mL (60 µg each A strain+60 µg each B strain in 0.5 mL). Free nHA was measured. Results are shown in FIG. 37. Decrease in free nHA species corresponds to HaSMaN formation.

These data suggest that Type A strain HA glycoproteins form HaSMaNs but that Type B strain HA glycoproteins do not. We also tested an HA glycoprotein fusion protein having a foldon on the C terminal. The presence of the foldon blocked HaSMaN formation, indicating that the C-terminal must be free to permit the HA glycoprotein to form HaS-MaNs.

The invention claimed is:

1. A multivalent immunogenic influenza composition comprising
    (a) a detergent-core nanoparticle, wherein the detergent-core nanoparticle comprises a recombinant influenza hemagglutinin (HA) glycoprotein from a Type B influenza strain; and
    (b) a Hemagglutinin Saponin Matrix Nanoparticle (HaS-MaN), wherein the HaSMaN comprises a recombinant influenza HA glycoprotein from a Type A influenza strain and ISCOM matrix adjuvant, wherein the ISCOM matrix adjuvant consists of Fraction A Matrix and Fraction C Matrix; and
    (c) a pharmaceutically acceptable buffer.

2. The composition of claim 1 comprising an additional one or more detergent-core nanoparticles and an additional one or more HaSMaNs, wherein each detergent-core nanoparticle comprises a Type B strain HA glycoprotein, and each HaSMaN comprises a Type A strain HA glycoprotein, and wherein each HA glycoprotein is from a different influenza strain.

3. The composition of claim 1, wherein each of the nanoparticles is a trypsin-resistant nanoparticle.

4. The composition of claim 1, wherein the Fraction A Matrix and Fraction C Matrix are present at 85:15; w/w.

5. The composition of claim 1, wherein the detergent is PS-80.

6. The composition of claim 5, wherein the PS-80 detergent is present at about 0.03% to about 0.5%.

7. The composition of claim 5, wherein the PS-80 detergent is present at about 0.04%.

8. The composition of claim 1, wherein the influenza strain is of a subtype selected from the group consisting of H1, H2, H3, H4, H5, H6, H7, H8, H9, H10, H11, H12, H13, H14, H15, H16, H17, and H18.

9. The composition of claim 1, wherein the pharmaceutically acceptable buffer comprises (i) sodium phosphate at about 25 mM; (ii) sodium chloride at about 150 mM; (iii) arginine hydrochloride at about 100 mM; (iv) trehalose at about 5%; wherein the composition pH is at about 7.5.

10. A prefilled syringe or blow-fill seal container comprising the composition of claim 1.

11. The prefilled syringe or blow-fill seal container of claim 9, wherein the composition is stable for at least 12 months.

12. The prefilled syringe or blow-fill seal container of claim 10, wherein the composition is stable at 25° C.

13. A method of stimulating an immune response against influenza comprising administering the multivalent influenza composition of claim 1.

14. The method of claim 13, wherein the composition is administered intramuscularly.

15. The composition of claim 1, wherein the adjuvant is present at about 50 µg to about 75 µg per dose.

16. The composition of claim 1, wherein the recombinant influenza HA glycoprotein from the Type B influenza strain and the recombinant influenza HA glycoprotein from the Type A influenza strain are both present in an amount of about 60 µg.

17. The composition of claim 1, wherein the recombinant influenza HA glycoprotein from the Type B influenza strain and the recombinant influenza HA glycoprotein from the Type A influenza strain are both wild type influenza HA glycoproteins.

18. The composition of claim 1, wherein the recombinant influenza HA glycoprotein from the Type B influenza strain and the recombinant influenza HA glycoprotein from the Type A influenza strain are expressed in a host cell.

19. The composition of claim 18, wherein the host cell is an insect Sf9 cell.

20. The composition of claim 18, wherein the recombinant influenza HA glycoprotein from the Type B influenza strain and the recombinant influenza HA glycoprotein from the Type A influenza strain are expressed using a baculovirus.

* * * * *